(12) United States Patent
Bailey et al.

(10) Patent No.: US 6,291,640 B1
(45) Date of Patent: Sep. 18, 2001

(54) PEPTIDOMIMETIC INHIBITORS OF THE HUMAN CYTOMEGALOVIRUS PROTEASE

(75) Inventors: Murray D. Bailey, Pierrefonds; Gulrez Fazal, Roxboro; Pierre Lavallee; William Ogilvie, both of Rosemere; Marc-Andre Poupart, Laval, all of (CA)

(73) Assignee: Boehringer Ingelheim Ltd., Laval (CA)

( * ) Notice: Subject to any disclaimer, the term of this patent is extended or adjusted under 35 U.S.C. 154(b) by 0 days.

(21) Appl. No.: 09/171,554

(22) PCT Filed: Dec. 23, 1997

(86) PCT No.: PCT/CA97/01004

§ 371 Date: Oct. 19, 1998

§ 102(e) Date: Oct. 19, 1998

(87) PCT Pub. No.: WO98/29435

PCT Pub. Date: Jul. 9, 1998

Related U.S. Application Data

(60) Provisional application No. 60/059,806, filed on Sep. 23, 1997, provisional application No. 60/034,041, filed on Dec. 27, 1996, and provisional application No. 60/052,860, filed on Jul. 17, 1997.

(51) Int. Cl.[7] .................................................. C07K 5/10
(52) U.S. Cl. .......................... 530/330; 530/331; 514/17; 514/18; 514/19
(58) Field of Search .................. 514/17, 18, 19; 530/331, 330

(56) References Cited

FOREIGN PATENT DOCUMENTS

WO 97 10231A  3/1997  (WO).

OTHER PUBLICATIONS

Derstine, C.W., Trifluoromethyl–substituted imidazolines; novel precursors of trifluoromethyl ketones anenable to peptide synthesis, Journal of the American Chemical Society, vol. 228, No. 35, Sep. 4, 1996, pp. 8485–8486, XP 002065952.

Abuelyaman, A.H., Flourescent derivatives of diphenyl [1–(N–Peptidylamino) alkyl] phosphonate Esters: synthesis and use in the inhibition and cellular localization of serine proteases, Bioconjugate Chemistry, vol. 5, No. 5, Oct. 1994 Washington, US, pp. 400–405, XP000465951.

Murphy, A..M. et al., Automated synthesis of Peptide C–Terminal aldehydes Journal of the American Chemical Society., vol. 114, No. 8, Apr. 8, 1992 pp. 3156–3157.

Oglivie, W., et al; Peptidomimetic inhibitors of the human cytomegalovirus protease, Journal of Medicinal Chemistry., vol. 40, No. 25, Dec. 5, 1997, Washington, US, pp. 4113–4135, XP002065953.

Bonneau, P.B. et al, Evidence of conformational change in the human cytomegalovirus protease upon binding of peptidyl–activated carbonyl inhibitors, Biochemistry, vol. 36, No. 41, Oct. 14, 1997 Easton, PA, US, pp. 12640–12652.

*Primary Examiner*—Christopher S. F. Low
*Assistant Examiner*—David Lukton
(74) *Attorney, Agent, or Firm*—Robert P. Raymond; Alan R. Stempel; Mary-Ellen M. Devlin

(57) ABSTRACT

A compound of formula (I) is disclosed:

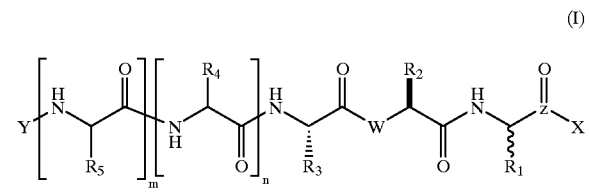

wherein X, z, W, Y, $R_1$ through $R_5$, m and n are as define herein. These compounds are peptidomimetic inhibitors of human cytomegalovirus (HCMV) protease and are useful for the treatment of human cytomegalovirus infection.

20 Claims, 3 Drawing Sheets

Dixon plot for competitive inhibition of compound 76 against HCMV protease.

Progress curve for the inhibition of HCMV protease by compound 65.

Progress curve for the inhibition of HCMV protease by compound 76.

SEQUENCE LISTING

<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:
      peptidomimetic inhibitor
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (5)
<223> OTHER INFORMATION: C-terminal is modified with activated carbonyl:
      C(O)CF3

<400> SEQUENCE: 1

Gly Val Val Asn Ala
 1               5

<210> SEQ ID NO 2
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (5)
<223> OTHER INFORMATION: C-terminal is modified with activated carbonyl:
      C(O)CF3
<223> OTHER INFORMATION: Description of Artificial Sequence:
      peptidomimetic inhibitor

<400> SEQUENCE: 2

Ser Trp Val Lys Ala
 1               5

```
<210> SEQ ID NO 3
<211> LENGTH: 4
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (4)
<223> OTHER INFORMATION: C-terminal is modified with activated carbonyl:
      C(O)CF3
<223> OTHER INFORMATION: Description of Artificial Sequence:
      peptidomimetic inhibitor

<400> SEQUENCE: 3

Val Val Asn Ala
  1

<210> SEQ ID NO 4
<211> LENGTH: 4
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (4)
<223> OTHER INFORMATION: C-terminal is modified with activated carbonyl:
      C(O)CF3
<223> OTHER INFORMATION: Description of Artificial Sequence:
      peptidomimetic inhibitor

<400> SEQUENCE: 4

Val Val Gln Ala
  1

<210> SEQ ID NO 5
<211> LENGTH: 4
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (4)
<223> OTHER INFORMATION: C-terminal is modified with activated carbonyl:
      C(O)CF3
<223> OTHER INFORMATION: Description of Artificial Sequence:
      peptidomimetic inhibitor

<400> SEQUENCE: 5

Val Val Asp Ala
  1

<210> SEQ ID NO 6
<211> LENGTH: 4
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (4)
<223> OTHER INFORMATION: C-terminal is modified with activated carbonyl:
      C(O)CF3
<223> OTHER INFORMATION: Description of Artificial Sequence:
      peptidomimetic inhibitor

<400> SEQUENCE: 6
```

Val Val Ser Ala
1

<210> SEQ ID NO 7
<211> LENGTH: 4
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (4)
<223> OTHER INFORMATION: C-terminal is modified with activated carbonyl:
      C(O)CF3
<223> OTHER INFORMATION: Description of Artificial Sequence:
      peptidomimetic inhibitor

<400> SEQUENCE: 7

Val Val Lys Ala
1

<210> SEQ ID NO 8
<211> LENGTH: 4
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (4)
<223> OTHER INFORMATION: C-terminal is modified with activated carbonyl:
      C(O)CF3
<223> OTHER INFORMATION: Description of Artificial Sequence:
      peptidomimetic inhibitor

<400> SEQUENCE: 8

Val Val Leu Ala
1

<210> SEQ ID NO 9
<211> LENGTH: 4
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (4)
<223> OTHER INFORMATION: C-terminal is modified with activated carbonyl:
      C(O)CF3
<223> OTHER INFORMATION: Description of Artificial Sequence:
      peptidomimetic inhibitor

<400> SEQUENCE: 9

Val Val Phe Ala
1

<210> SEQ ID NO 10
<211> LENGTH: 4
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (4)
<223> OTHER INFORMATION: C-terminal is modified with activated carbonyl:

```
          C(O)CF3
<223> OTHER INFORMATION: Description of Artificial Sequence:
      peptidomimetic inhibitor

<400> SEQUENCE: 10

Val Val Val Ala
 1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:
      peptidomimetic inhibitor
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (4)
<223> OTHER INFORMATION: C-terminal is modified with activated carbonyl:
      C(O)CF3

<400> SEQUENCE: 11

Val Val Ala Ala
 1

<210> SEQ ID NO 12
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with acetyl
<221> NAME/KEY: PEPTIDE
<222> LOCATION: (5)
<223> OTHER INFORMATION: C-terminal is modified with activated carbonyl:
      C(O)-NH-CH2-phenyl
<223> OTHER INFORMATION: Description of Artificial Sequence:
      peptidomimetic inhibitor

<400> SEQUENCE: 12

Ser Tyr Val Lys Ala
 1               5

<210> SEQ ID NO 13
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: N-terminal is capped with Boc
<221> NAME/KEY: PEPTIDE
<222> LOCATION: (3)
<223> OTHER INFORMATION: Xaa at position 3 is dimethyl asparagine
<221> NAME/KEY: PEPTIDE
<222> LOCATION: (4)..(5)
<223> OTHER INFORMATION: Carboxy added between Ala at position 4 and Ala
      at position 5
<221> NAME/KEY: PEPTIDE
<222> LOCATION: (5)
<223> OTHER INFORMATION: Carbonyl group at C-terminal replaced by
      OCH2phenyl
<223> OTHER INFORMATION: Description of Artificial Sequence:
      peptidomimetic inhibitor

<400> SEQUENCE: 13

Val Val Xaa Ala Ala
 1               5
```

PEPTIDOMIMETIC INHIBITORS OF THE HUMAN CYTOMEGALOVIRUS PROTEASE

This application claims the benefit of Provisional Application No. 60/034,041, filed Dec. 27, 1996, Provisional Application No. 60/052,860, filed Jul. 17, 1997, and Provisional Application No. 60/059,806, filed Sep. 23, 1997.

FIELD OF THE INVENTION

The present invention relates to compounds, composition and methods for the treatment of human cytomegalovirus (HCMV) infection. In particular, the present invention provides novel peptidomimetic inhibitors of the HCMV protease.

BACKGROUND OF THE INVENTION

The Human Cytomegalovirus (HCMV) is a highly prevalent member of the herpesvirus family infecting up to 80% of the general population. This virus is responsible for opportunistic infections in immunocompromised individuals including organ transplant recipients, cancer patients and AIDS sufferers. Clinical manifestations include disseminated disease, pneumonitis, retinitis and gastro-intestinal infections such as oesophagitis and colitis. Of particular significance are HCMV infections of neonates. This disease is the most common congenitally acquired viral infection in the world. It is estimated that 1% of newborn infants are infected and up to 10% of these are symptomatic and may experience severe complications. Mortality in this latter group approaches 30%.

All members of the herpesvirus family express a protein late in the virus life cycle which appears to function as a self assembling scaffold during the manufacture of the viral capsid. This assembly protein is present in immature B-capsids and must be processed to remove a short segment of the C-terminus in order to permit the entry of viral DNA and produce an infectious virus particle. Recently it has been shown that this processing is mediated by a protease which is encoded by the virus. The protease itself is expressed as a precursor protein which is autocatalytically cleaved at least twice (Scheme 1). Cleavage occurs near the C-terminal end of the UL80 gene product (M-site) to remove a small fragment, and also at a position located near the center of the precursor (R-site) to excise the catalytic domain ($N_o$). Both $N_o$ and the full length protease (UL80 gene product) are catalytically active.

Scheme 1

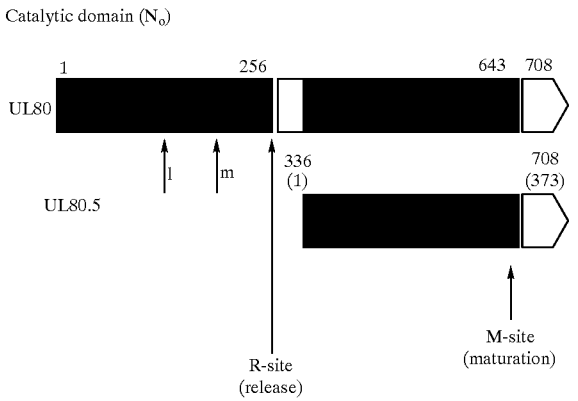

HCMV protease $N_o$ shows significant sequence homology with other herpesvirus proteases. Affinity labeling experiments and site-directed mutagenesis indicate that this enzyme is a serine protease. Recent crystallographic results have shown that HCMV protease represents a novel structure of serine proteases and in fact possesses a unique catalytic triad.

While it has not been demonstrated that HCMV protease is absolutely required for viral replication, it has been shown that HSV-1 mutants lacking the analogous enzyme or expressing defective variations of it are unable to grow. The high degree of homology between the proteases of HSV and HCMV support the idea that specific inhibitors of HCMV protease would show antiviral activity and thus have therapeutic value.

EP 0,410,411 A2 discloses novel peptidase inhibitors. These peptide analogs all contain a pentafluoroethylketone at P1', however none of the peptide disclosed contain the amino acid derivatives at P2 disclosed in the present invention.

A. H. Abuelyaman et al. (Bioconjuate Chemistry, vol.5, no.5, October 1994, pp.400–405) discloses fluorescent peptide phosphonates. However, none of the peptides disclosed corresponds or leads to the peptide derivatives of the invention.

Derstine et al. (J. Am. Chem. Soc., vol. 118, no. 35, Sep. 4, 1996, pp. 8485–8486 discloses a number of peptidyl trifluoromethylketones. None of these peptides corresponds or leads to the peptide derivatives of the invention.

SUMMARY OF THE INVENTION

In accordance with the present invention, there is provided a compound of formula I:

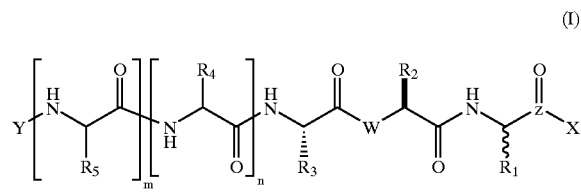

(I)

wherein z is C or P;
  when z is C, then X is $CF_3$; $C_2F_5$; benzothiazole; oxazolo[4,5b]pyridine; or benzoxazole-$R_7$ wherein $R_7$ is H or methyl;
  or X is $CF_2CONH-R_7$, $C(O)NH-R_6$,
    wherein $R_6$ is $C_{0-10}$ alkyl optionally substituted with phenyl or cyclohexyl, said phenyl or cyclohexyl ring being optionally substituted with Me, halogen —$CF_3$, —CH(Me)—C(O)—OBn; —C(O)$NH_2$; or —C(O)-morpholino; said phenyl or cyclohexyl ring optionally fused with a phenyl ring;
    $(CH_2)_{1-3}$—O—$(CH_2)_{1-3}$-phenyl said phenyl optionally substituted with halogen;
    $(CH_2)_{1-3}$-2-benzimidazole;
    $(CH_2)_{1-3}$-(3,4-methylenedioxybenzene); or
    $(CH_2)_{1-3}$—O—C(O)—$OCH_2CH=CH_2$;
  or, when z is P, then X is —$(OPh)_2$;
$R_1$ is H, Me, or Et;
$R_2$ is $CH_2$—$SO_2NH_2$; —$C_{1-6}$ alkyl; —$(C_{1-6}$ alkyl) aryl; —$(C_{1-6}$ alkyl)thiazolo; —$CH_2C(O)$—$(C_{1-6}$ alkyl); —$CH_2C(O)$-pyrrolidino; —$CH_2C(O)$-morpholino; —$(C_{1-6}$ alkyl)amino; —$(C_{1-6}$ alkyl)amido optionally mono- or di-substituted with $C_{1-6}$ alkyl, said alkyl optionally substituted with pyridino;
W is NH, $CH_2$ or $CH(CH_3)$;

$R_3$ is —$C_{1-12}$ alkyl; —($C_{1-6}$ alkyl)C(O)OH; or adamantyl;

n is 0 or 1, $R_4$, when n is 1, is -$C_{1-6}$ alkyl or —($C_{1-6}$ alkyl)-aryl wherein said aryl is optionally substituted with OH;

m is 0 or 1, $R_5$, when m is 1, is H or —$CH_2OH$; and

Y is H; $(CH_2)_2$-t-Bu; or an acyl of formula:

—C(O)—$(CH_2)_{1-6}$—C(O)OH;

—C(O)—$(CH_2)_{1-6}$—Ph wherein Ph is optionally substituted with OH;

—C(O)—$CH_2N(CH_3)_2$;

C(O)—$R_9$; —C(O)O—$R_9$; or —C(O)NH—$R_9$ wherein $R_9$ is $C_{1-6}$ alkyl; or

—C(O)—$(CH_2)_{1-6}$—$NH_2$ wherein said amino group is optionally protected with an amino protecting group.

Included within the scope of this invention is a pharmaceutical composition comprising an anti-cytomegalovirus virally effective amount of a compound of formula I or a therapeutically acceptable salt thereof, in admixture with a pharmaceutically acceptable carrier medium or auxiliary agent.

An important aspect of the invention involves a method of treating a cytomegalovirus viral infection in a mammal by administering to the mammal an anti-CMV virally effective amount of the compound of formula I or a therapeutically acceptable salt thereof, or a composition as described above.

Another important aspect involves a method of inhibiting the replication of cytomegalovirus virus by exposing the virus to a CMV protease inhibiting amount of the compound of formula I or a therapeutically acceptable salt thereof, or a composition as described above.

Preferred compounds of the invention include compounds of formula I:

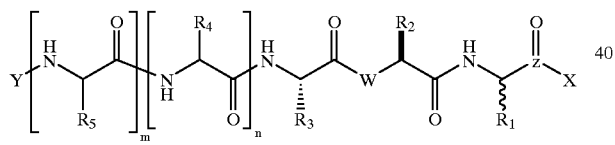

(I)

wherein the substituents are defined below.

Preferably, z is C. or P.

More preferably, z is C.

Preferably, X is $CF_3$;

$C_2F_5$;

2-benzothiazole;

2-oxazolo[4,5b]pyridine;

2-benzoxazole-$R_7$, wherein $R_7$ is H, 4-Me, 5-Me, 6-Me, or 7-Me;

$CF_2CONHR_6$ or $C(O)NHR_6$ wherein $R_6$ is $C_{1-7}$ alkyl, optionally substituted with cyclohexyl, naphtyl, or phenyl optionally substituted with Me, iodo, $CF_3$, —CH(Me) —C(O) —OBn; —C(O)$NH_2$, or —C(O)-morpholino;

$(CH_2)_2$—O—$CH_2$-phenyl;

$CH_2$-2-benzimidazole; or $CH_2$—(3,4-methylenedioxybenzene);

or when z is P, then X is (OPh)$_2$.

More preferably, X is $CF_3$;

$C_2F_5$;

benzothiazole;

benzoxazole-$R_7$, wherein $R_7$ is H, 4-Me, 5-Me, 6-Me, or 7-Me;

—$CF_2$CONH—$CH_2$-phenyl;

—C(O)$NHR_6$ wherein $R_6$ is —CH(Me) $(CH_2)_4CH_3$; cyclohexyl; naphtyl; —$CH_2$-phenyl; —CH $(CH_3)$-phenyl; or —CH $(CH_2CH_3)$-phenyl; —$CH_2$-4-iodophenyl; -phenyl-$CH_3$; -phenyl-$CF_3$; -phenyl-C(O)$NH_2$; -phenyl-C(O)-morpholino; -phenyl-CH(Me)—C(O)—OBn; —($CH_2)_2$—O—$CH_2$-phenyl; —$CH_2$-2-benzimidazole; —$CH_2$-(3,4-methylenedioxybenzene); or —$(CH_2)_2$—O—C(O)—$OCH_2CH$=$CH_2$;

or when z is P, then X is (OPh)$_2$.

Most preferably, X is $C_2F_5$;

—C(O)$NHR_6$ wherein $R_6$ is —$CH_2$-phenyl; —$CH_2$-4-iodophenyl; —CH $(CH_3)$-phenyl; or —CH($CH_2CH_3$) -phenyl; —CH (Me)-naphtyl; —$CH_2CH$(Me)-phenyl; —$(CH_2)_2$—O—$CH_2$-phenyl; —$CH_2$-2-benzimidazole; or —$CH_2$-(3,4-methylenedioxybenzene);

Preferably, $R_1$ is H, methyl or ethyl.

More preferably, $R_1$ is H or methyl.

Most preferably, $R_1$ is H or methyl;

Preferably, $R_2$ is —$CH_2$-phenyl;

—$CH_2$-(4-thiazolo);

—$(CH_2)_{1-4}$—$NH_2$;

—$CH_2$—C(O)-tert-butyl;

—$CH_2$—C(O)—(N-pyrrolidino);

—$CH_2$—C(O)—(N-morpholino);

—$CH_2SO_2NH_2$;

—$(CH_2)_{1-2}$-amido, the nitrogen of said amido optionally mono- or di-substituted with a substituent selected independently from: $CH_3$; t-Bu; phenyl; or —$CH_2CH_2$—(2-pyridino).

More preferably, $R_2$ is —$CH_2$—C(O)—(N-pyrrolidino);

—$CH_2$—C(O)—(N-morpholino);

—$CH_2SO_2NH_2$;

—$(CH_2)C(O)NH_2$;

—$(CH_2)_2C(O)N(CH_3)_2$;

—$CH_2$—C(O)—NH-t-Bu; or

—$(CH_2)_2$—C(O)—N($CH_3$) $CH_2CH_2$(2-pyridino)

Most preferably, $R_2$ is —$CH_2$—C(O)—(N-pyrrolidino);

—$CH_2$—C(O)—(N-morpholino);

—$(CH_2)_2C(O)N(CH_3)_2$; or

—$(CH_2)_2$—C(O)—N($CH_3$)$CH_2CH_2$(2-pyridino)

Preferably, W is NH or $CH_2$.

More preferably, W is NH.

Preferably, $R_3$ is ethyl; isopropyl; t-Bu; $CH_2$-t-Bu; or adamantyl.

More preferably, $R_3$ is ethyl; isopropyl; or t-Bu.

Most preferably, $R_3$ is isopropyl; or t-Bu.

Preferably, n is 0 or 1.

More preferably, n is 0.

Alternatively, more preferably, n is 1.

Preferably, $R_4$, when n is 1, is isopropyl; t-Bu; or 4-hydroxybenzyl. More preferably, $R_4$, when n is 1, is isopropy; or t-Bu. Most preferably, $R_4$, when n is 1, is t-Bu;

Preferably, m is 0 or 1. More preferably, m is 0.

Preferably, $R_5$, when m is 1, is H.

Preferably, Y is H; —$CH_2$—$CH_2$-t-Bu; or an acyl of formula:

—C(O)$CH_3$;

—C(O)CH₂—CH(CH₃)₂;
—C(O)CH₂—t-Bu (DA-Tbg)
—C(O)(CH₂)₂-4-hydroxyphenyl;
—C(O)—(CH₂)₃—COOH;
—C(O)O—t-Bu (Boc);
—C(O)NH—t-Bu;
—C(O)CH₂—N(CH₃)₂; or
—C(O)(CH₂)₁₋₆NH₂, said amino group optionally protected with an amino protecting group.

More preferably, Y is H; or an acyl of formula:
—C(O)CH₃;
—C(O)CH₂—CH(CH₃)₂;
—C(O)CH₂-t-Bu (DA-Tbg)
—C(O)(CH₂)₂-4-hydroxyphenyl;
—C(O)—(CH₂)₃—COOH;
—C(O)O-t-Bu (Boc);
—C(O)(CH₂)₅NH₂; or
—C(O)(CH₂)₅NH—Boc.

Most preferably, Y is an acyl of formula:
—C(O)CH₂-t-Bu (DA-Tbg);
—C(O)O-t-Bu (Boc);
—C(O)(CH₂)₅NH₂; or
—C(O)(CH₂)₅NH—Boc.

A preferred compound of the invention is selected from the group consisting of:

N1-(3,3,3-trifluoro-1-methyl-2-oxopropyl)-(2S)-2-((1S)-2-methyl-1-[((1S)-2-methyl-1-[(methylcarboxamido) methyl] carboxamidopropyl) carboxamido] propylcarboxamido) butanediamide (37) [SEQ ID NOS: 1 & 2];

N1-(3,3,3-trifluoro-1-methyl-2-oxopropyl)-(2S)-6-amino-2-((1S)-1-[((1S)-1-[(1S)-2-hydroxy-1-(methylcarboxamido) ethyl]carboxamido-2-(4-hydroxyphenyl)ethyl)carboxamido]-2-methylpropyl-carboxamido)hexanamide (38) [SEQ ID NOS: 3 & 4];

N1-(3,3,3-trifluoro-1-methyl-2-oxopropyl)-(2S)-2-[((1S)-2-methyl-1-[(1S)-2-methyl-1-(methylcarboxamido)propyl] carboxamidopropyl) carboxamido]butanediamide (39) [SEQ ID NOS 5 & 6];

N1-(3,3,3-trifluoro-1-methyl-2-oxopropyl)-(2S)-2-{(1S)-2-methyl-1-[(methylcarboxamido)propyl] carboxamido}butanediamide (40);

N1-(3,3,3-trifluoro-(1S)-methyl-2-oxopropyl)-(2S)-2-{(1S)-2-methyl-1-[(methylcarboxamido)propyl] carboxamido}butanediamide (43);

N1-(1-ethyl-3,3,3-trifluoro-2-oxopropyl)-(2S)-2-[((1S)-2-methyl-1-[(1S)-2-methyl-1-(methylcarboxamido) propyl] carboxamidopropyl)carboxamido] butanediamide (44) [SEQ ID NOS: 7 & 8];

N1-(1-(3,3,3,-trifluoro-1-propyl-2-oxopropyl)-(2S)-2-[((1S)-2-methyl-1-[(1S)-2-methyl-1-(methylcarboxamido)propyl]carboxamidopropyl) carboxamido]butane diamide (45) [SEQ ID NOS: 9 & 10];

N1-(3,3,3-trifluoro-1-methyl-2-oxopropyl)-(2S)-2-[((1S)-2-methyl-1-[(1S)-2-methyl-1-(methylcarboxamido)propyl]carboxamidopropyl) carboxamido]pentanediamide (46) [SEQ ID NOS: 11 & 12];

(3S)-3-[((1S)-2-methyl-1-[(1S)-2-methyl-1-(methylcarboxamido)propyl]carboxamidopropyl) carboxamido]-3-[(3,3,3-trifluoro-1-methyl-2-oxopropyl)carbamoyl]propanoic acid (47) [SEQ ID NOS: 13 & 14];

N1-[(1S)-1-((1S)-2-hydroxy-1-[(3,3,3-trifluoro-1-methyl-2-oxopropyl)carbamoyl]ethyl-carbamoyl)-2-methylpropyl]-(2S)-3-methyl-2-(methylcarboxamido) butanamide (48) [SEQ ID 15 & 16];

N1-(3,3,3-trifluoro-1-methyl-2-oxopropyl)-(2S)-6-amino-2-[((1S)-2-methyl-1-[(1S)-2-methyl-1-(methylcarboxamido)propyl]carboxamidopropyl) carboxamido]hexanamide (49) [SEQ ID NOS: 17 & 18];

N1-[(1S)-2-methyl-1-((1S)-2-(1,3-thiazol-4-yl)-1-[(3,3,3-trifluoro-1-methyl-2-oxopropyl)-carbamoyl] ethylcarbamoyl)propyl]-(2S)-3-methyl-2-(methylcarboxamido)butanamide (50) [SEQ ID NOS: 19 & 20];

N4,N4-dimethyl-N1-(3,3,3-trifluoro-1-methyl-2-oxopropyl)-(2S)-2-[((1S)-2-methyl-1-[(1S)-2-methyl-1-(methylcarboxamido)propyl]carboxamidopropyl) carboxamido]butanediamide (51) [SEQ ID NOS: 21 & 22];

N1-(3,3,3-trifluoro-1-methyl-2-oxopropyl)-(2S)-4-methyl-2-[((1S)-2-methyl-1-[(1S)-2-methyl-1-(methylcarboxamido)propyl]carboxamidopropyl) carboxamido]pentanamide (52) [SEQ ID NOS: 23 & 24];

N1-[(1S)-2-methyl-1-((1S)-2-phenyl-1-[(3,3,3-trifluoro-1-methyl-2-oxopropyl)carbamoyl]-ethylcarbamoyl) propyl]-(2S)-3-methyl-2-(methylcarboxamido) butanamide (53) [SEQ ID NOS: 25 & 26];

N1-[(1S)-2-methyl-1-((1S)-2-methyl-1-[(3,3,3-trifluoro-1-methyl-2-oxopropyl)carbamoyl]-propylcarbamoyl) propyl]-(2S)-3-methyl-2-(methylcarboxamido) butanamide (54) [SEQ ID NOS: 27 & 28];

N1-[(1S)-2-methyl-1-((1S)-1-[(3,3,3-trifluoro-1-methyl-2-oxopropyl)carbamoyl]ethyl-carbamoyl)propyl]-(2S)-3-methyl-2-(methylcarboxamido)butanamide (55) [SEQ ID NOS: 29 & 30];

N1-[(1S)-2-methyl-1-((1R)-1-[(3,3,3-trifluoro-1-methyl-2-oxopropyl)carbamoyl]ethyl-carbamoyl)propyl]-(2S)-3-methyl-2-(methylcarboxamido)butanamide (56) [SEQ ID NOS: 31 & 32];

N4,N4-dimethyl-N1-(3,3,3-trifluoro-1-methyl-2-oxopropyl)-(2S)-2-[((1S)-[(1S)-2-methyl-1-(methylcarboxamido)propyl]carboxamidopropyl) carboxamido]butanediamide (57) [SEQ ID NOS: 33 & 34];

N4,N4-dimethyl-N1-(3,3,3-trifluoro-1-methyl-2-oxopropyl)-(2S)-2-[((1S)-2,2-dimethyl-1-[(1S)-2-methyl-1-(methylcarboxamido)propyl] carboxamidopropyl)carboxamido]butanediamide (58) [SEQ ID NOS: 35 & 36];

N4,N4-dimethyl-N1-(3,3,3-trifluoro-1-methyl-2-oxopropyl)-(2S)-2-[((1S)-3,3-dimethyl-1-[(1S)-2-methyl-1-(methylcarboxamido)propyl]carboxamido butyl)carboxamido]butanediamide (59) [SEQ ID NOS: 37 & 38];

N4,N4-dimethyl-N1-(3,3,3-trifluoro-1-methyl-2-oxopropyl)-(2S)-2-[((S)-1-(1-adamantyl)-1-[(1S)-2-methyl-1-(methylcarboxamido)propyl]carboxamido methyl)carboxamido]butanediamide (60) [SEQ ID NOS: 39 & 40];

(3S)-3-((1S)-2-(dimethylcarbamoyl)-1-[(3,3,3-trifluoro-1-methyl-2-oxopropyl)carbamoyl]-ethylcarbamoyl)-2,2-dimethyl-3-[(1S)-2-methyl-1-(methylcarboxamido) propyl]carboxamidopropanoic acid (61) [SEQ ID NOS: 41 & 42];

N4,N4-dimethyl-N1-(3,3,3-trifluoro-1-methyl-2-oxopropyl)-(2S)-2-[(1S)-2,2-dimethyl-1-(methylcarboxamido)propyl] carboxamidobutanediamide (62);

N4,N4-dimethyl-N1-(3,3,3-trifluoro-1-methyl-2-oxopropyl)-(2S)-2-((1S)-1-[(4-hydroxyphenethyl)carboxamido]-2,2-dimethylpropylcarboxamido)butanediamide (63);

N4,N4-dimethyl-N1-(3,3,3-trifluoro-1-methyl-2-oxopropyl)-(2S)-2-[(1S)-1-(isobutylcarboxamido)-2,2-dimethylpropyl]carboxamidobutanediamide (64);

N4,N4-dimethyl-N1-(3,3,3-trifluoro-1-methyl-2-oxopropyl)-(2S)-2-[(1S)-2,2-dimethyl-1-(neopentylcarboxamido)propyl]carboxamidobutanediamide (65);

N4,N4-dimethyl-N1-(3,3,3-trifluoro-1-methyl-2-oxopropyl)-(2S)-2-((1S)-1-[(3,3-dimethyl-butyl)amino]-2,2-dimethylpropylcarboxamido]butanediamide (66);

4N,4N-Dimethyl-1N-(3,3,3-trifluoro-1-methyl-2-oxopropyl)-2-[1-(tert-butoxycarbonyl-amino)-2,2-dimethyl-(1S)-propylcarboxamido]-(2S)-butanediamide (67);

N4,N4-Dimethyl-N1-(3,3,3-trifluoro-1-methyl-2-xopropyl-2-[1-(tert-butylaminocarbonyl-amino)-2,2-imethyl-(1S)-propylcarboxamido]-(2S)-butanediamide 68);

4,N4-dimethyl-N1-(3,3,3-trifluoro-1-methyl-2-xopropyl)-(2S)-2-[((1S)-1-[(dimethylmino)methyl]carboxamido-2,2-dimethylpropyl) carboxamido]butanediamide (69) [SEQ ID NOS: 43 & 44];

4-[(1S)-1-((1S)-2-(dimethylcarbamoyl)-1-[(3,3,3-rifluoro-1-methyl-2-oxopropyl)carbamoyl]ethylcarbamoyl)-2,2-dimethylpropyl]carbamoylbutanoic cid (70);

N4,N4-dimethyl-N1-(3,3,4,4,4-pentafluoro-1-methyl-2-oxobutyl)-(2S)-2-[(1S)-2,2-dimethyl-1-(neopentyl carboxamido)propyl]carboxamidobutanediamide (74);

N1-[3-(benzylcarbamoyl)-3,3-difluoro-1-methyl-2-oxopropyl]-N4,N4-dimethyl-(2S)-2-[(1S)-2,2-dimethyl-1-(neopentylcarboxamido)propyl]carboxamidobutanediamide (75);

3-{2-[2-(3,3-dimethyl-butyrylamino)-3,3-dimethyl-butyrylamino]-3-dimethylcarbamoyl-propionylamino}-2-oxo-butyric acid benzyl amide (76);

N1-[2-(1,3-benzoxazol-2-yl)-1-methyl-2-oxoethyl]-N4,N4-dimethyl-(2S)-2-{[(1S)-2,2-dimethyl-1-(neopentylcarboxamido)propyl]carboxamido}butanediamide (77);

Diphenyl N4,N4-dimethyl-N1-(1-aminoethylphosphinate)(2S)-2-{[(1S)-2,2-dimethyl-1-(neopentylcarboxamido)propyl]carboxamido}butanediamide (79);.

N1-[2-(1,3-benzothiazol-2-yl)-1-methyl-2-oxoethyl]-N4,N4-dimethyl-(2S)-2-{[(1S)-2,2-di-methyl-1-(neopentylcarboxamido)propyl]carboxamidolbutanediamide (80);

N4,N4-dimethyl-N1-(1-methyl-2-[1,3]oxazolo[4,5-b]pyridin-2-yl-2-oxoethyl)-(2S)-2-{[(1S)-2,2-dimethyl-1-(neopentylcarboxamido)propyl]carboxamido}butanediamide (81);

N4,N4-dimethyl-N1-[1-methyl-2-(6-methyl-1,3-benzoxazol-2-yl)-2-oxoethyl]-(2S)-2-{[(1S)-2,2-dimethyl-1-(neopentylcarboxamido)propyl]carboxamido}butanediamide (82);

N4,N4-dimethyl-N1-[1-methyl-2-(5-methyl-1,3-benzoxazol-2-yl)-2-oxoethyl]-(2S)-2-{[(1S)-2,2-dimethyl-1-(neopentylcarboxamido)propyl]carboxamido}butanediamide (83);

N4,N4-dimethyl-N1-[1-methyl-2-(4-methyl-1,3-benzoxazol-2-yl)-2-oxoethyl]-(2S)-2-{[(1S)-2,2-dimethyl-1-(neopentylcarboxamido)propyl]carboxamido}butanediamide (84);

N4,N4-dimethyl-N1-[1-methyl-2-(7-methyl-1,3-benzoxazol-2-yl)-2-oxoethyl]-(2S)-2-{[(1S)-2,2-dimethyl-1-(neopentylcarboxamido)propyl]carboxamido}butanediamide (85);

N4,N4-dimethyl-N1-[1-methyl-2-(methylcarbamoyl)-2-oxoethyl]-(2S)-2-1[(1S)-2,2-dimethyl-1-(neopentylcarboxamido)propyl]carboxamido}butanediamide (86);

N1-(2-[2-(benzyloxy)ethyl]carbamoyl-1-methyl-2-oxoethyl)-N4,N4-dimethyl-(2S)-2-{[(1S)-2,2-dimethyl-1-(neopentylcarboxamido)propyl]carboxamido}butanediamide (88);

N1-2-[(1,3-benzodioxol-5-ylmethyl)carbamoyl]-1-methyl-2-oxoethyl-N4,N4-dimethyl-(2S)-2-{[(1S)-2,2-dimethyl-1-(neopentylcarboxamido)propyl]carboxamido}butanediamide (89);

N1-2-[(1H-benzo[d]imidazol-2-ylmethyl)carbamoyl]-1-methyl-2-oxoethyl-N4,N4-dimethyl-(2S)-2-{[(1S)-2,2-dimethyl-1-(neopentylcarboxamido)propyl]carboxamido} butanediamide (90);

N4,N4-dimethyl-N1-(1-methyl-2-oxo-2-[(1S)-1-phenylethyl]carbamoylethyl)-(2S)-2-{[(1S)-2,2-dimethyl-1-(neopentylcarboxamido)propyl]carboxamido} butanediamide (91);

N4,N4-dimethyl-N1-(1-methyl-2-oxo-2-[(1R)-1-phenylethyl]carbamoylethyl)-(2S)-2-{[(1S)-2,2-dimethyl-1-(neopentylcarboxamido)propyl]carboxamido} butanediamide (92);

N4,N4-dimethyl-N1-(1-methyl-2-oxo-2-[(1R)-1-phenylpropyl]carbamoyl-ethyl)-(2S)-2-{[(1S)-2,2-dimethyl-1-(neopentylcarboxamido)propyl]carboxamido} butanediamide (93);

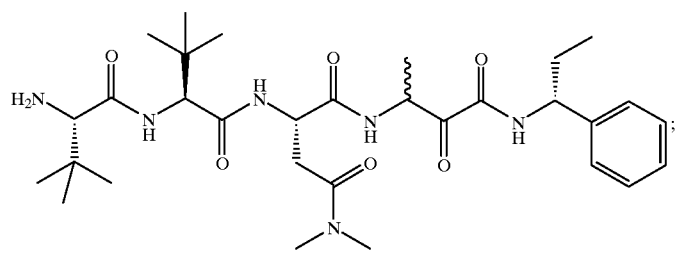

[SEQ ID NOS: 45 & 46]

95
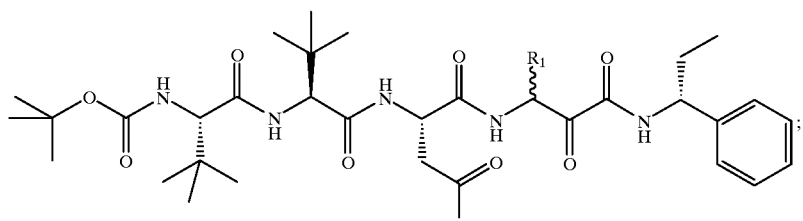
[SEQ ID NOS: 47 & 48]
96
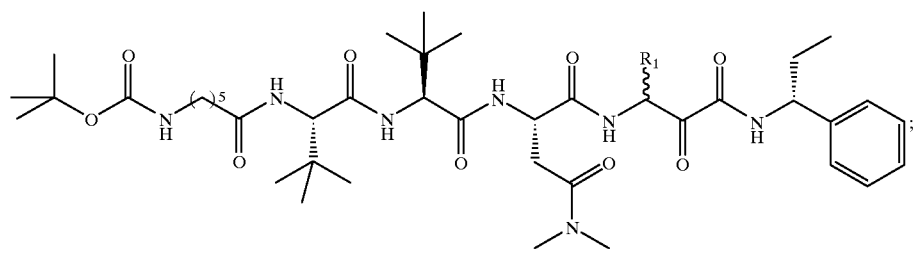
[SEQ ID NOS: 49 & 50]
97
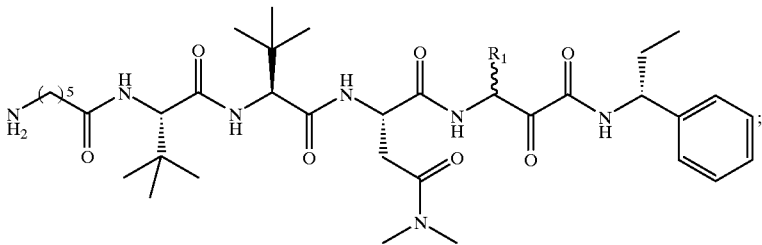
[SEQ ID NOS: 51 & 52]
98
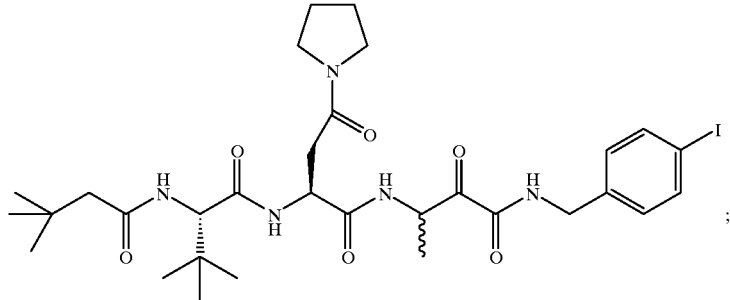
Ac-Ser-Tyr-Val-Lys-Ala(d,1)—C(O)—NH—CH₂—Ph
218 [SEQ ID NOS: 71 & 72];
301
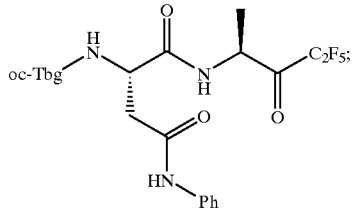
302
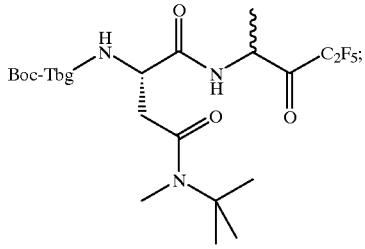

303
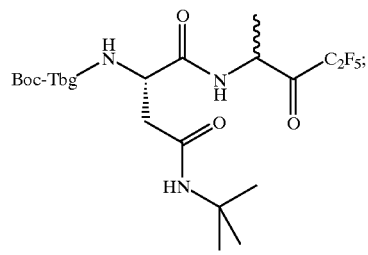
304
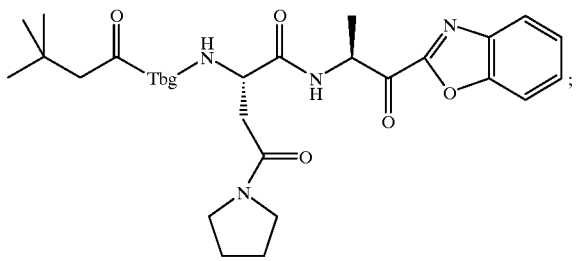
305
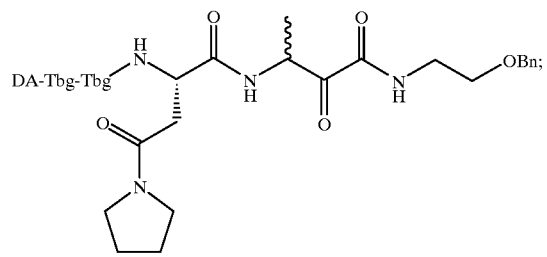
306
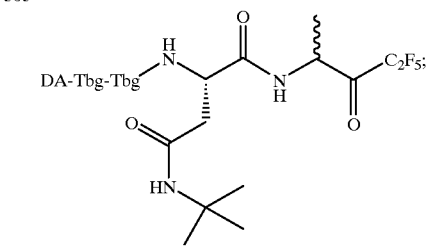
307
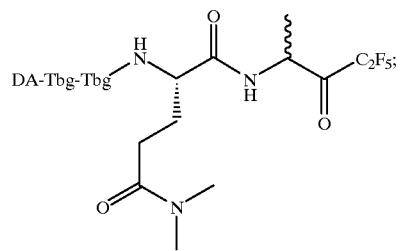
308
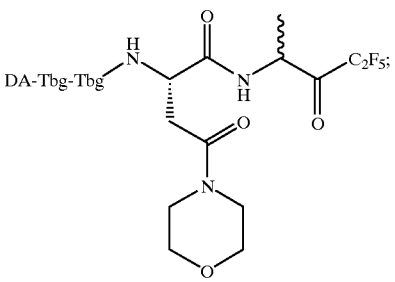
309
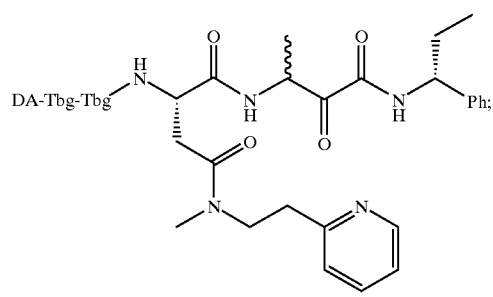
310
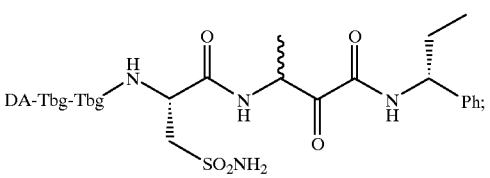
311
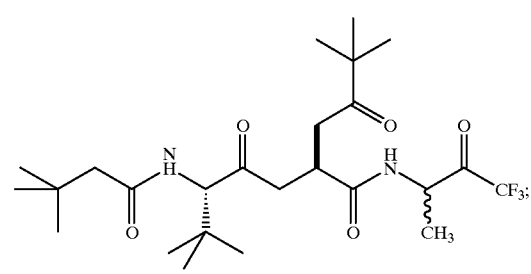
312
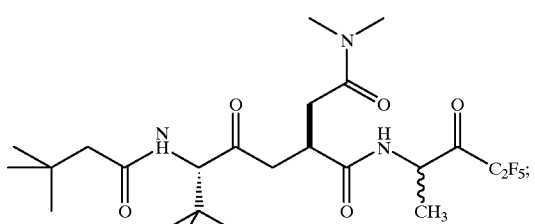

-continued
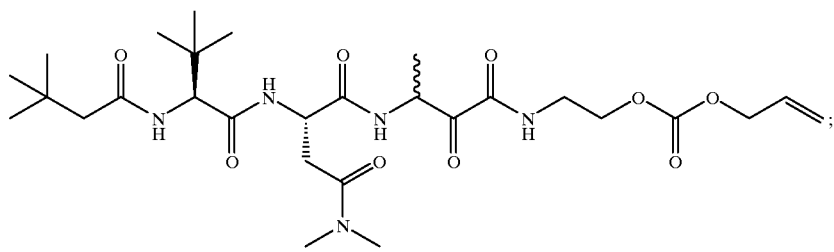
401
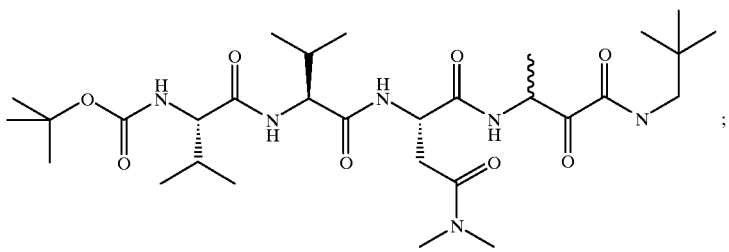
[SEQ ID NOS: 53 & 54]
402
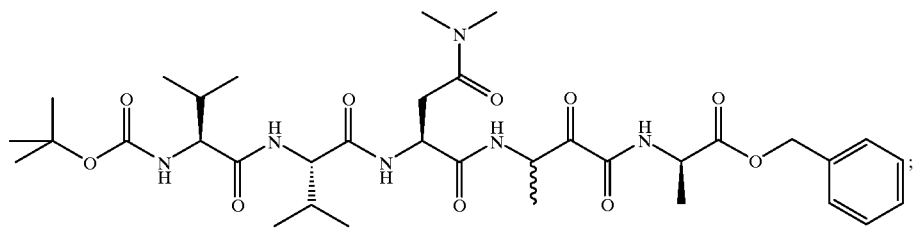
[SEQ ID NOS: 55 & 56]
403
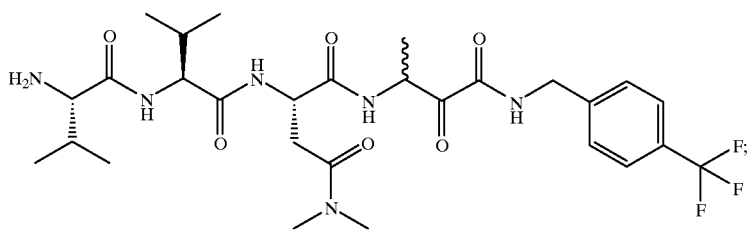
[SEQ ID NOS: 57 & 58]
404
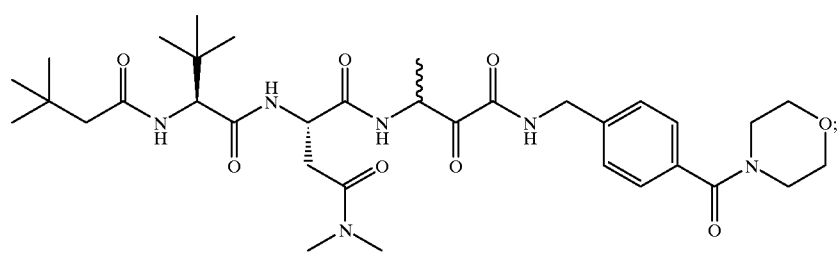
405
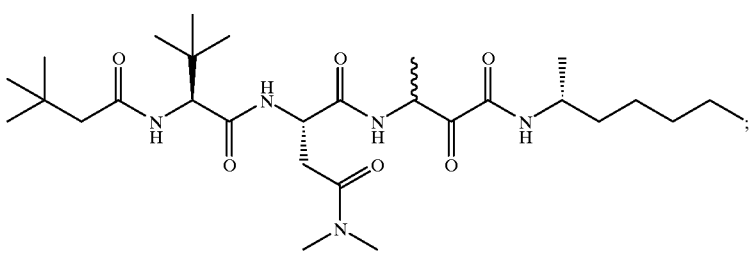
406

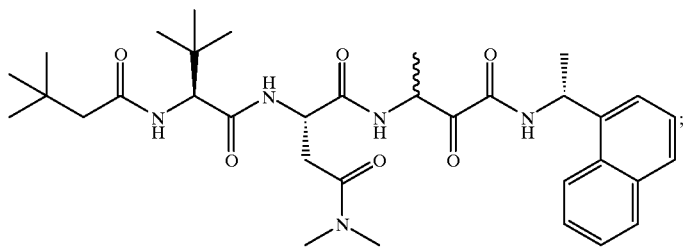
407
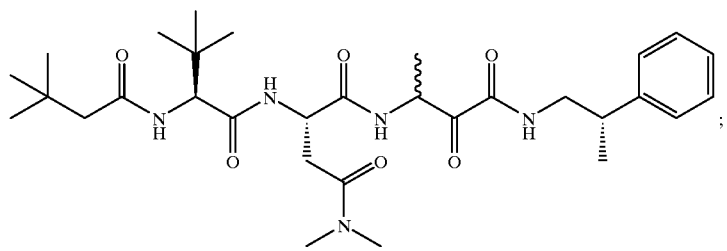
408
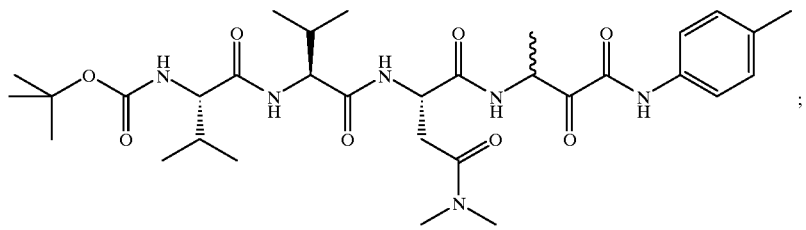
[SEQ ID NOS: 59 & 60]
409
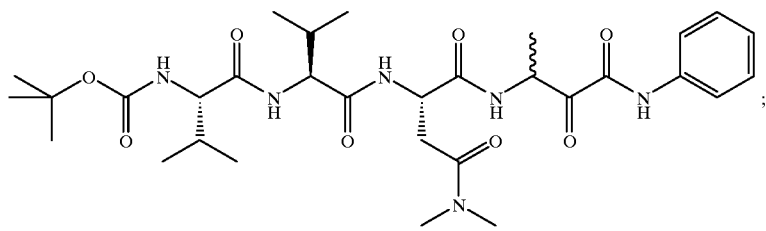
[SEQ ID NOS: 61 & 62]
410
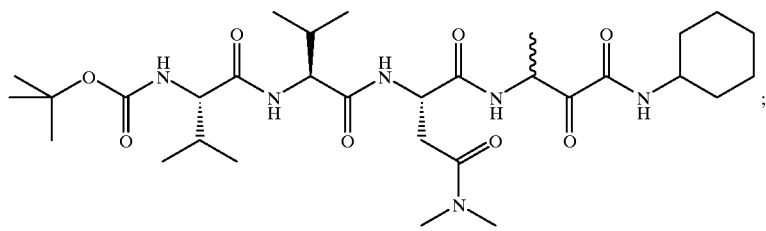
[SEQ ID NOS: 63 & 64]
411
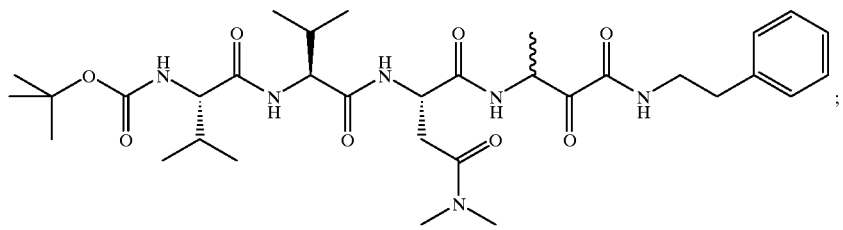
[SEQ ID NOS: 65 & 66]
412

-continued

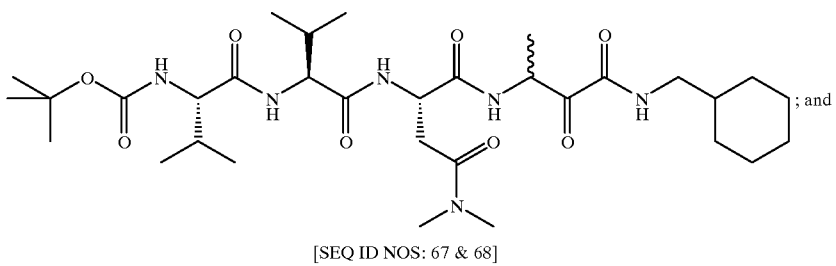

[SEQ ID NOS: 67 & 68]

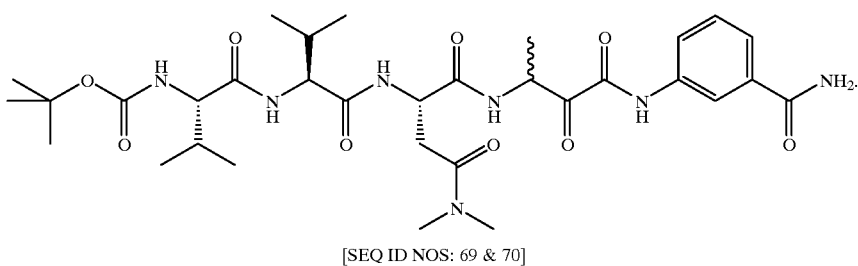

[SEQ ID NOS: 69 & 70]

A further aspect of the present invention is a solid phase process for the synthesis of peptidyl activated ketones comprising the steps of:
a) coupling a semicarbazone acid of formula 113 to a resin by in situ activation;

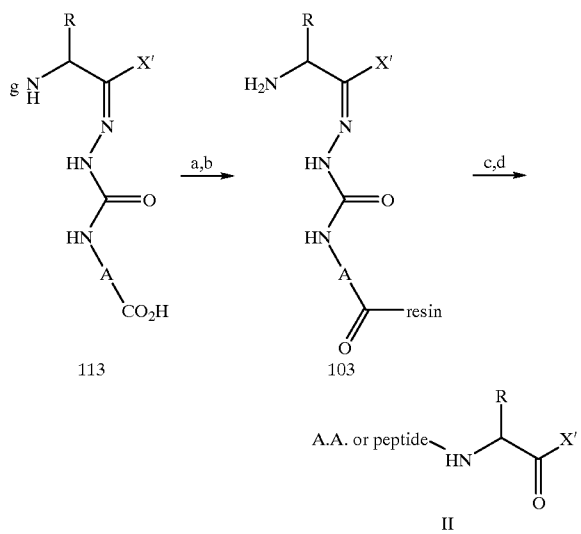

wherein R is a side chain of a natural or non-natural amino acid;
and X' is $CF_3$, $CF_2CONH$—$R_{30}$, $C(O)NH$—$R_{30}$, or $C(O)OR_{30}$, wherein $R_{30}$ is a cyclic $C_{3-12}$ alkyl or acyclic $C_{1-10}$ alkyl or cyclic $C_{3-12}$ alkenyl or acyclic $C_{2-12}$ alkenyl, said alkyl or alkenyl optionally substituted with $NH_2$, OH, SH, halo, or carboxyl;
said alkyl or alkenyl optionally containing at least one heteroatom independently selected from the group consisting of: O, S, and N; or $R_{30}$ is a $C_6$ or $C_{10}$ aryl or $C_{7-16}$ aralkyl optionally substituted with $C_{1-6}$ alkyl, $NH_2$, OH, SH, halo, carboxyl or carboxy(lower)alkyl; said aryl or aralkyl optionally containing at least one heteroatom independently selected from the group consisting of: O, S, and N;

A is a divalent spacer group which comprises a non-reactive divalent hydrocarbyl group having from 2 to 15 carbon atoms;
and
Pg is an amino protecting group
b) deprotecting said amino protecting group to give the desired resin of formula 103;
c) coupling said resin with one or more amino acid in a sequential manner by standard chemistry; and
d) cleaving said peptide from said resin to obtain a peptidyl activated ketone of formula II. Preferably, the cleavage step as herein described is carried out in THF, aq.HCl, and AcOH at a temperature of about 60° C. for about 4 hours; and said resin is filtered at least once.

Preferably, the resin is selected from the group consisting of: polystyrene or pegylated polystyrene functionalized with benzydrylamine (BHA); 4-methyl benzydrylamine (MBHA); and aminomethyl (AM).

Preferably, the in situ activation is carried out with the addition of a coupling agent selected from the group consisting of: 2-(1H-benzotriazol-1-yl)-1,1,3,3-tetramethyluronium tetrafluoroborate (TBTU); 2-(1H-benzotriazol-1-yl)-1,1,3,3-tetramethyluronium hexafluorophosphate (HBTU); diisopropyl carbodiimide (DIC), and dicyclohexyl carbodiimide (DCC).

Preferably, the amino protecting group is selected from the group consisting of: t-butyloxycarbonyl (Boc); 9-fluorenylmethyloxy carbonyl (Fmoc); and allyloxy carbonyl (Alloc).

Preferably, X' is $C(O)NH_2CH_2$-phenyl or $C(O)OCH_2CH$=$CH_2$.

Preferably, R is selected from the group consisting of: $CH_3$; $CH_2CH_3$; $CH_2CH_2CH_3$; $(CH_2)_4NH_2$; $CH(CH_3)2$; $CH_2$-phenyl; $(CH_2)_3$—NH—CH=N ($NH_2$).

Preferably, A is cyclohexyl, phenyl or benzyl.

Alternatively, a further aspect of the present invention is a resin of formula 103 as defined above.

Still, a further aspect of the present invention is the use of a resin of formula 103 for the solid phase synthesis of peptidyl activated ketones.

DETAILED DESCRIPTION OF THE INVENTION

Figure 1:
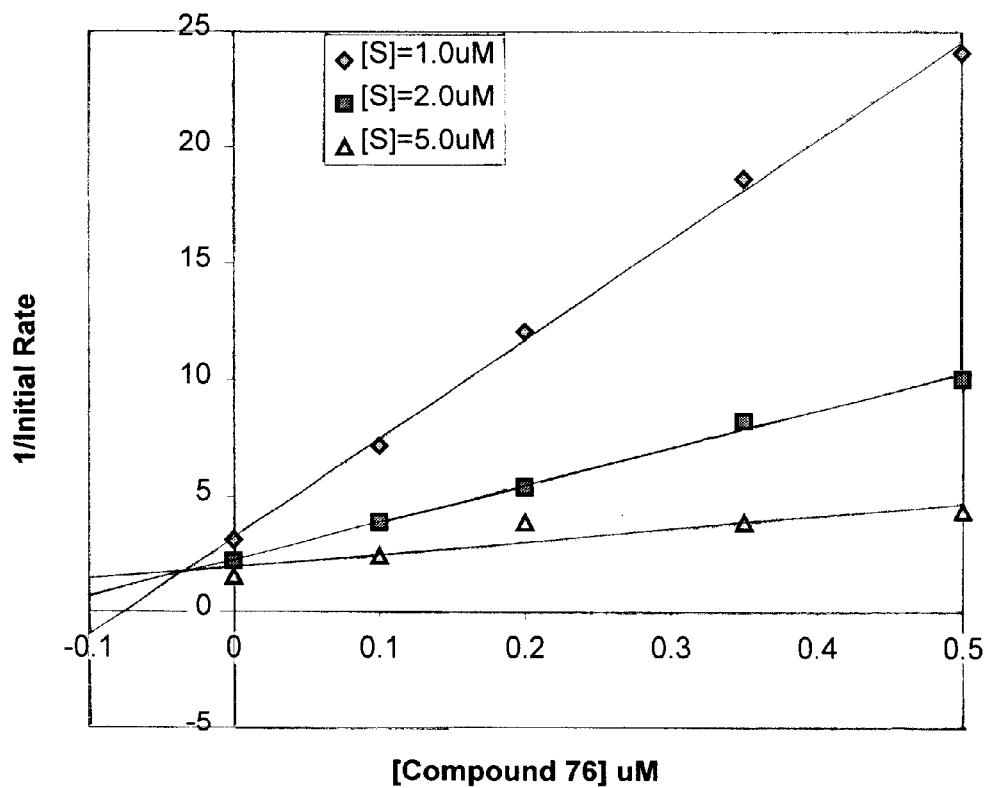
FIG. 1 is a Dixon plot for competitive inhibition of compound 76 against HCMV protease.

As used herein, the following definitions apply unless otherwise noted:

With reference to the instances where (R) or (S) is used to designate the configuration of a radical, e.g. $R_4$ of the compound of formula I, the designation is done in the context of the compound and not in the context of the radical alone.

The natural amino acids, with exception of glycine, contain a chiral carbon atom. Unless otherwise specifically indicated, the compounds containing natural amino acids with the L-configuration are preferred. However, applicants contemplate that when specified, some amino acids of the formula I can be of either D- or L-configuration or can be mixtures of D- and L-isomers, including 1:1 epimeric mixtures.

The non-natural amino acids include, but are not limited to, α-aminoadipic acid, α-γ-diamino butyric acid, ornithine, pipecolic acid, sarcosine, thyroxine, hydroxylysine, and hydroxyproline.

The abbreviations for some α-amino acids are set forth in Table A.

TABLE A

| AMINO ACID | SYMBOL |
| --- | --- |
| Aminobutyric acid | Abu |
| Alanine | Ala |
| Arginine | Arg |
| Aspartic acid | Asp |
| Asparagine | Asn |
| Cysteine | Cys |
| Glutamic acid | Glu |
| Glutamine | Gln |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| tert-Butylglycine | Tbg |
| Desamino-tert-butylglycine | DA-Tbg |
| Tyrosine | Tyr |
| Valine | Val |

As used herein the term "tert-butylglycine" refers to a compound of formula:

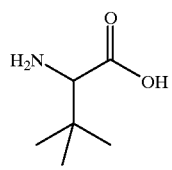

The term "side chain" with reference to an amino acid or amino acid derivative means a residue attached to the α-carbon atom of the α-amino acid. For example, the R-group side chain for glycine is hydrogen, for alanine it is methyl, for asparagine it is $CH_2-C(O)NH_2$, for glutamine it is $CH_2CH_2C(O)NH_2$, and tert-butylglycine it is tert-butyl. For the specific R-groups or side chains of the α-amino acids reference is made to A. L. Lehninger's text on Biochemistry (see chapter 4).

The term "halo" as used herein means a halogen radical selected from bromo, chloro, fluoro or iodo.

The term "$C_{1-10}$ alkyl" or "(lower)alkyl" as used herein, either alone or in combination with another radical, means cyclic or acyclic (meaning straight chain or branched) alkyl radicals containing up to ten carbon atoms and includes, for example, methyl, ethyl, propyl, butyl, hexyl, 1-methylethyl, 1-methylpropyl, 2-methylpropyl, 1,1-dimethylethyl. Obviously, as will be readily recognized by a person skilled in the art when a cycloalkyl is contemplated, unless otherwise indicated, the alkyl radical will contain at least 3 carbon atoms.

The term "C2-10 alkenyl" as used herein, either alone or in combination with another radical, means an alkyl radical as defined above containing from 2 to 10 carbon atoms, and further containing at least one double bond. For example alkenyl includes allyl.

The term "$C_6$ or $C_{10}$ aryl" as used herein, either alone or in combination with another radical, means either an aromatic monocyclic system containing 6 carbon atoms or an aromatic bicyclic system containing 10 carbon atoms. For example, aryl includes phenyl or naphthalene.

The term "$C_{7-16}$ aralkyl" as used herein, either alone or in combination with another radical, means an aryl as defined above linked through an alkyl group, wherein alkyl is as defined above containing from 1 to 6 carbon atoms. Aralkyl includes for example benzyl, and butylphenyl.

The term "divalent spacer group" as used herein means a non-reactive divalent hydrocarbyl group from 2 to 15 carbon atoms and includes, but is not limited to, cyclohexane, phenyl and benzyl.

The term "heterocycle" as used herein, either alone or in combination with another radical, means a monovalent radical derived by removal of a hydrogen from a five-, six-, or seven-membered saturated or unsaturated heterocycle containing from one to four heteroatoms selected from nitrogen, oxygen and sulfur. Examples of suitable heterocycles include pyrrolidine, pyridine, thiazole, thiazolidine, benzothiazole, benzoxazole, benzimidazole, and 3,4-methylenedioxybenzene.

ANTIVIRAL ACTIVITY

The antiviral activity of the aforementioned peptidomimetic inhibitors of HCMV protease (HCMV protease inhibitors) can be demonstrated by biochemical, microbiological and biological procedures. For example, an assay based on the evaluation of the ability of the test compound to inhibit HCMV protease, an enzyme vital for viral replication.

When the HCMV protease inhibitor is employed as an antiviral agent, it is administered orally, or systemically to humans in a vehicle comprising one or more pharmaceutically acceptable carriers, the proportion of which is determined by the solubility and chemical nature of the compound, chosen route of administration and standard biological practice. For oral administration, the compound or a therapeutically acceptable salt thereof can be formulated in unit dosage forms such as capsules or tablets each containing a predetermined amount of the active ingredient, ranging from about 50 to 500 mg, in a pharmaceutically acceptable carrier.

For parenteral administration, the HCMV protease inhibitor is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's The Science and Practice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the HCMV protease inhibitor will vary with the form of administration and the particular active agent chosen. Furthermore, it will vary with the particular host under treatment. Generally, treatment is initiated with small increments until the optimum effect under the circumstance is reached. In general, the inhibitor compound is most desirably administered at a concentration level that will generally afford antivirally effective results without causing any harmful or deleterious side effects. For oral administration, the HCMV protease inhibitor is administered in the range of 20 to 200 mg per kilogram of body weight per day, with a preferred range of 25 to 100 mg per kilogram.

For ocular administration, the HCMV protease inhibitor is administered either topically or intraocularly (injection or implant) in a suitable preparation. For example, an implant containing the compound in a suitable formulation can be surgically placed in the posterior segment of the eye through a small incision.

With reference to systemic administration, the HCMV protease inhibitor is administered at a dosage of 10 mg to 150 mg per kilogram of body weight per day, although the aforementioned variations will occur. However, a dosage level that is in the range of from about 10 mg to 100 mg per kilogram of body weight per day is most desirably employed in order to achieve effective results.

CHEMISTRY

The synthesis of the various inhibitors and the required intermediates are described in Schemes 2 to 7.

Inhibitors containing a trifluoromethyl ketone function were obtained in one of three ways: solution chemistry or solid phase synthesis: schemes 2 or 3. Inhibitors containing an α-ketoamide were obtained in one of two ways: solid phase: scheme 3 or solution chemistry: scheme 4. Inhibitors containing other activated ketones were obtained by solution chemistry: scheme 5.

Solid Phase Synthesis.

Scheme 2:

Inhibitors which incorporate an asparagine residue at $P_2$ (Scheme 2) could be prepared through solid phase synthesis using the asparagine side chain as an attachment point to the resin (Abraham, N. A.; Fazal, G.; Ferland, J.-M.; Rakhit, S.; Gauthier, J., A new solid phase strategy for the synthesis of mammalian glucagon, *Tetrahedron Lett.* 1991, 32, 577–580).

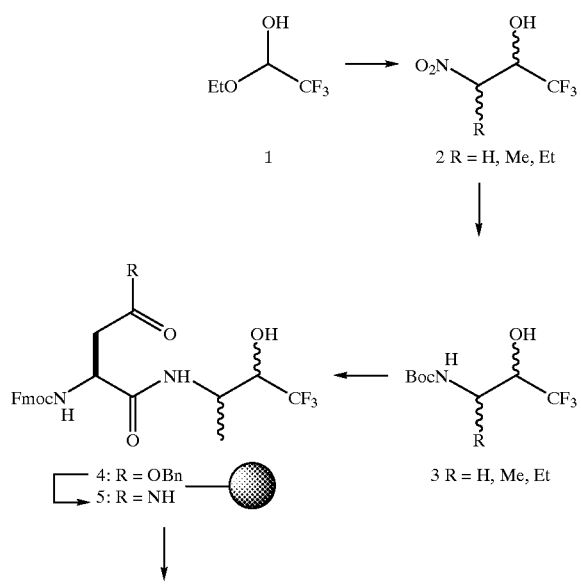

-continued

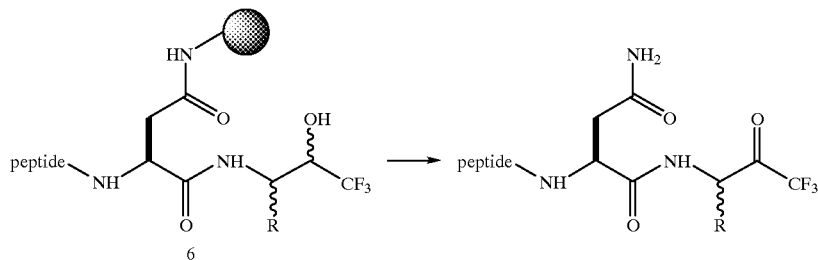

Thus a Henry reaction between hemiacetal 1 and nitroethane gave nitro alcohol 2 which was immediately reduced and protected to yield alcohol 3. After removal of the Boc group, coupling with a suitably protected aspartic acid derivative gave 4. This compound was then deprotected by hydrolysis and incorporated onto a polymer support to afford the derivatized amide resin 5. The required amino acids were then introduced by standard methods. Hydrolysis from the resin and oxidation of the resulting alcohol using Moffatt's procedure [(a) Pfitzner, K. E.; Moffatt, J. G. Sulfoxide-carbodiimide reactions. I. A facile oxidation of alcohols. *J. Am. Chem. Soc.* 1965, 87, 5661–5670. (b) Pfitzner, K. E.; Moffatt, J. G. Sulfoxide-carbodiimide reactions. II. Scope of the oxidation reaction. *J. Am. Chem. Soc.* 1965, 87, 5670–5678] gave the desired peptides. Activated ketones which contain a $P_2$ residue other than asparagine were prepared using standard solution methods from alcohol 3 or by the novel solid phase technique described below.

Schemes 3A and 3B:

The synthesis of peptidyl trifluoromethyl ketone or α-ketoamide is typically performed in solution, by preparing a precursor alcohol and submitting it to a final oxidation step. This oxidation is often problematic (especially when other oxidizable groups are present in the molecule) and sometimes limits the choice of pharmacophore to be incorporated in the inhibitor.

To take advantage of the recent advances in robotics technologies and in the development of combinatorial chemistry techniques, we sought to investigate a solid phase process for the synthesis of peptidyl trifluoromethyl ketone or α-ketoamide inhibitors. Our goal was to develop a methodology which would give access directly to the activated ketone functionality without the need to perform a final oxidation step. To this end, we considered using a semicarbazone linkage 103 (Scheme 3A) to serve both as reversible protecting group for the ketone and as anchoring group to the polymeric support. A similar solid phase process had already been reported by Webb and co-workers for the preparation of peptidyl aldehydes (a) Murphy, A. M.; Dagnino, R.; Pureza Jr., L. V.; Trippe, A. J.; Sherman, S. L.; Lumpkin, R. H.; Tamura, S. Y.; Webb, T. R. *J. Am. Chem. Soc.* 1992, 114, 3156;b) Webb, T. R. U.S. Pat. No. 5,283, 293; c) Webb, T. R. U.S. Pat. No. 5,367,072). Our process, however, comprises a final cleavage step that is performed without the requirement of formaldehyde as is described in the process of Webb et al. This allows for a greater variety of pharmacophores to be incorporated in the inhibitor.

The precursor for α-ketoamides (108) was prepared as follows:

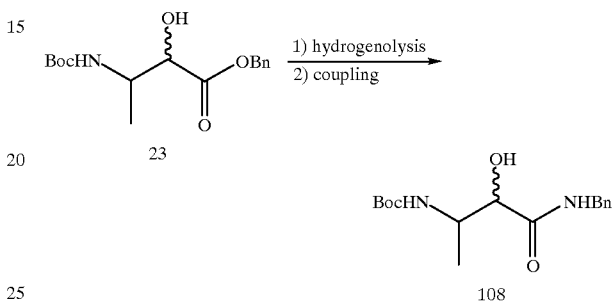

Scheme 3A

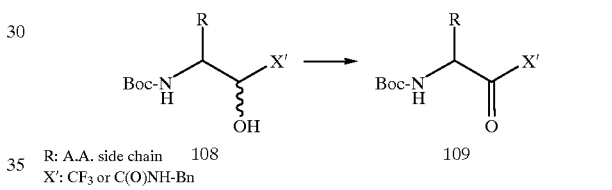

R: A.A. side chain    108
X': $CF_3$ or C(O)NH-Bn                    109

Oxalyl chloride, $DMSO/CH_2Cl_2$ then $Et_3N$, -78° C. to 0° C.

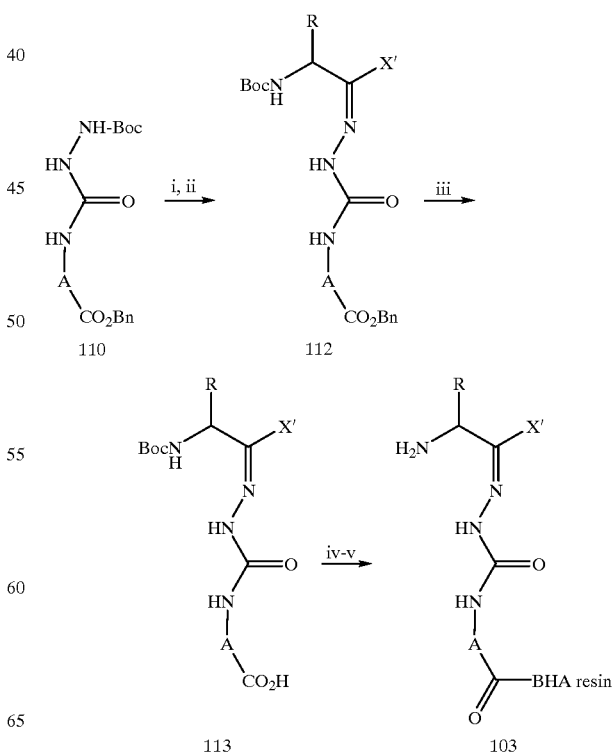

-continued i) 4 M HCl/Dioxane then aq. K$_2$CO$_3$ (94%); ii) 5 a–c, p-TsOH (cat.), Toluene Reflux;
iii) Pd/C, H$_2$(40 psi)/MeOH—EtOAc; iv) BHA resin, TBTU, HOBt, DIPEA/DMSO;
v) 45% TFA/CH$_2$Cl$_2$ then 5% DIPEA/CH$_2$Cl$_2$
A: divalent spacer group such as cyclohexyl; phenyl or benzyl The trifluoromethyl ketone or α-ketoamide (108) were oxidized by a Swern oxidation to give the corresponding trifluoromethyl ketone and α-ketoamide in 66% yields.

With the necessary activated ketone in hand, it remained to generate the desired semicarbazone moiety 112 and to anchor it onto a BHA resin. To this end, the protected semicarbazide 110 was deprotected and neutralized. The resulting semicarbazide was then condensed in refluxing toluene, with the activated ketone 109 under acid catalysis and azeotropic removal of water, to give the trans semicarbazone 112 in moderate yield (in the case of the ketoamide, a cis/trans mixture was obtained). The hydrogenolysis of the benzyl ester proceeded without problem to give the corresponding acid 113 in quantitative yield. The acid was then coupled to a polystyrene BHA resin by in situ activation with TBTU followed by the removal of the Boc protecting group to give the desired resin 103.

With the resin 103 in hand, the solid-phase oligomerizaton was accomplished using standard protocols. The semicarbazone linkage being resistant to both anhydrous acidic and mildly basic conditions, both Boc and Fmoc-protected amino acids could be used at any position of the peptidic sequence. This versatility allowed for an increased diversity in building blocks to be incorporated in the final inhibitor. The coupling of amino acids was done through their corresponding HOBt esters as shown in Scheme 3B. At the completion of the synthesis, in cases where the molecule incorporated acid-sensitive side chain protecting groups, those were removed by treatment with 75% TFA/CH$_2$Cl$_2$.

The final cleavage from the polymer support was performed by refluxing the dried resin in a THF solution containing aqueous HCl and acetic acid at 65° C. In order to maximize the yields, we found it necessary to filter the resin and repeat this protocol once more. In general, the cleavage from the resin was slightly slower for the valine-derived trifluoromethyl ketones 212–217 (see Example 62) than for their alanine (201–207) or ethyl glycine (208–211) counterpart. This difference in rate of hydrolysis could be compensated for by doing one extra cleavage for valine derivatives. In cases where a basic residue was present in the sequence, a slightly higher concentration of HCl was used during the cleavage and a total of three cleavages were required in order to ensure maximum yields. We have found that addition of formaldehyde to trap the liberated semicarbazide to be superfluous. Not only the formaldehyde did not provide any significant benefit as reflected by the overall yield of compound, but it did also complicate the isolation of the desired product, particularly for sequences containing a free amino group.

During the final cleavage, no interference was observed from nucleophilic or oxidizable side chains such as the ones present in serine, methionine, tyrosine, histidine, lysine or aspartic acid. The cleavage of inhibitors containing an asparagine residues adjacent to the trifluoromethyl group was more problematic. In this case, it was found necessary to use the N-trityl protected asparagine and to deprotect the trityl group in solution after the cleavage from the resin. The presence of an asparagine residue elsewhere in the sequence did not however necessitate any side chain protection.

The cleavage conditions were mild enough to be compatible with various acid-sensitive protecting groups such as N-Boc, O-t-Bu ether, O-t-Bu ester and O-Bn ester. During the cleavage, methyl esters are however hydrolyzed to an extent of 50%. In most cases, the treatment with 75% TFA prior to the cleavage from the resin, was sufficient to Scheme 3B

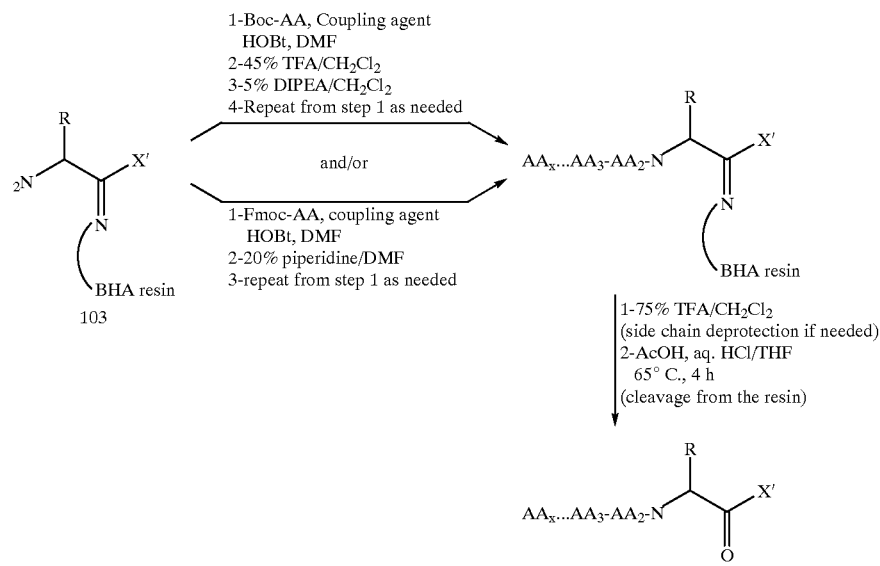

completely deprotect the acid-sensitive side chain protecting groups. However, in a few examples the O-t-Bu derivative of threonine and aspartic acid were also isolated indicating that the deprotection was not complete in those cases.

α-ketoamides could also be synthesized by the same process (compounds 218 and 219 from example 62) and in similar overall yields.

By its generality, this methodology is well suited for an application in rapid lead optimization and in the generation of libraries for the purpose of identifying novel trifluoromethyl ketone and α-ketoamide inhibitors of serine proteases.

Protocols and yields of purified final products are reported in Examples 1 and 62 respectively.

Solution Chemistry.
Schemes 4, 5, and 6:

Peptides containing activated ketones other than trifluoromethyl ketone could also be prepared by sequentially coupling a suitably protected amino alcohol with the required amino acids or peptide segment using standard solution methods. After the complete backbone was established, oxidation of the resulting alcohol gave the desired compound. The preparation of the various building blocks are shown in Schemes 4, 5 and 6.

Condensation of Weinreb amide 10 with CF₃CF₂Li followed by reduction with NaBH₄ gave pentafluoroethyl substituted alcohol 11 (Scheme 4).

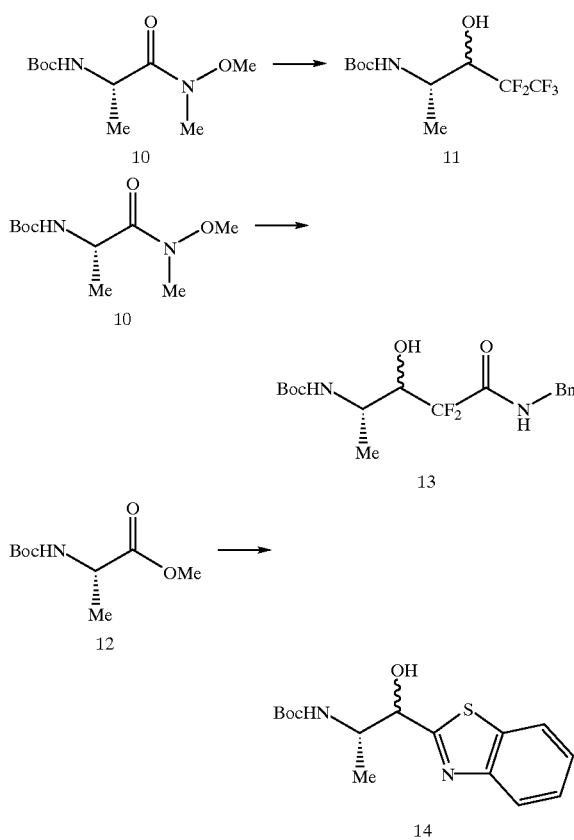

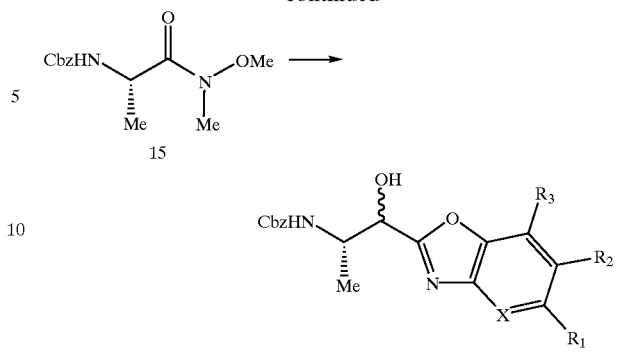

16: X = CH, R₁ = R₂ = R₃ = H
17: X = N, R₁ = R₂ = R₃ = H
18: X = CCH₃, R₁ = R₂ = R₃ = H
19: X = CH, R₁ = CH₃, R₂ = R₃ = H
20: X = CH, R₁ = R₃ = H, R₂ = CH₃
21: X = CH, R₁ = R₂ = H, R₃ = CH₃

The α,α-difluoroamide 13 was prepared from an ultrasonic Reformatsky reaction (Thaisrivongs, S.; Pals, P. T.; Kati, W. M.; Turner, S. R.; Thomasco, L. M.; Watt, W.; Design and synthesis of potent and specific renin inhibitors containing diflurostatine, difluorstatone, and related analogues. *J. Med. Chem.* 1986, 24, 2080–2087) between ethyl bromodifluoroacetate and Boc-alaninal followed by treatment with benzylamine. Benzothiazole 14 was obtained in a straightforward manner when 2-lithiobenzothiazole was added to this same aldehyde. The remaining benzoxazole derivatives 16 to 21 were synthesized as shown from amide 15. Reduction to the aldehyde by the action of LiAlH₄ was followed by cyanohydrin formation, partial hydrolysis and cyclization using procedures previously described [(a) Edwards, P. D.; Meyer, E. F. Jr.; Vijayalakshmi, I.; Tuthill, P. A.; Andisik, D. A.; Gomes, B.; Strimpler, A. Design, synthesis, and kinetic evaluation of a unique class of elastase inhibitors, the peptidyl α-ketobenzoxazoles, and the X-ray crystal structure of the covalent complex between porcine pancreatic elastase and Ac-Ala-Pro-Val-2-benzoxazole. *J. Am. Chem. Soc.* 1992, 114, 1854–1863. (b) Edwards, P. D.; Zottola, M. A.; Davis, M.; Williams, J.; Tuthill, P. A. Peptidyl α-ketoheterocyclic inhibitors of human neutrophil elastase. 3. In vitro and in vivo potency of a series of peptidyl α-ketobenzoxazoles. *J. Med. Chem.* 1995, 38, 3972–3982. (c) Edwards, P. D.; Wolanin, D. J.; Andisik, D. W.; Davis, M. W. Peptidyl α-ketoheterocyclic inhibitors of human neutrophil elastase. 2. Effect of varying the heterocyclic ring on in vitro potency. *J. Med. Chem.* 1995, 38, 76–85. (d) Tsutsumi, S.; Okonogi, T.; Shibahara, A.; Ohuchi, S.; Hatsushiba, E.; Patchett, A. A.; Christensen, B. G. Synthesis and structure-activity relationships of peptidyl α-keto heterocycles as novel inhibitors of prolyl endopeptidase. *J. Med. Chem.* 1994, 37, 3492–3502].

Various α-ketoamide derivatives could also be prepared according to the alternative procedure depicted in Scheme 5.

Scheme 5

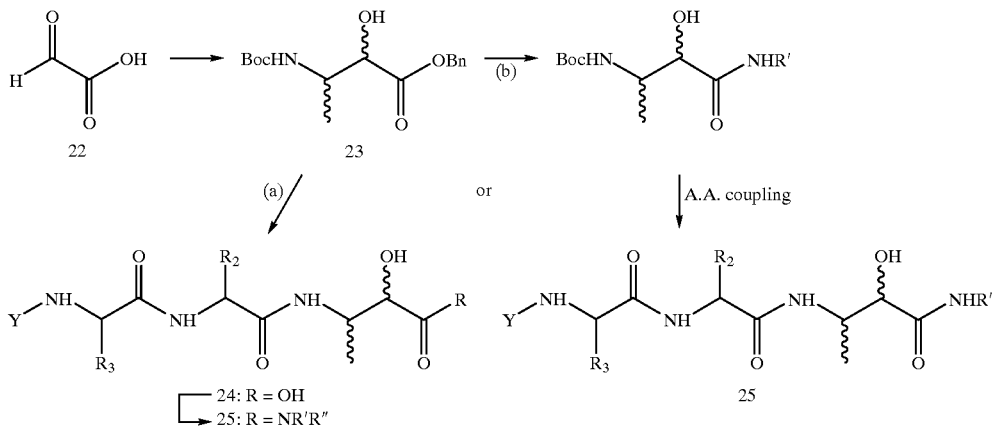

Route a:

A Henry reaction between glyoxylic acid and nitroethane gave 23 after reduction and suitable protection. Coupling the required amino acids using standard methods gave 24 after removal of the benzyl ester. Incorporation of the appropriate amide function gave a series of alcohols 25 which were readily oxidized to the desired ketones using the Dess-Martin reagent (Dess, D. B.; Martin, J. C. Readily accessible 12-I-5 oxidant for the conversion of primary and secondary alcohols to aldehydes and ketones. *J. Org. Chem.* 1983, 48, 4155–4156).

Route b:

Alternatively, 23 could be hydrogenated to the corresponding acid and the appropriate P1' amine coupled. Coupling the required amino acids using standard methods gave 25. The alcohol 25 was readily oxidized to the desired ketones as above.

The preparation of the unnatural amino acids adamantyl glycine and β,β-dimethyl aspartic acid are shown in Scheme 6.

Scheme 6

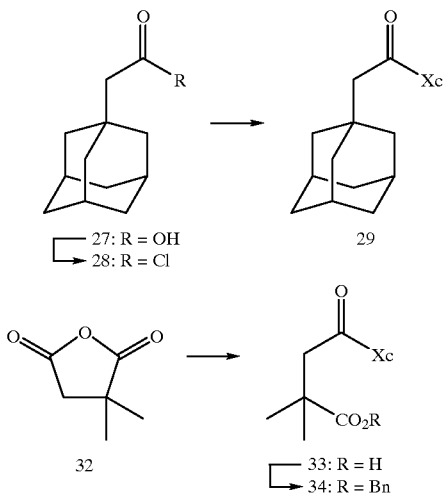

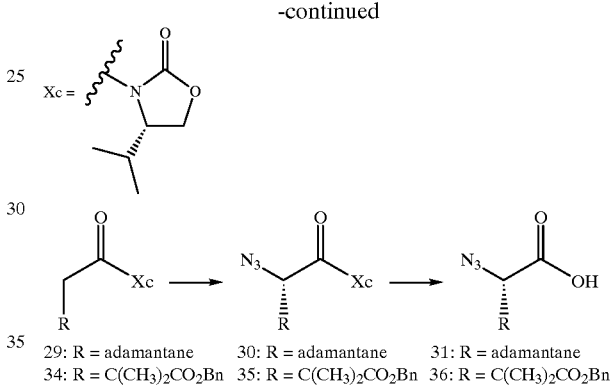

Thus oxazolidinone 29 was obtained from acid 27 using procedures described previously (Gage, J. R.; Evans, D. A. Diastereoselective aldol condensation using a chiral oxazolidinone auxiliary: (2S*, 3S*)-3-hydroxy-3-phenyl-2-methylpropanoic acid. *Org Syn.* 1989, 68, 83–91). Formation of the enolate followed by treatment with TrisN$_3$ (Evans, D. A.; Britton, T. C.; Ellman, J. A.; Dorow, R. L. The asymmetric synthesis of α-amino acids. 15 Electrophilic azidation of chiral imide enolates, a practical approach to the synthesis of (R)- and (S)-azido carboxylic acids. *J. Am. Chem. Soc.* 1990, 112, 4011–4030) gave azide 30 which was hydrolyzed to yield acid 31 in a straightforward manner. To the carboxylate group of this azido acid was then introduced the appropriate amino acid residues. Capping the N-terminus was accomplished using standard coupling methods after reduction of the azide moiety. Using a similar approach, anhydride 32 was converted to protected azido acid 36.

The following examples are provided to describe the invention in further detail. These examples, which set forth the best mode presently contemplated for carrying the invention, are intended to illustrate and not to limit the invention.

EXAMPLES

Unless otherwise noted, materials were obtained from commercial sources and used without further purification. The purity of each inhibitor was determined by HPLC, ¹H-NMR, and/or elemental analysis. ¹H-NMR spectra were obtained at 400 MHz on a Bruker AMX 400 spectrometer. FAB mass spectra were recorded on an Autospec, VG spectrometer. Column chromatography was performed either on silica gel (10–40 μm or 230–400 mesh ASTM, E. Merck) or by preparative HPLC using a Partisil 10 ODS-3, $C_{18}$ preparative column (50 cm×22 mm). Analytical HPLC were carried out on the following systems; System A: Vydac C18, 10 μm analytical column (24 cm×4.6 mm); mobile phase, acetonitrile/0.06% trifluoroacetic acid (TFA) in water/0.06% TFA; System B: Vydac C18, 5 μm analytical column (15 cm×4.6 mm); mobile phase, acetonitrile in 50 mM $NaH_2PO_4$ at pH 4.4; System C: Vydac $C_{8, 10}$ μm analytical column (24 cm×4.6 mm); mobile phase, acetonitrile in 20 mM $Na_2HPO_4$ at pH 8.0; System D: symmetry shield C8, 10 μm analytical column (15 cm×3.9 mm); mobile phase, acetonitrile in 20 mM $Na_2HPO_4$ at pH 9.0; System E: Supelcosil C8, 5 μm analytical column (15 cm×4.6 mm); mobile phase, acetonitrile/0.1% TFA in water/0.1% TFA at pH 2.0.

Abbreviations or symbols used in the examples, or throughout the present specification, include Boc, tertiary butyloxycarbonyl; BOP: benzothiazol-1-yloxy-tris(dimethylamino)phosphonium hexafluorophosphate; DA-Tbg, desamino-tertiary-butylglycine (3,3-dimethylbutylbutanoic acid); DCC: N,N'-dicyclohexylcarbodiimide; DIC, 2-dimethylaminoisopropyl chloride hydrochloride; DMF, N,N,-dimethylformamide; DMSO, dimethylsulfoxide; DTT, dithiothreitol; EDC: 1-ethyl-3-(3-dimethylaminopropyl)-carbodiimide. hydrochloride salt; Fmoc, 9-fluorenylmethyloxycarbonyl; HCMV, human cytomegalovirus; HOBt, 1-hydroxybenzotriazole hydrate; MES, 4-morpholineethanesulfonic acid; NMP, N-methylpyrrolidone; PCR, polymerase chain reaction; Ph, phenyl; PMSF, phenylmethylsulfonyl fluoride; QSAR, quantitative structure activity relationship; Tbg, tertiary-butylglycine; tBu, tertiary-butyl; TFA, trifluoroacetic acid; Trt, triphenylmethyl; TBTU, O-(benzotriazol-1-yl)-1,1,3,3-tetramethyluronium tetrafluoroborate; TCEP, tris(2-carboxyethyl)phosphine hydrochloride; TRIS, tris(hydroxymethyl)aminomethane.

Example 1

General Procedure for the Solid Phase Synthesis of Peptides

1-Boc/DIC/HOBtPprotocol.

The peptides were assembled on a ACT396 peptide synthesizer sold by Advanced Chemtech (Louisville, Ky.). Each reaction vessels were charged with the appropriate resins 103 (0.25 mmol) and were successively washed with 3.5 mL portions of $CH_2Cl_2$ (2×), MeOH (2×) and $CH_2Cl_2$ (2×). The amino acids were coupled as their activated HOBt esters, utilizing 4.8 equivalents of the reagents as follows: A 0.5 M solution of a mixture of Fmoc-protected amino acid and HOBt in DMF (2.4 mL, 1.2 mmol of each) was added to the deprotected resin, followed by addition of a 0.5 M DIC solution in $CH_2Cl_2$ (2.4 mL, 1.2 mmol). The reaction vessel was shaken for 3.5 h. The reaction vessel was drained and the remaining resin was washed twice with 5 mL of $CH_2Cl_2$. Fresh portions of reagent solutions were added and the coupling step was repeated for 3.5 h. After the coupling, the resin was washed successively with 5 mL portions of $CH_2Cl_2$ (2×), MeOH (2×) and $CH_2Cl_2$ (2×). The Boc amino protecting groups was removed with a solution of 45% TFA in $CH_2Cl_2$ (4 mL for 25 min) and washed as above. After the last coupling, an additional washing step with 5 mL of $CH_2Cl_2$ (3×) was done and the resin was dried in vacuo.

2-Fmoc/TBTU/HOBt Protocol.

The peptides were assembled as above except for the coupling which was done as follow: The resin was suspended in NMP (0.35 mL) and was treated with a 0.5 M solution of a mixture of Fmoc-protected amino acid and HOBt in NMP (1.8 mL, 0.9 mmol of each), a 0.5 M solution of TBTU in DMF (1.8 mL, 0.9 mmol) and a 1.0 M solution of DIPEA in NMP (1.8 mL. 1.8 mmol). The reaction vessel was shaken for 1.25 h, it was drained and the remaining resin was washed twice with 3.5 mL of DMF. Fresh portions of reagent solutions were added and the coupling step was repeated for 1.25 h. The deprotection of the Fmoc group was done by treating the resin with a 25% solution of piperidine in DMF for 25 minutes.

3-Boc/TBTU/HOBt Protocol.

The peptides were assembled on a COUPLER™ 250 C (VEGA Biotechnologies) or on an ACT 90 (Advanced ChemTech) peptide synthesizer. The reaction vessel was charged with the appropriate resins 103 (0.25 mmol) which was successively washed with 15 mL portions of $CH_2Cl_2$ (2×, MeOH (2×) and $CH_2Cl_2$ (2×). The amino acids were coupled as their activated HOBt esters, utilizing 3 equivalents of the reagents as follows: The resin was suspended in DMF (15 mL) and was treated with the Boc-protected amino acid (0.75 mmol), HOBt hydrate (0.75 mmol), DIPEA (1.5 mmol, 0.26 mL) and TBTU (0.75 mmol, 241 mg). The reaction vessel was shaken for 1 h and the completion of the coupling monitored by Kaiser test. In the case of incomplete couplings, the reaction vessel was drained and the resin was washed twice with 15 mL of $CH_2CL_2$. Fresh reagents were added and the coupling step was repeated for an extra hour. The reaction vessel was drained and the resin washed as above. The Boc protecting group was removed by successive treatment (5 min. then 20 min.) with 15 mL of a 45% solution of TFA in $CH_2Cl_2$. The resin was washed with $CH_2CL_2$ (2×), 5% DIPEA in $CH_2CL_2$ (1 min. then 5 min.), $CH_2Cl_2$ (2×), MeOH (2×) and $CH_2Cl_2$ (2×).

General Procedure for the Cleavage of the Peptidyl Activated Ketone from the Solid Support (according to scheme 3B)

The dried resin (~800 mg) was suspended in THF (9 mL), $H_2O$(0.50 mL), AcOH (0.25 mL) and 1M aq. HCl (0.10 mL) and was heated in a bomb at 65° C. for four hours. The solution was cooled down, filtered and treated as above one more time. In the case where the sequence contained a basic residue such as lysine or histidine, an extra 0.05 mL of 1 M HCl was used and the procedure was repeated a third time. All the mother liquors were combined, the THF was concentrated in vacuo and the residue was purified on reversed phase HPLC (Whatman HPLC column, 22.0 mm×500 mm, Partisil 10 ODS-3 M/20–50, particle size 10 μm, solvents: A=0.06 % TFA/$H_2O$, B=75% $CH_3CN$-25% $H_2O$ containing 0.06% TFA; gradient 0 to ~50% B in 60 min). The desired peptidyl activated ketones 201–219 were isolated in yields reported in Example 62.

Example 2

Alternative Synthesis of α-ketoamides (according to scheme 5)

Preparation of 3-{2-[2-(3,3-dimethyl-butyrylamino)-3,3-dimethyl-butyrylamino]-3-dimethylcarbamoylpropionylamino}-2-oxo-butyric acid benzyl amide (76, Table 6)

Preparation of α-hydroxy ester 23.

To a solution of nitroethane (4.0 g, 53 mmol) in ethanol (15 mL) was added aqueous NaOH (68 mL of 2N solution, 136 mmol). To this rapidly stirred solution was added glyoxylic acid (5.9 g, 64 mmol). The solution was stirred 15 h and then acidified with 10% aqueous HCl (pH 2) and the aqueous phase saturated with NaCl before extraction with EtOAc (3×150 mL). The organic phase was dried (MgSO$_4$), filtered and concentrated to give 8.1 g of a viscous yellow oil. This crude material was dissolved in ethanol (50 mL) containing Et$_3$N (18 mL, 119 mmol) and treated with di-tert-butyl dicarbonate (12.2 g, 56 mmol) and Raney nickel (3 g) which had been washed with water immediately before use. Hydrogenation at 45 p.s.i for 20 h afforded after filtration through Celite and concentration, the crude acid (11.1 g). A portion of the crude acid (3.07 g, 14 mmol) was dissolved in DMF (30 mL) and treated with anhydrous K$_2$CO$_3$ (4.3 g, 30.8 mmol) and benzyl bromide (2.5 mL, 21 mmol). After stirring for 3 h at room temperature, the DMF was removed under reduced pressure and the residue dissolved in EtOAc (150 mL) and washed with water (100 mL) and brine (80 mL). The organic phase was dried over MgSO$_4$, filtered and concentrated. The crude yellow oil (4.3 g) was purified by flash chromatography on silica gel (230–400 mesh), eluting with 33% EtOAc in hexane to provide pure benzyl ester 23 (1.8 g, 42% from nitroethane). HPLC (system C) 99%, (system D) 97%; IR (KBr) υ 3422, 3361, 1740, 1684 cm$^{-1}$; $^1$H-NMR (400 MHz, 1H), 5.19 (d, J=12.1 Hz, 1H), 4.82 (m, 1H), 4.36 and 4.35 (2×d, J=5.7 and 5.4 Hz, 1H), 4.11 (m, 1H), 3.10 (m, 1H), 1.43 (s, 9H), 0.97 (d, J=7.0 Hz, 3H); FAB MS m/z: 310 (MH$^+$), 210 (M−100); HRMS calcd for C$_{16}$H$_{24}$NO$_5$ (MH$^+$) 310.1654, found: 310.1644; Anal (C$_{16}$H$_{23}$NO$_5$) C, H, N.

Synthesis of α-keto Acid 24.

The tert-butyloxycarbonyl (Boc) group from ester 23 (4.0 g, 12.9 mmol) was removed using 4 N HCl/dioxane (30 mL) for 45 min at 0° C. The hydrochloride salt was obtained by concentration and coevaporation with toluene (15 mL). The HCl salt (12.9 mmol) was combined with EDC (2.6 g, 13.6 mmol, 1.1 equiv.), HOBt (1.8 g, 13.6 mmol, 1.1 equiv.) and Boc-Asn (NMe$_2$)—OH (3.4 g, 12.9 mmol, 1.1 equiv.) in DMF (50 mL) under a nitrogen atmosphere. The solution was cooled to 0° C. (ice bath) before iPr$_2$NEt (7.9 mL, 45.3 mmol, 3.5 equiv.) was added. The solution was then stirred at room temperature for 16 h. The reaction mixture was partitioned between EtOAc (250 mL) and sat. aqueous NaHCO$_3$ (150 mL). The organic phase was washed with 5% aq. HCl (150 mL) and finally brine (150 mL). Drying (MgSO$_4$) was followed by filtration and concentration to give 6.0 g of crude material. In most cases the crude material was suitable for subsequent couplings without purification. After the final coupling, the α-hydroxy benzyl ester peptides were purified by flash chromatography. The acid 24 was then obtained from the benzyl ester (1.10 g, 2.0 mmol) by hydrogenation over 10% Pd/C (55 mg) in ethanol (30 mL) at atmospheric pressure over the course of a few hours to afford after filtration through a pad of Celite a white solid (0.95 g, 100% yield). HPLC (system A) 100%, (system C) 100%; IR (KBr)υ 3316, 1727, 1642 cm$^{-1}$; $^1$H-NMR (400 MHz, CDCl$_3$), mixture of 4 diastereomers, δ 8.06 and 8.01 (2×d, J=7.3 and 8.6 Hz, 1H), 7.87, 7.79, 7.70 and 7.54 (4×d, J=8.6, 8.6, 8.9 and 8.6 Hz, 1H), 7.09 and 7.03 (2×d, J=7.9 and 8.6 Hz, 0.5H), 6.72 (m, 0.5H), 6.52 (m, 0.25), 6.34 and 6.29 (2×d, J=7.6 and 7.3 Hz, 0.75H), 6.10–5.4 (br s, 1H), 4.99–4.88 (m, 0.5H), 4.87–4.78 (m, 0.5H), 4.66–4.37 (m, 2H), 4.33–4.09 (m, 1H), 3.30–3.15 (m, 0.3H), 3.05–2.85 (m, 6.7 H), 2.75–2.65 and 2.60–2.50 (m, 1H), 2.25–2.10 (m, 2H), 1.28–1.19 (m, 3H), 1.10–0.97 (m, 18H); $^{13}$C-NMR (100.6 MHz, CDCl$_3$) δ 174.9, 173.5, 173.1, 173.0, 171.5, 171.0, 170.9, 170.8, 170.7, 170.5, 170.2, 73.03, 72.74, 60.9, 60.67, 50.3, 50.1, 49.5, 49.4, 48.1, 47.9, 47.7, 37.56, 35.9, 35.8, 35.7, 34.7, 34.4, 34.3, 33.8, 31.1, 29.9, 29.8, 26.9, 26.8, 26.7, 17.4, 17.2; FAB MS m/z: 473 (MH$^+$), 495 (M+23); HRMS calcd for C$_{22}$H$_{41}$N$_4$O$_7$ (MH$^+$) 473.2975, found: 473.2990; Anal (C$_{22}$H$_{40}$N$_4$O$_7$) C, H, N.

Coupling of the P$_1$' residue was accomplished using the above general coupling protocol with the appropriate terminal amine (1.2 equiv.). The final oxidation step was performed by treatment of the prerequisite α-hydroxy amide (62 mg, 0.11 mmol) with 2 equivalents of the Dess-Martin periodinane (94 mg, 0.22 mmol) in DMF (1 mL) for 4 h. Addition of 10% sodium thiosulfate (5 mL) and sat. NaHCO$_3$ (5 mL) with stirring (15 min) was followed by extraction with EtOAc (3×10 mL) to give the desired α-ketoamide. Final purification was performed using preparative HPLC to afford 76 after lyophilization, (51 mg, 82% yield) as a white solid. HPLC (system C) 100%, (system D) 96.1%; IR (KBr) υ 3316, 1641, 1529 cm$^{-1}$; $^1$H-NMR (400 MHz, DMSO-d$_6$), 1:1 mixture of diastereoisomers at P$_1$, δ 9.21–9.15 (m, 1H) 8.14 and 8.09 (2×d, 7.3 and 7.6 Hz, 1H), 8.03 and 7.97 (2×d, J=6.4 and 5.7 Hz, 1H), 7.60 (d, J=8.3, 1H), 7.35–7.17 (m, 5H), 5.02–4.88 (m, 1H), 4.64–4.49 (m, 1H), 4.39–4.23 (m, 2H), 4.13 and 4.12 (2×d, J=8.6 and 8.6 Hz, 1H), 2.92 and 2.91 (2×s, 3H), 2.79 and 2.78 (2×s, 3H), 2.74–2.54 (m, 2H), 2.19 (br d, J=12.4 Hz, 1H), 2.03 and 2.02 (2×d, J=12.4 and 12.7 Hz, 1H), 1.25 and 1.23 (2×d, J=7.3 and 7.0 Hz, 3H), 0.94 and 0.91 (2×s, 18H); FAB MS m/z: 560 (MH$^+$), 582 (M+23); HRMS calcd for C$_{29}$H$_{46}$N$_5$O$_6$ (MH$^+$) 560.3448, found: 560.3426.

Example 3

Alternative Preparation of Fmoc-Asp(Rink Resin) aminotrifluoromethyl alcohol (5) (according to scheme 2; R:Me)

4-(tert-butoxycarbonylamino)-1,1,1-trifluorobutan-2-ol (3).

This compound was prepared according to a literature procedure analogous to the preparation of the valine analogue (Skiles, J. W.; Fuchs, V.; Miao, C.; Sorcek, R.; Grozinger, K. G.; Mauldin, S. C.; Vitous, J.; Mui, P. W.; Jacober, S.; Chow, G.; Matteo, M.; Skoog, M.; Weldon, S. T.; Possanza, G.; Keirns, J.; Letts, G.; Rosenthal, A. Inhibition of human leukocyte elastase (HLE) by N-substituted peptidyl trifluoromethyl ketones. *J. Med. Chem.* 1992, 35, 641–662). IR (KBr) υ 3313 (br), 1681, 1527 cm$^{-1}$; $^1$H-NMR (400 MHz, DMSO-d$_6$), 1:1 mixture of diastereomers, δ 6.84 and 6.43 (d, J=8.4 Hz and 8.9 Hz, 1H), 6.32 and 6.24 (d, J=6.9 and 7.4 Hz, 1H), 3.93–3.81 (m, 1.5H), 3.70 (quint, J=7.3 Hz, 0.5H), 1.373 and 1.371 (s, 9H), 1.10 and 1.07 (d, J=7.4 and 6.4 Hz, 3H); FAB MS m/z: 244 (MH$^+$); Anal (C$_9$H$_{16}$F$_3$NO$_3$) C, H, N.

Fmoc-Asp(Ot-Bu)-aminotrifluoromethyl alcohol (4).

This compound was prepared in solution by coupling Fmoc-Asp(Ot-Bu)—OH and the alanine-derived aminotrifluoromethyl alcohol. HPLC (system A) 98%, (system B) 99%; IR (KBr) υ 3300, 1721, 1697, 1661, 1540 cm$^{-1}$; $^1$H-NMR (400 MHz, DMSO-d$_6$) δ 7.99–7.93 (m, 1H), 7.89 (d, J=7.3 Hz, 2H), 7,70 (m, 2H), 7.55 (dd, J1=15.9 Hz, J2=8.6 Hz, 1H), 7.45–7.39 (m, 2H), 7.35–7.29 (m, 2H), 6.41 (d, J=7.0 Hz, 1H), 4.40–4.19 (m, 4H), 4.06–3.88 (m, 2H), 2.66–2.58 (m, 1H), 2.44–2.40 (m, 1H), 1.37 (s, 9H), 1.08 (d, J=6.7 Hz, 3H); FAB MS m/z: 537 (MH$^+$); HRMS calcd for C$_{27}$H$_{32}$F$_3$N$_2$O$_6$ (MH$^+$) 537.2212, found: 537.2229.

The compound above was deprotected with 40% TFA in CH$_2$Cl$_2$ and coupled on a Rink resin with DCC/HOBt to afford (5).

Example 4

Preparation of Other Activated Ketones (according to scheme 4)

4-(tert-butoxycarbonylamino)-1,1,1,2,2-pentafluoropentan-3-ol (11).

To a dry 500 mL round bottom flask was added anhydrous $Et_2O$ (100 mL) and a 1.5 M solution of MeLi·LiBr in $Et_2O$ (100 mL, 150 mmol). This solution was subsequently cooled to −78° C. A second flask was cooled to −78° C. and charged with $Et_2O$ (100 mL) and $CF_3CF_2I$ (44.7 g, 182 mmol). The contents of this flask were then added via canula over 15 min to the MeLi·LiBr slurry. The resulting solution was stirred for 30 min at −78° C. before the Weinreb amide 10 (10.6, 45.5 mmol) was added in one portion. The reaction was stirred at −78° C. for 90 min and then allowed to warm to −30° C. for 2 h. The reaction was quenched by the addition of sat. $NH_4Cl$ (125 mL). The organic phase was washed with $H_2O$ (2×50 mL), dried over $Na_2SO_4$, filtered and concentrated to provide an orange oil. The oil was redissolved in 20% MeOH/THF (100 mL) and transferred to a 500 mL round bottom flask. The solution was cooled to 0° C. before $NaBH_4$ (1.9g, 50.1 mmole) was added portionwise over 5 min (Caution! foaming occurs). The reaction was subsequently stirred for 1 h at 0° C. $Et_2O$ (200 mL) was added followed by 10% citric acid (100 mL). The aqueous layer was extracted with $Et_2O$ (3×50 mL). The combined organic extracts were washed with $NaHCO_3$ (1×50 mL), brine (1×50 mL), dried over $Na_2SO_4$, filtered and concentrated in vacuo. The residue was purified by flash chromatography (20% ethyl acetate in hexanes) to provide a colorless oil 11, 12.3 g (92%). HPLC (system D) 100%, IR (KBr) υ 3368, 2987, 1687 cm$^{-1}$; $^1$H-NMR (400 MHz, DMSO-d$_6$) 25:1 mixture of diastereomers, δ 6.87 (d, J=8.0, 1.5H), 6.42 (d, J=8.9 Hz, 0.5H), 6.32 and 6.25 (2×d, J=8.0 and 8.3 Hz, 1H), 4.08–3.78 (m, 2H), 1.37 (s, 9H), 1.13 and 1.08 (2×d, J=7.0 and 6.7 Hz, 3H); FAB MS m/z: 294 (MH$^+$); HRMS calcd for $C_{10}H_{17}F_5NO_3$ (MH$^+$) 294.1129, found: 294.1138.

Benzyl 4-(tert-butoxycarbonylamino)-2,2-difluoro-3-hydroxy-(4S)-pentanoate (13).

This material was prepared using a modification of the procedure previously described (Thaisrivongs, S.; Pals, P. T.; Kati, W. M.; Turner, S. R.; Thomasco, L. M.; Watt, W.; Design and synthesis of potent and specific renin inhibitors containing diflurostatine, difluorstatone, and related analogues. *J. Med. Chem.* 1986, 24, 2080–2087). Thus amide 10 (14.9 g, 64.3 mmol) was dissolved in THF (230 mL) at 0° C. LiAlH$_4$ (4.90 g, 129 mmol) was added in several portions over a period of 20 min, and the suspension was then stirred for 2 h at 0° C. This suspension was transferred via cannula into 500 mL of 10% aqueous citric acid and stirred for 1 h. The mixture was extracted with $Et_2O$ (3×) and the combined organic phases washed with water, brine, dried (MgSO$_4$), filtered and concentrated to give the corresponding aldehyde as a white solid (10.7 g, 97%). $^1$H-NMR (CDCl$_3$) δ 9.57 (s, 1H), 5.09 (br, 1H), 4.23 (br, 1H), 1.46 (s, 9H), 1.34 (d, J=7.3 Hz, 3H). Zinc dust (16.2 g, 24.8 mmol) was placed in THF (40 mL) and sonicated 30 min. A solution of the aldehyde (10.7 g, 62 mmol) and ethyl bromodifluoroacetate (20 g, 99 mmol) was added over 30 min using a syringe pump while sonicating. Sonication was continued for 1.5 h before the suspension was poured into 500 mL of 10% aqueous citric acid and extracted with EtOAc (3×). The combined organic extracts were washed with water, brine, dried (MgSO$_4$), filtered and concentrated in vacuo. The oil obtained contained 20% of the starting aldehyde but was used without further purification. The hydroxy ester (2.20 g, 7.40 mmol), benzylamine (3.96 g, 37.0 mmol) and i-Pr$_2$NEt (4.76 g, 37.0 mmol) were heated in refluxing ethanol for 18 h. The solution was concentrated to dryness, taken up into EtOAc and washed with 1 N HCl, brine, dried (MgSO$_4$), filtered and concentrated in vacuo to give a yellow oil. This material was purified by flash chromatography using TLC grade silica gel to give 13 as a white solid (1.17g, 44% over 2 steps).

HPLC (system B) 100%, (system C) 99%; IR (KBr) υ 3344, 2979, 1684 cm$^{-1}$; $^1$H-NMR (CDCl$_3$) 4:1 mixture of isomers δ 5 7.20 (m, 5H), 6.90 (br s, 1H), 4.75 (m, 1H), 4.45 (m, 2H), 4.08 (br s, 1H), 3.88 (m, 2H), 1.32 (s, 9H), 1.16 (d, 3H); $^{13}$C-NMR (100.6 MHz, DMSO-d$_6$) δ 164.58, 164.30, 164.02, 155.61, 139.31, 129.11, 127.97, 127.72, 119.99, 117.47, 114.88, 78.59, 71.91, 71.65, 71.44, 46.28, 43.04, 29.10, 19.35; FAB MS m/z: 359 (MH$^+$); HRMS calcd for $C_{17}H_{25}F_2N_2O_4$ (MH$^+$) 359.1782, found: 359.1768; Anal ($C_{17}H_{24}F_2N_2O_4$) C, H, N.

(2S)-2-(tert-butoxycarbonylamino)-1-benzo[d][1,3]thiazol-2-yl-1-propanol (14).

This compound was prepared from methyl ester 12 using the procedure previously described (Tsutsumi, S.; Okonogi, T.; Shibahara, A.; Ohuchi, S.; Hatsushiba, E.; Patchett, A. A.; Christensen, B. G. Synthesis and 20 structure-activity relationships of peptidyl α-keto heterocycles as novel inhibitors of prolyl endopeptidase. *J. Med. Chem.* 1994, 37, 3492–3502). Thus a solution of 12 (28.1 g, 132 mmol) in THF (50 mL) was added dropwise to a suspension of LiAlH$_4$ (3.76 g, 396 mmol) in THF (200 mL) at 0° C. After complete addition the mixture was stirred at room temperature for one hour. Celite (34 g) was then added followed by the careful addition of water (34 mL), 2N NaOH (34 mL) and water (100 mL) and stirring was continued for an hour. The resulting white suspension was filtered, and the filter cake was washed with EtOAc. The desired alcohol was obtained as a colorless oil (21.07 g, 91%). $^1$H-NMR (CDC$_{l3}$) δ 4.66 (br s, 1H), 3.77 (br s, 1H), 3.68–3.61 (m, 1H), 3.53–3.47 (m, 1H), 2.65 (br s, 1H), 1.45 (s, 9H), 1.14 (d, J=6.7 Hz, 3H). To a solution of this alcohol (3.25 g, 18.5 mmol) and Et$_3$N (7.75 mL, 55.6 mmol) in anhydrous $CH_2Cl_2$ (60 mL) at 0° C. was added SO$_3$·py (8.85 g, 55.6 mmol) in small portions. The solution was then stirred at room temperature for 1.5 h before being poured into ice water and extracted three times with $CH_2Cl_2$. The combined organic extracts were dried (MgSO$_4$), filtered and concentrated to give an oil which was purified by flash chromatography to give the desired aldehyde (2.34 g, 73%) which was used immediately. $^1$H-NMR (CDC$_{l3}$) δ 9.57 (s, 1H), 5.09 (br, 1H), 4.23 (br, 1H), 1.46 (s, 9H), 1.34 (d, J=7.3 Hz, 3H). To a solution of benzothiazole (4.43 mL, 40.5 mmol) in THF (100 mL) at −78° C. was added nBuLi (26.5 mL of a 1.4M solution in hexanes, 37.15 mmol). After stirring for 30 min, a solution of the above aldehyde (2.34 g, 13.51 mmol) in THF was added. The solution was stirred for 72 min before being quenched by the addition of saturated NH$_4$Cl. Extraction with EtOAc was followed by a wash with brine and drying over MgSO$_4$. Flash chromatography afforded the desired product as an orange oil. HPLC (system A) 100%, (system D, pH 7.4) 100%; IR (KBr) υ 3272, 1713 cm$^{-1}$; $^1$H-NMR (400 MHz, DMSO-d$_6$), 6:1 mixture of diastereomers at P$_1$, δ 8.07–8.05 (m, 1H), 7.96–7.92 (m, 1H), 7.50–7.45 (m, 1H), 7.41–7.37 (m, 1H), 6.81 and 6.44 (2×d, J=8.6 Hz, 1H), 6.47 (d, J=5.4 Hz, 1H), 4.92–4.90 (m, 1H), 4.03–3.96 (m, 1H), 1.32 and 1.29 (2×s, 9H), 1.08 and 0.98 (2×d, J=6.7 and 6.7 Hz, 3H); FAB MS m/z: 309 (MH$^+$), HRMS calcd for $C_1SH_{21}N_2O_3S$ (MH$^+$) 309.1273, found: 309.1283.

(2S)-2-(benzyloxycarbonylamino)-1-benzo[d][1,3]oxazol-2-yl-1-propanol (16).

This compound was prepared from 15 and 2-aminophenol using the procedure previously described ((a) Edwards, P. D.; Meyer, E. F. Jr.; Vijayalakshmi, I.; Tuthill, P. A.; Andisik, D. A.; Gomes, B.; Strimpler, A. Design, synthesis, and kinetic evaluation of a unique class of elastase inhibitors, the peptidyl α-ketobenzoxazoles, and the X-ray crystal structure of the covalent complex between porcine pancreatic elastase and Ac-Ala-Pro-Val-2-benzoxazole. *J. Am. Chem. Soc.* 1992, 114, 1854–1863). To a solution of N-benzyloxycarbonyl-(S)-alanine (20.0 g, 89.7 mmol) in $CH_2Cl_2$ (200 mL) at 0° C., was added 1-1'-carbonyldiimidazole (18.2 g, 115.7 mmol). After 30 min of stirring at 0° C., $Et_3N$ (16.1 mL, 115.7 mmol) was added followed by the addition of O,N-dimethylhydroxylamine hydrochloride (11.3 g, 115.7 mmol). The mixture was stirred 1 h at 0° C. and then at room temperature for 4 h. $CH_2Cl_2$ was added and the organic phase was washed twice with 10% aqueous HCl, saturated $NaHCO_3$ and brine and dried over $MgSO_4$. Removal of the solvent in vacuo gave amide 15 (24.2 g) which was used without further purification. $^1$H-NMR ($CDCl_3$) δ 7.4–7.3 (m, 5H), 5.65–5.55 (m, 1H), 5.15–5.05 (m, 2H), 4.82–4.74 (m, 1H), 3.77 (s, 3H), 3.21 (s, 3H), 1.34 (d, J=6.9 Hz, 3H). This compound was dissolved in THF (350 mL) at 0° C. A 1.0 M solution of $LiAlH_4$ in THF (110 mL, 110 mmol) was added dropwise over 30 min. Stirring was then continued at room temperature for 2 h. The mixture was then cooled to 0° C. and a solution of $KHSO_4$ (22.4 g) in water (250 mL) was added carefully. After stirring at 0° C. for one hour, the solution was extracted with ether and washed twice with 10% aqueous HCl, twice with saturated $NaHCO_3$ and once with brine. The organic phase was dried ($MgSO_4$), filtered and concentration in vacuo to give the desired aldehyde (19.4 g) which was immediately dissolved in $CH_2Cl_2$ (350 mL) and cooled to 0° C. A solution of $NaHSO_3$ (55.9 g, 540 mmol) in water (150 mL) was introduced and the resulting mixture stirred for one hour. NaCN (25.0 g, 511 mmol) was then added and stirring was continued overnight. The suspension was diluted with EtOAc (250 mL) and hexanes (250 mL) and the layers separated. Washing with water and brine was followed by drying over $MgSO_4$ to afford the desired cyanohydrin (18.26 g, 83%) which was dissolved in benzene (350 mL) and stored at −20° C. To a mixture of ethanol (47.1 mL, 803 mmol) and $CHCl_3$ (50 mL) at 0° C. was added AcCl (53.5 mL, 752 mmol). After stirring at 0° C. for 30 min. a solution of the above cyanohydrin (5.87 g, 25.1 mmol) in $CHCl_3$ (50 mL) was added dropwise and stirring was continued for an additional 2 h. The mixture was then concentrated in vacuo and taken up in ethanol (60 mL). The solution was refluxed in the presence of 2-aminophenol (3.01 g) overnight. The ethanol was removed and the residue taken up in EtOAc, washed twice with 15% NaOH, 10% HCl, $NaHCO_3$ and brine and dried ($MgSO_4$). Flash chromatography afforded the desired compound 16 as an orange syrup (4.81 g, 59%) which was used without further purification. An analytical sample was obtained by recrystallization from 30% EtOAc in hexanes. HPLC (system A) 99%, (system D) 99%: IR (KBr) υ 1692 cm$^{-1}$; $^1$H-NMR (400 MHz, DMSO-$d_6$), 1:1 mixture of diastereomers at $P_1$, δ 7.75–7.68 (m, 2H), 7.42–7.19 (m, 8H), 6.22 and 6.10 (2×d, J=6.0 and 5.4 Hz, 1H), 5.03–4.71 (m, 3H), 4.14–4.01 (m, 1H), 1.20 and 1.11 (2×d, J=6.7 and 7.0 Hz, 3H); FAB MS m/z: 327 (MH$^+$); HRMS calcd for $C_{18}H_{19}N_2O_4$ (MH$^+$) 327.1345, found: 327.1355; Anal ($C_{18}H_{18}N_2O_4$) C, H, N.

(2S)-2-(benzyloxycarbonylamino)-1-(oxazolo[4,5,b]pyridin-2-yl)-1-propanol (17).

This material was prepared as a 1:1 mixture of isomers in 12% yield from the above cyanohydrin (978 mg, 4.18 mmol) and 2-amino-3-hydroxypyridine (505 mg, 4.60 mmol) using the procedure described above for compound 16. An analytical sample was obtained by recrystallization from EtOAc in hexanes (one isomer). mp: 159–161° C.; IR (KBr) υ 1719, 1699 cm$^{-1}$; $^1$H-NMR (400 MHz, DMSO-$d_6$) δ 8.53 (dd, J=4.8, 1.2 Hz, 1H), 8.18 (d, J=7.8 Hz, 1H), 7.44 (dd, J=8.1, 5.1 Hz, 1H), 7.39–7.08 (m, 6H), 6.33 (d, J=6.0 Hz, 1H), 5.00–4.82 (m, 2H), 4.74 (m, 1H), 4.10–4.00 (m, 1H), 1.21 (d, J=6.7 Hz, 3H); $^{13}$C-NMR (100.6 MHz, DMSO-$d_6$) δ 169.34, 155.32, 154.73, 146.08, 142.32, 136.99, 128.21, 127.59, 127.37, 120.57, 119.04, 69.99, 64.99, 49.91, 16.31; FAB MS m/z: 328 (MH$^+$); HRMS calcd for $C_{17}H_{18}N_3O_4$ (MH$^+$) 328.1297, found: 328.1286; Anal ($C_{17}H_{17}N_3O_4$) C, H, N.

(2S)-2-(benzyloxycarbonylamino)-1-(4-methylbenzo[d][1,3]oxazol-2-yl)-1-propanol (18).

This material was prepared as a 1:1 mixture of isomers in 35% yield from the above cyanohydrin (707 mg, 3.02 mmol) and 2-amino-m-cresol (409 mg, 3.32 mmol) using the procedure described above for compound 16. An analytical sample was obtained by recrystallization from EtOAc in hexanes (1.3:1 mixture of isomers). mp: 98° C.; IR (KBr) υ 1701, 1690 cm$^{-1}$; $^1$H-NMR (400 MHz, $CDCl_3$) δ 7.38–7.20 (m, 7H), 7.15–7.10 (m, 1H), 5.39 and 5.29 (2×d, J=7.9 and 5.4 Hz, 1H), 5.15–4.90 (m, 3H), 4.40 and 4.23 (2×br s, 2H), 2.58 (S, 3H), 1.34 and 1.14 (2×d, J=6.7 and 7.0 Hz, 3H); $^{13}$C-NMR (100.6 MHz, $CDCl_3$) δ 164.82, 164.22, 156.28, 156.12, 150.72, 150.65, 139.40, 136.27, 130.61, 130.43, 128.51, 128.40, 128.14, 128.01, 127.91, 125.20, 125.14, 125.04, 124.98, 108.20, 108.13, 71.02, 70.62, 66.96, 66.77, 50.45, 50.27, 17.35, 16.39, 12.24; FAB MS m/z: 341 (MH$^+$); HRMS calcd for $C_{19}H_{21}N_2O_4$ (MH$^+$) 341.1501, found: 341.1490; Anal ($C_{19}H_2ON_2O_4$) C, H, N.

(2S)-2-(benzyloxycarbonylamino)-1-(5-methylbenzo[d][1,3]oxazol-2-yl)-1-propanol (19).

This material was prepared as a 1:1 mixture of isomers in 53% yield from the above cyanohydrin (1.10 g, 4.70 mmol) and 2-amino-p-cresol (636 mg, 5.17 mmol) using the procedure described above for compound 16. An analytical sample was obtained by recrystallization from EtOAc in hexanes (7 : 1 mixture of isomers). mp: 134–135° C.; IR (KBr) υ 1718, 1691 cm$^{-1}$; $^1$H-NMR (400 MHz, $CDCl_3$) δ 7.47–7.09 (m, 8H), 5.47 (d, J=8.6 Hz, 1H), 5.12–4.87 (m, 4H), 4.54–4.30 (m, 1H), 2.44 (s, 3H), 1.32 and 1.13 (2×d, J=6.7 and 6.7 Hz, 3H); $^{13}$C-NMR (100.6 MHz, $CDCl_3$) δ 165.90, 165.19, 156.09, 149.04, 140.24, 136.28, 134.38, 128.34, 128.09, 127.91, 126.32, 119.87, 119.69, 110.23, 70.84, 70.57, 66.92, 66.67, 50.48, 50.29, 21.34, 17.24, 15.32; FAB MS m/z: 341 (MH$^+$); HRMS calcd for $C_{19}H_{21}N_2O_4$ (MH$^+$) 341.1501, found: 341.1490; Anal ($C_{19}H_{20}N_2O_4$) C, H, N.

(2S)-2-(benzyloxycarbonylamino)-1-(6-methylbenzo[d][1,3]oxazol-2-yl)-1-propanol (20).

This material was prepared as a 1:1 mixture of isomers in 71% yield from the above cyanohydrin (1.44 g, 6.15 mmol) and 6-amino-m-cresol (832 mg, 6.77 mmol) using the procedure described above for compound 16. An analytical sample was obtained by recrystallization from EtOAc in hexanes (8:1 mixture of isomers). mp: 108–109° C.; IR (KBr) υ 1692 cm$^{-1}$; $^1$H-NMR (400 MHz, $CDCl_3$) δ 7.54 (d, J=8.3 Hz, 1H), 7.36–7.10 (m, 7H), 5.40 and 5.32 (d, J=8.9 and 8.9 Hz, 1H), 5.14–4.85 (m, 3H), 4.42–4.28 (m, 2H), 2.47 (s, 3H), 1.33 and 1.14 (2×d, J=6.7 and 6.7 Hz, 3H); $^{13}$C-

NMR (100.6 MHz, CDC1$_3$) δ 165.08, 156.11, 151.24, 137.95, 136.28, 135.76, 128.52, 128.16, 127.99, 127.90, 125.89, 125.79, 119.38, 119.20, 111.09, 70.99, 70.69, 66.99, 66.76, 50.55, 50.26, 21.70, 17.29, 15.38; FAB MS m/z: 341 (MH$^+$); HRMS calcd for C$_{19}$H$_{21}$N$_2$O$_4$ (MH$^+$) 341.1501, found: 341.1490; Anal (C$_{19}$H$_{20}$N$_2$O$_4$) C, H, N.

(2S)-2-(benzyloxycarbonylamino)-1-(7-methylbenzo[d][1,3]oxazol-2-yl)-1-propanol (21).

This material was prepared as a 1:1 mixture of isomers in 57% yield from the above cyanohydrin (609 mg, 2.60 mmol) and 6-amino-o-cresol (330 mg, 2.60 mmol) using the procedure described above for compound 16. An analytical sample (1.2:1 mixture of isomers) was obtained by flash chromatography (30% EtOAc in hexanes). oil; IR (neat) υ 1705 cm$^{-1}$; $^1$H-NMR (400 MHz, CDCl$_3$) δ 7.50 (m, 1H), 7.35–7.10 (m, 7H), 5.50 and 5.38 (2×d, J=8.9 and 8.3 Hz, 1H), 5.15–4.90 (m, 3H), 4.41 (s, 1H), 2.36 (5, 3H), 1.35 and 1.14 (2×d, J=6.7 and 7.0 Hz, 3H); $^{13}$C-NMR (100.6 MHz, CDCl$_3$) δ 165.41, 164.85, 156.29, 156.12, 150.14, 139.67, 136.28, 128.50, 128.39, 128.13, 127.97, 127.84, 126.36, 126.31, 124.59, 124.51, 121.54, 117.28, 117.12, 70.99, 70.56, 66.96, 66.71, 50.42, 50.25, 17.41, 15.26, 15.08; FAB MS m/z: 341 (MH$^+$); HRMS calcd for C$_{19}$H$_{21}$N$_2$O$_4$ (MH$^+$) 341.1501, found: 341.1490; Anal (C$_{19}$H$_{20}$N$_2$O$_4$) C, H, N.

Example 5

Preparation of Unnatural Amino Acids (according to scheme 6)

(4S)-3-[2-(1-adamantyl)acetyl]-4-isopropyl-1,3-oxazolan-2-one (29).

1-Adamantaneacetic acid (1.0 g, 5.14 mmol) was dissolved in CH$_2$Cl$_2$ (15 mL) containing 1 drop of DMF. The mixture was stirred magnetically at 5° C. under an atmosphere of nitrogen and oxalyl chloride (1.1 equiv., 0.72 g, 496 μL, 5.66 mmol) was added dropwise over 20 min. After 2 h, dichloromethane was evaporated under vacuum. The residual oil was dissolved in benzene (10 mL) and concentrated to afford compound 28 (1.09 g, 100%) as a pale yellow oil which was used as such in the next reaction. To a solution of (4S)-(−)-4-isopropyl-2-oxazolidinone (0.66 g, 5.14 mmol) in anhydrous THF (10 mL) at −40° C. was added dropwise n-BuLi (3.22 mL, 1.6 M in hexanes, 5.14 mmol). After 30 min at −40° C., the reaction mixture was cooled to −78° C. The crude acid chloride 28 (1.09 g, 5.14 mmol) dissolved in THF (1 mL) was added dropwise. The mixture was then stirred magnetically at 0° C. for 1 h. Ethyl acetate was added and the organic phase was washed with 20% aqueous citric acid, saturated aqueous NaHCO$_3$, dried (MgSO$_4$), filtered and concentrated. The residual solid was purified by flash chromatography on silica gel, eluting with hexane/ethyl acetate (5/1) to provide pure 29 (1.26 g, 80%) as a white solid: mp 105–107° C.; [α]$_D^{22}$+62° (c 1.54, MeOH); $^1$H-NMR (400 MHz, CDCl$_3$) δ 4.48–4.44 (m, 1H), 4.24–4.16 (m, 2H), 2.91 (d, J=14 Hz, 1H), 2.71 (d, J=14 Hz, 1H), 2.38–2.33 (m, 1H), 2.00–1.94 (m, 3H), 1.75–1.61 (m, 12H), 0.92 (d, J=7.5 Hz, 3H), 0.89 (d, J=7.5 Hz, 3H); $^{13}$C-NMR (100.6 MHz, CDCl$_3$) δ 171.21, 154.08, 62.84, 58.54, 46.71, 42.23, 36.73, 33.81, 28.63, 28.53, 18.04, 14.68; FAB MS m/z: 306 (MH$^+$); HRMS calcd for C$_{18}$H$_{28}$NO$_3$ (MH$^+$) 306.2069, found: 306.2058; Anal (C$_{18}$H$_{27}$NO$_3$) C, H, N.

(2S)-2-(1-adamantyl)-2-azidoethanoic acid (31).

The oxazolidinone 29 (4.2 g, 13.7 mmol) was dissolved in THF (15 mL) and was added dropwise over 15 min to a solution of potassium bis(trimethylsilyl)amide (20.1 mL, 0.69 M in THF, 13.9 mmol) at −78° C. After 45 min at −78° C., 2,4,6-triisopropylbenzenesulfonyl azide (4.9 g, 15.8 mmol) in THF (10 mL) at −78° C. was added in one portion to the enolate. After 5 min, glacial acetic acid (4.6 equiv, 3.8 g, 3.61 mL, 63.2 mmol) was added and the mixture was stirred at 40° C. for 1 h. Tetrahydrofuran was evaporated under reduced pressure and the residue was dissolved in a mixture of EtOAc and water. The organic phase was washed with saturated aqueous NaHCO$_3$, followed by brine, dried (MgSO$_4$), filtered and concentrated. The residual oil was dissolved in 75 mL of hexane/ethyl acetate (2/1). After 16 h at 25° C., the white precipitate was removed by filtration and the filtrate was concentrated to give an oily residue which was filtered through a pad of silica, washed with hexane/ethyl acetate (8/1). This material (crude 30, 1.3 g, 27%) was dissolved in THF/water (70 mL, 3/1) and H$_2$O$_2$ (4 equiv, 30%, 1.69 mL, 15 mmol) was added at 0° C. followed by LiOH·H$_2$O (2.1 equiv, 0.33 g, 7.88 mmol). After 45 min, 10% aqueous Na$_2$S$_2$O$_3$ (48 mL) and solid NaHCO$_3$ (0.22 g) were added. The reaction mixture was concentrated and ca 50 mL of water was added. The aqueous phase was washed with chloroform (4 times), acidified at 0° C. with 15% HCl, and extracted with EtOAc (3 times). The combined EtOAc extracts were dried (MgSO$_4$), filtered and concentrated to provide compound 31 (0.79 g, 90% from crude 30) as a white solid: mp 110–112° C.; [α]$_D^2$−36° (c 1.60, MeOH); $^1$H-NMR (400 MHz, CDCl$_3$) δ 3.60 (s, 1H), 2.16–2.00 (m, 3H), 1.76–1.62 (m, 12H); $^{13}$C-NMR (100.6 MHz, CDCl$_3$) δ 174.19, 72.51, 38.68, 37.50, 36.51, 28.19; FAB MS m/z: 236 (MH$^+$); HRMS calcd for C$_{12}$H$_{18}$N$_3$O$_2$ (MH$^+$) 236.1399, found: 236.1389; Anal (C$_{12}$H$_{17}$N$_3$O$_2$) C, H, N.

Benzyl 4-[(4S)-4-isopropyl-2-oxo-1,3-oxazolan-3-yl]-2,2-dimethyl-4-oxobutanoate (34).

n-Butyllithium (2.4 mL, 1.6 M in hexanes, 3.9 mmol) was added dropwise to a solution of (4S)-(−)-4-isopropyl-2-oxazolidinone (0.5 g, 3.9 mmol) in THF (5 mL) at −40° C. under an atmosphere of nitrogen. After 30 min at −40° C., the reaction mixture was cooled to −78° C. and 2,2-dimethylsuccinic anhydride (0.5 g, 3.9 mmol) dissolved in THF (2 mL) was added dropwise. The mixture was then stirred magnetically at 0° C. for 1 h. Ethyl acetate was added and the organic phase was washed with 20% aqueous citric acid, brine, dried (MgSO$_4$), and concentrated to afford crude 33 as a pale yellow solid (1.0 g) which was dissolved in acetonitrile (5 mL) at 0° C. 1,8-Diazabicyclo[5.4.0]undec-7-ene (0.59 g, 583 μL, 3.9 mmol) and benzyl bromide (0.67 g, 463 μL, 3.9 mmol) were added and the reaction mixture was then stirred at 25° C. for 16 h. Acetonitrile was evaporated in vacuo. The residue was partitioned between EtOAc and 20% aqueous citric acid. The organic phase was washed with water, brine, dried (MgSO$_4$), filtered and concentrated. The residue was purified by flash chromatography on silica gel eluting with hexane/ethyl acetate (4/1) to give pure 34 (0.88 g, 61% from 32) as a colorless oil; [α]$_D^{22}$+560 (c 1.30, CHCl$_3$); $^1$H-NMR (400 MHz, CDCl$_3$) δ 7.31–7.28 (m, 5H), 5.11 (m, 2H), 4.36–4.32 (m, 1H), 4.23–4.15 (m, 2H), 3.25 (s, 2H), 2.30–2.22 (m, 1H), 1.33 (s, 3H), 1.31 (s , 3H), 0.86 (d, J=7 Hz, 3H), 0.81 (d, J=7 Hz, 3H); $^{13}$C-NMR (100.6 MHz, CDCl$_3$) δ 176.73, 170.75, 154.03, 136.25, 128.35, 127.88, 66.24, 63.44, 58.27, 45.31, 40.24, 28.31, 25.62, 25.58, 17.84, 14.56; FAB MS m/z: 348 (MH$^+$); HRMS calcd for C$_{19}$H$_{26}$NO$_5$ (MH$^+$) 348.1811, found: 348.1822; Anal (C$_{19}$H$_{25}$NO$_5$) C, H, N.

Benzyl 3-azido-2,2-dimethylsuccinic acid (36).

The oxazolidinone 34 (8.67 g, 24.9 mmol) was dissolved in THF (27 mL) and was added dropwise over 15 min to a solution of potassium bis(trimethylsilyl)amide (36.5 mL, 0.69 M in THF, 25.2 mmol) at −78° C. After 45 min at −78° C., 2,4,6-triisopropylbenzenesulfonyl azide (8.89 g, 28.7 mmol) in THF (15 mL) at −78° C. was added in one portion to the enolate. After 5 min, glacial acetic acid (4.6 equiv, 6.90 g, 6.56 mL, 0.12 mol) was added and the mixture was stirred at 35–40° C. for 90 min. Tetrahydrofuran was evaporated under reduced pressure and the residue was dissolved in a mixture of EtOAc and water. The organic phase was washed with saturated aqueous $NaHCO_3$, brine, dried ($MgSO_4$), filtered and concentrated. The residue was dissolved in 150 mL of hexane/ethyl acetate (2/1). After 16 h at 25° C., the white precipitate was removed by filtration and the filtrate was concentrated to give an oil which was filtered through a pad of silica and rinsed with hexane/ethyl acetate (5/1). This pale yellow oil (crude 35, 5.37 g, 55%) was dissolved in THF/water (260 mL, 3/1) and $H_2O_2$ (4 equiv, 30%, 6.24 mL, 55 mmol) was added at 0° C., followed by $LiOHH_2O$ (2.1 equiv, 1.22 g, 29 mmol). After 45 min, 10% aqueous $Na_2S_2O_3$ (175 mL) and solid $NaHCO_3$ (0.81 g) were added. Tetrahydrofuran was evaporated and the aqueous phase was extracted with chloroform (continuous liquid-liquid extraction, 24 h). The aqueous phase was then acidified with concentrated HCl at 0° C., and extracted with EtOAc (3 times). The combined EtOAc extracts were dried ($MgSO_4$), filtered and concentrated. The residual oil was purified by flash chromatography on Merck silica gel eluting with ethyl acetate/acetic acid (400/1) to give compound 36 (0.82 g, 21%) as a colorless oil; $[\alpha]_D^{22}$ −74° (c 1.43, $CHCl_3$); $^1$H-NMR (400 MHz, $CDCl_3$) δ 7.39–7.32 (m, 5H), 5.20–5.12 (m, 2H), 4.48 (s, 1H), 1.34 (s, 3H), 1.29 (s, 3H); $^{13}$C-NMR (100.6 MHz, $CDCl_3$) δ 174.74, 173.86, 135.42, 128.56, 128.35, 128.13, 67.86, 67.18, 45.98, 23.01, 20.29; FAB MS m/z: 278 (MH$^+$); HRMS calcd for $C_{13}H_{16}N_3O_4$ (MH$^+$) 278.1141, found: 278.1130; Anal ($C_{13}H_{15}N_3O_4$) C, H, N.

Example 6

N1-(3,3,3-trifluoro-1-methyl-2-oxopropyl)-(2S)-2-((1S)-2-methyl-1-[((1S)-2-methyl-1-[(methylcarboxamido)methyl] carboxamidopropyl) carboxamido]propylcarboxamido) butanediamide (37, Table 1)

This compound was prepared on solid phase using the activated ketone resin (Example 1). Final purification was performed by preparative HPLC. HPLC (system A) 97%, (system B) 98%; IR (KBr) υ 3400–3000 (br), 1637, 1548 cm$^{-1}$; $^1$H-NMR (400 MHz, DMSO-d$_6$), 1:1 mixture of hydrate/non-hydrate, 1:1 mixture of diastereomers at P$_1$, δ 8.51 and 8.49 (d, J=6.0 and 6.0 Hz, 0.5H), 8.08–8.02 (m, 2H), 7.83–7.76 (m, 2H), 7.47–7.30 (m, 1.5H), 6.95-6.88 (m, 2H), 4.61–4.52 (m, 1.5H), 4.26–4.06 (m, 2.5H), 3.79–3.67 (m, 2H), 2.67–2.32 (m, 2H), 1.99–1.93 (m, 2H), 1.85 (s, 3H), 1.26 and 1.25 (d, J=4.1 and 3.8 Hz, 1.5H), 1.06 (d, 6.7 Hz, 1.5H), 0.84–0.79 (m, 12H); FAB MS m/z: 553 (MH$^+$); HRMS calcd for $C_{22}H_{36}F_3N_6O_7$ (MH$^+$) 553.2597, found: 553.2617.

Example 7

N1-(3,3,3-trifluoro-1-methyl-2-oxopropyl)-(2S)-6-amino-2-((1S)-1-[((1S)-1-[(1S)-2-hydroxy-1-(methylcarboxamido) ethyl]carboxamido-2-(4-hydroxyphenyl)ethyl)carboxamido]-2-methylpropylcarboxamido)hexanamide (38, Table 1)

This compound was prepared on solid phase using the activated ketone resin (Example 1). Final purification was performed by preparative HPLC. HPLC (system A) 98%, (system B) 99%; IR (KBr) υ 3500–2800 (br), 1643, 1516 cm$^{-1}$; $^1$H-NMR (400 MHz, DMSO-d$_6$), 3:1 mixture of hydrate/non-hydrate, 1:1 8.68 (d, J=5.7 and 5.7 Hz, 0.25H), 8.08 and 8.03 (d, J=8.0 and 8.0 Hz, 1H), 7.91 (t, J=7.1 Hz, 2H), 7.75 (quartet, J=7.9 Hz, 1H), 7.63 (br s, 3H), 7.57 and 7.56 (d, J=10.9 and 8.9 Hz, 1H), 7.02–6.95 (m, 2.75H), 6.61 (d, J=8.3 Hz, 2H), 4.94 (m, 1 H), 4.71-4.62 (m, 0.25H), 4.43 (m, 1H), 4.26 (m, 2H), 4.13 (m, 1.75H), 3.48 (t, J=5.7 Hz, 2H), 2.92 (m, 1H), 2.74 (br m, 3H), 1.95 (q, J=6.8 Hz, 1H), 1.83 (s, 3H), 1.62 (m, 1H), 1.51 (m, 2H), 1.08 (m, 3H), 1.08 and 1.07 (d, J=6.7 and 6.6 Hz, 3H), 0.86–0.81 (m, 6H); FAB MS m/z 661 (MH$^+$); HRMS calcd for $C_{29}H_{44}F_3N_6O_8$ (MH$^+$) 661.3173, found: 661.3195.

Example 8

N1-(3,3,3-trifluoro-1-methyl-2-oxopropyl)-(2S)-2-[((1S)-2-methyl-1-[(1S)-2-methyl-1-(methylcarboxamido)propyl]carboxamidopropyl) carboxamido]butanediamide (39, Table 1)

This compound was prepared in solution using standard coupling methods from 3 (Example 3) and oxidation of the trifluoromethyl alcohol with the Moffatt-Pfitzner method. Final purification was performed by preparative HPLC. HPLC (system A) 100%, (system B) 100%; IR (KBr) υ 3600–2800, 1636, 1546 cm$^{-1}$; $^1$H-NMR (400 MHz, DMSO-d$_6$), 3:1 mixture of hydrate/non-hydrate, 1:1 mixture of diastereomers at P$_1$, δ 8.53 (m, 0.25H), 8.09 and 8.06 (d, J=7.9 and 7.4 Hz, 1H); 7.89 and 7.87 (d, J=4.9 and 5.4 Hz, 1H), 7.72 and 7.70 (d, J=4.5 and 4.0 Hz, 1H), 7.46 (d, J=9.8 Hz, 0.4H), 7.37–7.30 (m, 1.5H), 6.96–6.89 (m, 2.6H), 4,54 (m, 1H), 4.21–4.06 (m, 3H), 2.48–2.34 (m, 2H), 2.00–1.91 (m, 2H), 1.871 and 1.868 (s, 3H), 1.27 and 1.25 (d, J=4.5 and 3.9 Hz, 0.75H), 1.06 (d, 6.9 Hz, 2.25H), 0.84–0.80 (m, 12H); FAB MS m/z: 496 (MH$^+$); HRMS calcd for $C_{20}H_{33}F_3N_5O_6$ (MH$^+$) 496.2382, found: 496.2387.

Example 9

N1-(3,3,3-trifluoro-1-methyl-2-oxopropyl)-(2S)-2-{[(1S)-2-methyl-1-[(methylcarboxamido)propyl] carboxamido}butanediamide (40, Table 1)

This compound was prepared by solution using standard coupling methods. Final oxidation of the trifluoromethyl alcohol was accomplished with the Moffatt-Pfitzner method. HPLC (system A) 100%, (system D) 98%; IR (KBr)υ 1685, 1655, 1627 cm$^{-1}$; $^1$H-NMR (400 MHz, DMSO-d$_6$), 7:1 mixture of hydrate/non-hydrate, 1:1 mixture of diastereomers at P$_1$, δ 8.19 and 8.11 (2×d, J=7.6 and 7.6 Hz, 1H), 7.94 (m, 1H), 7.38 (m, 2H), 6.91 (m, 3H), 4.51 (m, 1H), 4.10 (m, 2H), 2.40 (m, 1H), 1.94 (m, 1H), 1.89 and 1.87 (2×s, 3H), 1.26 (m, 0.4H), 1.07 (d, J=5.4 Hz, 2.6H), 0.83 (t, J=6.3 Hz, 6H); FAB MS m/z: 397 (MH$^+$), 415 (M+19); HRMS calcd for $C_{15}H_{24}F_3N_4O_5$ (MH$^+$) 397.1699, found: 397.1712.

Example 10

N1-(3,3,3-trifluoro-1-methyl-2-oxopropyl)-(2S)-2-(methylcarboxamido)butanediamide (41, Table 1)

This compound was prepared in solution using standard coupling methods from 3 (Example 3) and oxidation of the trifluoromethyl alcohol with the Moffatt-Pfitzner method. HPLC (system A) 99%, (system D) 99%; IR (KBr) υ 3387, 1696, 1653 cm$^{-1}$; $^1$H NMR (400 MHz, DMSO-d$_6$) 1:1 mixture of diastereoisomers at P$_1$, δ 8.65 and 8.59 (2×d, J=6.1 and 5.7 Hz, 0.1H), 8.09 and 8.04 (2×d, J=7.9 and 7.9

Hz, 1H), 7.53 and 7.36 (2×d, J=9.2 and 9.2 Hz, 1H), 7.31 (br s, 1H), 6.96–6.87 (m, 3H), 4.61–4.47 (m, 1H), 4.05–4.15 (m, 1H), 2.49 and 2.31 (m, 2H), 1.25 (dd, J=7.0 and 4.4 Hz, 0.3H), 1.07 (dd, J=7.0 and 3.5 Hz, 2.7H); FAB MS m/z: 298 (MH$^+$), 316 (M+19); HRMS calcd for $C_{10}H_{15}F_3N_3O_4$ (MH$^+$) 298.1015, found: 298.1026.

Example 11

N1-(3,3, 3-trifluoro-(1R)-methyl-2-oxopropyl)-(2S)-2-[(1S)-2-methyl-1-(methylcarbox-amido)propyl] carboxamidobutanediamide (42, Table 1)

This compound was prepared in solution using standard coupling methods from 3 (Example 3) and oxidation of the trifluoromethyl alcohol with the Moffatt-Pfitzner method. Final purification was performed by preparative HPLC. HPLC (system A) 99%, (system D) 97%; IR (KBr) υ 1685, 1671, 1638 cm$^{-1}$; $^1$H NMR (400 MHz, DMSO-d$_6$), 20:1 mixture of hydrate/non-hydrate, 6 8.11 (d, J=7.5 Hz, 1H), 7.95 (d, J=8.0 Hz, 1H), 7.35 (br s, 1H), 7.32 (d, J=9.3 Hz, 1H), 6.92 (br s, 1H), 4.52 (q, J=7.2 Hz, 1H), 4.11 (m, 2H), 2.45 (m, 2H), 1.95 (m, 1H), 1.26 (d, J=6.9 Hz, 0.05H), 1.07 (d, J=6.9 Hz, 2.95H), 0.84 (t, J=6.6 Hz, 6H); FAB MS m/z: 397.3 (MH$^+$), 415.3 (M+19); HRMS calcd for $C_{15}H_{23}F_3N_4O_3$ (MH$^+$) 397.1699, found: 397.1707.

Example 12

N1-(3,3,3-trifluoro-(1S)-methyl-2-oxopropyl)-(2S)-2-{[(1S)-2-methyl-1-(methylcarboxamido)propyl] carboxamido}butanediamide (43, Table 1)

This compound was separated from 42 by preparative HPLC. HPLC (system A) 97%, (system D) 100%; IR (KBr)υ 1685, 1663, 1626 cm$^{-1}$; $^1$H-NMR (400 MHz, DMSO-d$_6$) hydrated form only, δ 8.19 (d, J=7.5 Hz, 1H), 7.93 (d, J=8.4 Hz, 1H), 7.43 (d, J=9.6 Hz, 1H), 7.34 (br s, 1H), 6.90 (br s, 1H), 4.51 (q, J=6.9 Hz, 1H), 4.11 (m, 2H), 2.45 (m, 2H), 1.93 (m, 1H), 1.06 (d, J=6.9 Hz, 3H), 0.84 (m, 6H); FAB MS m/z: 397 (MH$^+$), 415 (M+19); HRMS calcd for $C_{15}H_{23}F_3N_4O_3$ (MH$^+$) 397.1699, found: 397.1712.

Example 13

N1-(1-ethyl-3,3,3-trifluoro-2-oxopropyl)-(2S)-2-[((1S)-2-methyl-1-[(1S)-2-methyl-1-(methylcarboxamido)propyl] carboxamidopropyl) carboxamido]butanediamide (44, Table 1)

This compound was prepared on solid phase using the activated ketone resin substituted as the ethyl analog (Example 1). Final purification was performed by preparative HPLC. HPLC (system A) 100%, (system D) 100%; IR (KBr) υ 1640 cm$^{-1}$; $^1$H-NMR (400 MHz, DMSO-d$_6$), 7:1 mixture of hydrate/non-hydrate, 1:1 mixture of diastereomers at P$_1$, δ 8.55–8.47 (m, 0.14H), 8.09 and 8.05 (2×d, J=7.3 and 7.3 Hz, 1H), 7.90–7.87 (m, 1H), 7.71–7.68 (m, 1H), 7.40–7.24 (m, 2H), 6.92–6.77 (m, 3H), 4.59–4.52 (m, 1H), 4.23–4.15 (m, 2H), 3.96–3.87 (m, 1H), 2.67–2.32 (m, 2H), 2.01–1.90 (m, 2H), 1.87 and 1.86 (2×s, 3H), 1.79–1.71 (m, 1H), 1.40–1.28 (m, 1H), 0.89–0.74 (m, 15H); FAB MS m/z: 510 (MH$^+$), 528 (M+19); HRMS calcd for $C_{21}H_{35}F_3N_5O_6$ (MH$^+$) 510.2539, found: 510.2558.

Example 14

N1-(1-(3,3,3-trifluoro-1-propyl-2-oxopropyl)-(2S)-2-[((1S)-2-methyl-1-[(1S)-2-methyl-1-(methylcarboxamido)propyl]carboxamidopropyl) carboxamido]butanediamide (45, Table 1)

This compound was prepared by the same procedure as for 3 (Example 3), except 1-nitroethane was replaced by 1-nitrobutane. Standard solution coupling conditions were used to prepare the peptide inhibitor with final oxidation of the trifluoromethyl alcohol using Moffatt-Pfitzner method. Purification was performed by preparative HPLC. HPLC (system A) 89%, (system D) 99%: IR (KBr) υ 3280, 1663, 1637, 1546 cm$^{-1}$; $^1$H NMR (400 MHz, DMSO-d$_6$), 7:1 mixture of hydrate/non-hydrate, 1:1 mixture of diastereomers at P$_1$, δ 8.50 (m, 0.25H), 8.18 (d, J=7.3 Hz, 0.12H), 8.07 (m, 1H), 8.02 (d, J=7.95 Hz, 0.25H), 7.89 and 7.88 (2×d, J=8.6 and 8.9 Hz, 1H), 7.77 (d, J=8.3 Hz, 0.12H), 7.70 (d, J=8.6 Hz, 1H), 7.46–7.24 (m, 2H), 6.97–6.72 (m, 2.7H), 4.63–4.51 (m, 1H), 4.30 and 4.28 (2×d, J=6.7 and 6.7 Hz, 0.12H), 4.24–4.13 (m, 2H), 4.09–3.96 (m, 1H), 2.50–2.32 (m, 2H), 2.02–1.91 (m, 2H), 1.87 (s, 3H), 1.72–1.57 (m, 1H), 1.43–1.21 (m, 2H), 1.18–1.04 (m, 1H), 0.89–0.75 (m, 15H); FAB MS m/z: 524 (MH$^+$), 542 (M+19); HRMS calcd for $C_{22}H_{37}F_3N_5O_6$ (MH$^+$) 524.2696, found: 524.2705.

Example 15

N1-(3,3,3-trifluoro-1-methyl-2-oxopropyl)-(2S)-2-[((1S)-2-methyl-1-[(1S)-2-methyl-1-(methylcarboxamido)propyl] carboxamidopropyl) carboxamido]pentanediamide (46, Table 2)

This compound was prepared on solid phase using the activated ketone resin (Example 1). Final purification was performed by preparative HPLC. HPLC (system A) 86%, (system D) 82%; IR (KBr) υ 3281, 3079, 1647 cm$^{-1}$; $^1$H NMR (400 MHz, DMSO-d$_6$), 2:3 mixture of hydrate/non-hydrate, 1.2:1 mixture of diastereoisomers at P$_1$, δ 8.72 (d, J=5.7 Hz, 0.16H), 8.70 (d, J=5.7 Hz, 0.18H), 7.90–8.02 (m, 0.8H), 7.90 (d, J=8.9 Hz, 1H), 7.68–7.74 (m, 1H), 7.56–7.61 (m, 0.3H), 7.10–7.21 (m, 1H), 6.90–7.00 (m, 1H), 6.70–6.75 (m, 1H), 4.60–4.69 (m, 0.4H), 4.07–4.29 (m, 3.7H), 2.00–2.09 (m, 2H), 1.90–1.98 (m, 2H), 1.86 (s, 3H), 1.83–1.61 (m, 2H), 1.28 (d, J=7.0 Hz, 0.5H), 1.27 (d, J=7.0 Hz, 0.6H), 1.08 (d, J=6.5 Hz, 1.4H), 1.07 (d, J=6.4 Hz, 1.2H), 0.81–0.84 (m, 12H); FAB MS m/z: 510 (MH$^+$); HRMS calcd for $C_{21}H_{35}F_3N_5O_6$ (MH$^+$) 510.2539, found: 510.2521.

Example 16

(3S)-3-[((1S)-2-methyl-1-[(1S)-2-methyl-1-(methylcarboxamido)propyl]carboxamidopropyl) carboxamido]-3-[(3,3,3-trifluoro-1-methyl-2-oxopropyl)carbamoyl]propanoic acid (47, Table 2)

This compound was prepared on solid phase using the activated ketone resin (Example 1). Final purification was performed by preparative HPLC. HPLC (system A) 96%, (system B) 97%; IR (KBr) υ 3500–2800 (br), 1639, 1546 cm$^{-1}$; $^1$H-NMR (400 MHz, DMSO-d$_6$), hydrated form only, 1:1 mixture of diastereomers at P$_1$, δ 12.29 (br s, 1H), 8.22 and 8.14 (d, J=7.8 and 7.9 Hz, 1H), 7.89 (m, 1H), 7.70 (m, 1H), 7.40 and 7.35 (d, J=8.8 and 9.4 Hz, 1H), 6.93 (t, J=7.8 Hz, 2H), 4.53 (m, 1H), 4.17 (m, 2H), 4.11 (q, J=6.9 Hz, 1H), 2.67–2.58 (m, 1H), 2.47 (m, 1H), 1.94 (m, 2H), 1.87 (s, 3H), 1.06 (m, 3H), 0.83 (m, 12H); FAB MS m/z: 497 (MH$^+$); HRMS calcd for $C_{20}H_{32}F_3N_4O_7$ (MH$^+$) 497.2223; found: 497.2237.

Example 17

N1-[(1S)-1-((1S)-2-hydroxy-1-[(3,3,3-trifluoro-1-methyl-2-oxopropyl)carbamoyl]ethyl-carbamoyl)-2-methylpropyl]-(2S)-3-methyl-2-(methylcarboxamido) butanamide (48, Table 2)

This compound was prepared on solid phase using the activated ketone resin (Example 1). Final purification was performed by preparative HPLC. HPLC (system A) 94%, (system B) 99%; IR (KBr) υ 3500–2800, 1637, 1543 cm$^{-1}$; $^1$H-NMR (400 MHz, DMSO-d$_6$), hydrated form only, 1:1 mixture of diastereomers at P$_1$, δ 7.94 (d, J=7.9 Hz, 1H), 7.90 (d, J=8.9 Hz, 1H), 7.73 and 7.71 (d, J=5.4 and 4.9 Hz, 1H), 7.55 and 7.50 (8.9 and 9.4 Hz, 1H), 6.93 (br m, 2H), 4.31–4.10 (m, 4H), 3.57–3.47 (m, 3H), 1.97 (m, 2H), 1.87 (s, 3H), 1.09 and 1.08 (d, J=6.9 and 6.9 Hz, 3H), 0.86–0.81 (m, 12H); FAB MS m/z: 469 (MH$^+$); HRMS calcd for C$_{19}$H$_{32}$F$_3$N$_4$O$_6$ (MH$^+$) 469.2274, found: 469.2261.

Example 18

N1-(3,3,3-trifluoro-1-methyl-2-oxopropyl)-(2S)-6-amino-2-[((1S)-2-methyl-1-[(1S)-2-methyl-1-(methylcarboxamido)propyl]carboxamidopropyl) carboxamido]hexanamide (49, Table 2)

This compound was prepared on solid phase using the activated ketone resin (Example 1). Final purification was performed by preparative HPLC. HPLC (system A) 98%, (system B) 96%; IR (KBr) υ 3227, 1638, 1545, 1189 cm$^{-1}$; $^1$H NMR (400 MHz, DMSO-d$_6$), hydrated form only, 1:1 mixture of diastereomers at P$_1$, δ 7.99 (2×d, J=7.9 and 7.4 Hz, 1H), 7.88 (d, J=8.8 Hz, 1H), 7.71 and 7.70 (2×d, J=8.7 and 8.4 Hz, 1H), 7.58 (t, J=8.9 Hz, 1H), 6.99 (m, 2H), 4.29–4.09 (m, 4H), 2.73 (m, 2H), 2.00–1.92 (m, 2H), 1.93 (s, 3H), 1.63–1.46 (m, 4H), 1.28–1.25 (m, 2H), 1.09 and 1.07 (2×d, J=6.9 and 6.9 Hz, 3H), 0.85–0.82 (m, 12H); FAB MS (FAB) m/z: 510 (MH$^+$), 528 (M+19); HRMS calcd for C$_{22}$H$_{39}$F$_3$N$_5$O$_5$ (MH$^+$) 510.2903, found: 510.2888.

Example 19

N1-[(1S)-2-methyl-1-((1S)-2-(1,3-thiazol-4-yl)-1-[(3,3,3-trifluoro-1-methyl-2-oxopropyl)-carbamoyl] ethylcarbamoyl) propyl]-(2S)-3-methyl-2-(methylcarboxamido)butanamide (50, Table 2)

This compound was prepared on solid phase using the activated ketone resin (Example 1). Final purification was performed by preparative HPLC. HPLC (system A) 98%, (system D) 98%; IR (KBr) υ 3276, 3084, 1638 cm$^{-1}$; $^1$H-NMR (400 MHz, DMSO-d$_6$), 1:1.2 hydrate/non-hydrate, 1.2:1 mixture of diastereomers at P$_1$, δ 8.99 (d, J=5.4 Hz, 0.55H), 8.98 (d, J=5.4 Hz, 0.45H), 8.77 (d, J=5.7 Hz, 0.19H), 8.71 (d, J=5.7 Hz, 0.23H), 8.09–8.17 (m, 1H), 7.84–7.88 (m, 1H), 7.67–7.90 (m, 1.43H), 7.55 (d, J=8.9 Hz, 0.25H), 7.29–7.34 (m, 1H), 6.94 (br s, 0.75H), 4.58–4.73 (m, 1.5H), 4.06–4.18 (m, 2.5H), 2.97–3.17 (m, 2H), 1.86–1.93 (m, 2H), 1.86 (s, 1.65H), 1.85 (s, 1.35H), 1.22 (d, J=6.7 Hz, 0.61H), 1.21 (d, J=6.7 Hz, 0.74H), 1.07 (d, J=7.0 Hz, 0.93H), 0.98 (d, J=6.7 Hz, 0.72H), 0.76–0.80 (m, 12 H); FAB MS m/z: 536 (MH$^+$), 554 (M+19); HRMS calcd for C$_{22}$H$_{33}$F$_3$N$_5$O$_5$S (MH$^+$) 536.2154, found: 536.2170.

Example 20

N4,N4-dimethyl-N1-(3,3,3-trifluoro-1-methyl-2-oxopropyl)-(2S)-2-[((1S)-2-methyl-1-[(1S)-2-methyl-1-(methylcarboxamido)propyl] carboxamidopropyl) carboxamido]butanediamide (51, Table 2)

This compound was prepared on solid phase using the activated ketone resin (Example 1). Final purification was performed by preparative HPLC. HPLC (system A) 100%, (system B) 99%; IR (KBr) 1638 cm$^{-1}$; $^1$H-NMR (400 MHz, DMSO-d$_6$), 1:1 mixture of diastereomers at P$_1$, δ 8.56–8.49 (m, 0.1H), 8.10–8.03 (m, 0.8H), 7.89–7.86 (m, 0.8H), 7.73–7.70 (m, 0.8H), 7.44–7.41 (m, 1H), 6.95–6.80 (m, 1.5H), 4.63–4.54 (m, 1H), 4.20–4.06 (m, 3H), 2.94–2.93 (m, 3H), 2.80–2.78 (m, 3H), 2.67–2.62 (m, 2H), 1.99–1.93 (m, 2H), 1.87–1.86 (m, 3H), 1.30–1.25 (m, 0.5H), 1.07–1.06 (m, 2.5H), 0.84–0.83 (m, 12H); FAB MS m/z: 524 (MH$^+$); HRMS calcd for C$_{22}$H$_{37}$F$_3$N$_5$O$_6$ (MH$^+$) 524.2696, found: 524.2710.

Example 21

N1-(3,3,3-trifluoro-1-methyl-2-oxopropyl)-(2S)-4-methyl-2-[((1S)-2-methyl-1-[(1S)-2-methyl-1-(methylcarboxamido)propyl]carboxamidopropyl) carboxamido]pentanamide (52, Table 2)

This compound was prepared on solid phase using the activated ketone resin (Example 1). Final purification was performed by preparative HPLC. HPLC (system A) 97%, (system D) 97%; IR (KBr) υ 3268, 3080, 1632 cm$^{-1}$; $^1$H-NMR (400 MHz, DMSO-d$_6$), 1:1.2 hydrate/non-hydrate, 1.2:1 mixture of diastereomers at P$_1$, δ 8.72 (d, J=6.5 Hz, 0.25H), 8.70 (d, J=6.5 Hz, 0.3H), 7.91–8.10 (m, 1H), 7.84–7.88 (m, 1H), 7.74–7.80 (m, 1H), 7.55 (d, J=8.6 Hz, 0.2H), 7.53 (d, J=8.9 Hz, 0.25H), 6.90–6.96 (m, 1H), 4.57–4.68 (m, 0.5H), 4.26–4.39 (m, 1H), 4.15–4.21 (m, 1H), 4.05–4.14 (m, 1.4H), 1.87–1.95 (m, 2H), 1.85 (s, 3H), 1.53–1.63 (m, 1H), 1.30–1.50 (m, 2H), 1.26 (d, J=7.0 Hz, 0.8H), 1.25 (d, J=7.0 Hz, 1H), 1.07 (d, J=6.7 Hz, 0.8H), 1.06 (d, J=6.7 Hz, 0.6H), 0.78–0.88 (m, 18H); FAB MS m/z: 495 (MH$^+$); HRMS calcd for C$_{22}$H$_{38}$F$_3$N$_4$O$_5$ (MH$^+$) 495.2794, found: 495.2803; Anal (C$_{22}$H$_{37}$F$_3$N$_4$O$_5$.H$_2$O C, H, N.

Example 22

N1-[(1S)-2-methyl-1-((1S)-2-phenyl-1-[(3,3,3-trifluoro-1-methyl-2-oxopropyl)carbamoyl]-ethylcarbamoyl)propyl]-(2S)-3-methyl-2-(methylcarboxamido)butan-amide (53, Table 2)

This compound was prepared by solid phase using the activated ketone resin (Example 1). Final purification was performed by preparative HPLC. HPLC (system A) 98%, (system B) 100%; IR (KBr) υ 3280, 1636, 1546 cm$^{-1}$; $^1$H-NMR (400 MHz, DMSO-d$_6$) 1:1 mixture of diastereomers at P$_1$, δ 8.03 (m, 1H), 7.86 (m, 1H), 7.64 (m, 1H), 7.22 (m, 5H), 7.19 (m, 1H), 6.93 and 6.90 (2×d, J=14.3 and 13.7 Hz, 2H), 4.63–4.54 (m, 2H), 4.16–4.05 (m, 4H), 3.00–2.66 (m, 2H), 1.86 (s, 3H), 1.85 (m, 2H), 1.25, 1.21, 1.09 and 0.96 (4 ×d, J=7.4, 6.8, 6.9 and 7.9 Hz, 3H), 0.79 (m, 12H); FAB MS m/z: 529 (MH$^+$), 547 (M+19); HRMS calcd for C$_{25}$H$_{36}$F$_3$N$_4$O$_5$ (MH$^+$) 529.2638, found: 529.2619.

Example 23

N1-[(1S)-2-methyl-1-((1S)-2-methyl-1-[(3,3,3-trifluoro-1-methyl-2-oxopropyl)carbamoyl]-propylcarbamoyl)propyl]-(2S)-3-methyl-2-(methylcarboxamido)butanamide (54, Table 2)

This compound was prepared on solid phase using the activated ketone resin (Example 1). HPLC (system A) 84%, (system B) 83%; IR (KBr) 1633 cm$^{-1}$; $^1$H-NMR (400 MHz, DMSO-d$_6$) 1:1 mixture of diastereoisomers at P$_1$, δ 8.78 (d, J=5.5 Hz, 0.25H), 8.71 (d, J=5.5 Hz, 0.25H), 7.88–7.60 (m, 3.5H), 6.98–6.87 (m, 1H), 4.70–4.64 (m, 0.5H), 4.22–4.09 (m, 3.5H), 1.97–1.91 (m, 3H), 1.86 (s, 3H), 1.28–1.26 (m, 1.7H), 1.09–1.07 (m, 1.3H), 0.88–0.78 (m, 18H); FAB MS m/z: 481 (MH$^+$); HRMS calcd for C$_{21}$H$_{36}$F$_3$N$_4$O$_5$ (MH$^+$) 481.2638; found: 481.2627.

Example 24

N1-[(1S)-2-methyl-1-((1S)-1-[(3,3,3-trifluoro-1-methyl-2-oxopropyl)carbamoyl]ethyl-carbamoyl)propyl]-(2S)-3-methyl-2-(methylcarboxamido)butanamide (55, Table 2)

This compound was prepared on solid phase using the activated ketone resin (Example 1). Final purification was performed by preparative HPLC. HPLC (system A) 99%, (system B) 99%; IR (KBr) υ 3264, 1627, 1552 cm$^{-1}$I; $^1$H-NMR (400 MHz, DMSO-d$_6$) 1:1 mixture of diastereomers at P$_1$, δ 7.98 and 7.92 (2×d, J=7.3 and 7.3 Hz, 1H), 7.88–7.83 (m, 1H), 7.72 (d, J=8.8 Hz, 1H), 7.58 (t, J=9.4 Hz, 1H), 6.95 and 6.91 (2×br s, 2H), 4.33–4.06 (m, 4H), 1.95 (m, 2H), 1.87 (s, 3H), 1.17–1.13 (m, 3H), 1.08 (d, J=6.9 Hz, 3H), 0.85–0.81 (m, 6H); FAB MS m/z: 453 (MH$^+$), 471 (M+19); HRMS calcd for C$_{19}$H$_{32}$F$_3$N$_4$O$_5$ (MH$^+$) 453.2325, found: 453.2338.

Example 25

N1-[(1S)-2-methyl-1-((1R)-1-[(3,3,3-trifluoro-1-methyl-2-oxopropyl)carbamoyl]ethyl-carbamoyl)propyl]-(2S)-3-methyl-2-(methylcarboxamido)butanamide (56, Table 2)

This compound was separated from 55 by preparative HPLC. HPLC (system A) 99%, (system B) 99%; IR (KBr) 1634 cm$^{-1}$; $^1$H-NMR (400 MHz, DMSO-d$_6$) 1:1 mixture of diastereomers at P$_1$, δ 8.63 (d, J=5.5 Hz, 0.1H), 8.56 (d, J=4.5 Hz, 0.1H), 8.18–8.12 (m, 0.2H), 8.01 (d, J=7 Hz, 0.3H), 7.96 (d, J=7.5 Hz, 0.3H), 7.89–7.74 (m, 1.8H), 7.65 (d, J=9 Hz, 0.3H), 7.60 (d, J=9.5 Hz, 0.3H), 6.96 –6.92 (m, 1.3H), 4.68–4.59 (m, 0.3H), 4.34–4.25 (m, 1H), 4.19–4.02 (m, 2.7H), 1.98–1.89 (m, 2H), 1.86 (s, 3H), 1.31–1.29 (m, 0.8H), 1.19–1.07 (m, 5.2H), 0.86–0.82 (m, 12H); FAB MS m/z: 453 (MH$^+$); HRMS calcd for C$_{19}$H$_{32}$F$_3$N$_4$O$_5$ (MH$^+$) 453.2325; found: 453.2338.

Example 26

N4, N4-dimethyl-N1-(3,3,3-trifluoro-1-methyl-2-oxopropyl)-(2S)-2-[((1S)-1-[(1S)-2-methyl-1-(methylcarboxamido)propyl]carboxamidopropyl)carboxamido]butanediamide (57, Table 3)

This compound was prepared on solid phase using the activated ketone resin (Example 1). Final purification was performed by preparative HPLC. HPLC (system A) 100%, (system D, pH 7.4) 100%; IR (KBr) υ 3283, 1642 cm$^-$; $^1$H-NMR (400 MHz, DMSO-d$_6$), 19:1 mixture of hydrate/non-hydrate, 1:1 mixture of diastereomers at P$_1$, δ 8.05 and 8.01 (2×d, J=7.6 and 7.6 Hz, 1H), 7.91–7.82 (m, 2H), 7.43 and 7.39 (2×d, J=9.2 and 9.2 Hz, 1H), 7.01–6.80 (m, 2H), 4.61–4.52 (m, 1H), 4.22–4.00 (m, 3H), 2.94 and 2.93 (2×s, 3H), 2.80 (s, 3H), 2.71–2.59 (m, 2H), 2.00–1.90 (m, 1H), 1.87 and 1.86 (2×s, 3H), 1.73–1.61 (m, 1H), 1.57–1.45 (m, 1H), 1.27 and 1.26 (2×d, J=6.7 and 6.7 Hz, 0.15H), 1.06 (d, J=6.0 Hz, 3H), 0.87–0.78 (m, 9H); FAB MS m/z: 510.3 (MH$^+$), 528.3 (M+19); HRMS calcd for C$_{21}$H$_{35}$F$_3$N$_5$O$_6$ (MH$^+$) 510.2539, found: 510.2526.

Example 27

N4,N4-dimethyl-N1-(3,3,3-trifluoro-1-methyl-2-oxopropyl)-(2S)-2-[((1S)-2,2-dimethyl-1-[(1S)-2-methyl-1-(methylcarboxamido)propyl]carboxamidopropyl)carboxamido]-butanediamide (58, Table 3)

This compound was prepared on solid phase using the activated ketone resin (Example 1). Final purification was performed by preparative HPLC. HPLC (system A) 100%, (system B) 99%; IR (KBr) υ 3500–2900, 1640, 1538 cm$^{-1}$; $^1$H-NMR (400 MHz, DMSO-d$_6$), hydrated form only, 1:1 mixture of diastereomers at P$_1$, δ 8.20 and 8.13 (d, J=7.4 and 7.2 Hz, 1H), 7.91 and 7.91 (d, J=9.0 and 8.7 Hz, 1H), 7.56 and 7.55 (d, J=9.3 and 9.3 Hz, 1H), 7.50 and 7.43 (d, J=9.3 and 9.3 Hz, 1H), 6.93 (br s, 1H), 6.81 (br s, 1H), 4.57 (m, 1H), 4.23 (m, 2H), 4.11 (m, 1H), 2.95 and 2.94 (s, 3H), 2.80 and 2.80 (s, 3H), 2.72–2.57 (m, 2 H), 1.95 (m, J=6.9 Hz, 1H), 1.87 (s, 3H), 1.07 and 1.06 (d, J=8.1 and 6.6 Hz, 3H), 0.89 (s, 9H), 0.83 (d, J=6.8 Hz, 6H); FAB MS m/z: 538 (MH$^+$); HRMS calcd for C$_{23}$H$_{39}$F$_3$N$_5$O$_6$ (MH$^+$) 538.2852, found: 538.2843.

Example 28

N4,N4-dimethyl-N1-(3,3,3-trifluoro-1-methyl-2-oxopropyl)-(2S)-2-[((1S)-3,3-dimethyl-1-[(1S)-2-methyl-1-(methylcarboxamido)propyl]carboxamido butyl)carboxamido]butanediamide (59, Table 3)

This compound was prepared on solid phase using the activated ketone resin (Example 1). Final purification was performed by preparative HPLC. HPLC (system A) 100%, (system D, pH 7.4) 100%; IR (KBr) υ 3285, 1644 cm$^{-1}$; $^1$H NMR (400 MHz, DMSO-d$_6$), 16:1 mixture of hydrate/non-hydrate, 3:2 mixture of diastereomers at P$_1$, δ 8.05 (d, J=8.3 Hz, 1H), 7.91–7.79 (m, 2H), 7.43 and 7.39 (2×d, J=9.2 and 9.2, 1H), 7.11–6.66 (br s, 2H hydrate), 4.62–4.49 (m, 1H), 4.36–4.25 (m, 1H), 4.16–4.02 (m, 2H), 2.94 and 2.93 (2×s, 3H), 2.80 (s, 3H), 2.71–2.55 (m, 2H), 1.99–1.88 (m, 1H), 1.85 and 1.84 (2×s, 3H), 1.67–1.58 (m, 1H), 1.46 (dd, J=14.2 and 8.9 Hz, 1H), 1.28–1.25 (m, 0.2H), 1.06 (d, J=6.7 Hz, 2.8H), 0.86 (s, 9H), 0.83 (d, J=6.7 Hz, 3H), 0.81 (d, J=6.7 Hz, 3H); FAB MS m/z: 552 (MH$^+$), 570 (M+19); HRMS calcd for C$_{24}$H$_{41}$F$_3$N$_5$O$_6$ (MH$^+$) 552.3009, found: 552.3031.

Example 29

N4,N4-dimethyl-N1-(3,3,3-trifluoro-1-methyl-2-oxopropyl)-(2S)-2-[((S)-1-(1-adamantyl)-1-[(1 S)-2-methyl-1-(methylcarboxamido)propyl]carboxamido methyl)carboxamido]butane-diamide (60, Table 3)

This compound was prepared in solution using standard coupling methods and oxidized with Dess-Martin periodinane. Final purification was performed by preparative HPLC. HPLC (system A) 100%, (system D) 99%; IR (KBr) υ 3293, 1641, 1533 cm$^{-1}$; $^1$H-NMR (400 MHz, DMSO-d$_6$), 4:1 mixture of hydrate/non-hydrate, 1:1 mixture of diastereomers at P$_1$, δ 8.58 (d, J=5.5 Hz, 0.1H), 8.47 (d, J=6.5 Hz, 0.1H), 8.22–8.12 (m, 1H), 7.94–7.91 (m, 1H), 7.49–7.38 (m, 1.9H), 6.94 (br s, 1H), 6.86 (br s, 1H), 4.60–4.52 (m, 1H), 4.24–4.20 (m, 1H), 4.13–3.98 (m, 2H), 2.94 (s, 1.5H), 2.93 (s, 1.5H), 2.79 (s, 3H), 2.74–2.57 (m, 2H), 2.00–1.94 (m, 1H), 1.94–1.86 (m, 3H), 1.87 (s, 3H), 1.64–1.48 (m, 12H), 1.26–1.25 (m, 0.6H), 1.07 (d, J=6.5 Hz, 2.4H), 0.82 (d, J=6.5 Hz, 6H); FAB MS m/z: 616 (MH$^+$); HRMS calcd for C$_{29}$H$_{45}$F$_3$N$_5$O$_6$ (MH$^+$) 616.3322, found: 616.3335; Anal (C$_{29}$H$_{44}$F$_3$N$_5$O$_6$H$_2$O) C, H, N.

Example 30

(3S)-3-((1S)-2-(dimethylcarbamoyl)-1-[(3,3,3-trifluoro-1-methyl-2-oxopropyl)carbamoyl]-ethylcarbamoyl)-2,2-dimethyl-3-[(1S)-2-methyl-1-(methylcarboxamido)propyl]carboxamidopropanoic acid (61, Table 3)

This compound was prepared in solution using standard coupling methods. The β,β-dimethyl aspartic acid residue was incorporated as the γ-benzyl ester derivative. Oxidation of the trifluoromethyl alcohol was accomplished with the Dess-Martin periodinane. Final purification was performed by preparative HPLC. HPLC (system A) 96%, (system D) 98%, IR (KBr) υ 1654, 1532 cm$^{-1}$; $^1$H-NMR (400 MHz, DMSO-d$_6$) 1:1 mixture of diastereomers at P$_1$, δ 7.98–7.89 (m, 2 H), 7.76 (d, J=7.5 Hz, 0.5H), 7.67 (d, J=7.5 Hz, 0.5H), 7.53 (d, J=9 Hz, 0.5H), 7.48 (d, J=9 Hz, 0.5H), 6.92 (br s, 1H), 6.83 (br s, 1H), 4.75 (d, J=9.5 Hz, 1H), 4.57–4.51 (m, 1H), 4.27–4.19 (m, 1H), 4.18–4.03 (m, 1H), 2.94 (s, 1.5H), 2.93 (s, 1.5H), 2.80 (s, 3H), 2.71–2.57 (m, 2H), 2.04–1.95 (m, 1H), 1.87 (s, 3H), 1.08–1.05 (m, 9H), 0.85 (d, J=6.5 Hz, 3H), 0.83 (d, J=6.5 Hz, 3H); FAB MS m/z: 568 (MH$^+$); HRMS calcd for C$_{23}$H$_{37}$F$_3$N$_5$O$_8$ (MH$^+$) 568.2594; found: 568.2505.

Example 31

N4,N4-dimethyl-N1-(3,3,3-trifluoro-1-methyl-2-oxopropyl)-(2S)-2-[(1S)-2,2-dimethyl-1-(methylcarboxamido)propyl] carboxamidobutanediamide (62, Table 4)

This compound was prepared in solution using standard coupling methods and the trifluoromethyl alcohol oxidized with the Dess-Martin periodinane. Final purification was performed by preparative HPLC. HPLC (system A) 99%, (system E) 100%; IR (KBr) υ 1640 cm$^{-1}$; $^1$H-NMR (400 MHz, DMSO-d$_6$), 1:1 mixture of diastereomers at P$_1$, δ 8.06 and 7.94 (2×d, J=7.6 and 7.3 Hz, 1H), 7.69 (d, J=8.9 Hz, 1H), 7.22 and 7.21 (2×d, J=8.9 and 9.2 Hz, 1H), 4.42–4.34 (m, 1H), 4.01 and 3.96 (2×d, J=8.9 and 8.9 Hz, 1H), 3.95–3.89 (m, 1H), 2.77 (d, J=3.2 Hz, 3H), 2.62 (s, 3H), 2.59–2.42 (m, 2H), 1.72 (d, J=3.8 Hz, 3H), 1.09 and 0.89 (2×d, J=7.0 and 6.7 Hz, 3H), 0.73 and 0.72 (2×s, 9H); FAB MS m/z: 439 (MH$^+$), 457 (M+19); HRMS calcd for C$_{18}$H$_{30}$F$_3$N$_4$O$_5$ (MH$^+$) 439.2168, found: 439.2154.

Example 32

N4,N4-dimethyl-N1-(3,3,3-trifluoro-1-methyl-2-oxopropyl)-(2S)-2-((1S)-1-[( 4-hydroxyphenethyl) carboxamido]-2,2-dimethylpropylcarboxamido) butanediamide (63, Table 4)

This compound was prepared on solid phase using the activated ketone resin (Example 1). Final purification was performed on a preparative HPLC. HPLC (system A) 97%, (system B) 95%; IR (KBr) υ 1636 cm$^{-1}$; $^1$H-NMR (400 MHz, DMSO-d$_6$) 16:1 mixture of hydrate/non-hydrate, 1.4:1 mixture of diastereomers at P$_1$, δ 9.20–9.00 (m, 1H), 8.23 and 8.13 (2×d, J=7.4 and 7.4 Hz, 1H), 7.79 (2×d, J=9.0 and 9.0 Hz, 1H), 7.41 (2×d, J=9.0 and 9.0 Hz, 1H), 6.99 (d, J=8.6 Hz, 2H), 6.99–6.75 (m, 1.5H hydrate), 6.65–6.62 (m, 2H), 4.62–4.52 (m, 1H), 4.20 and 4.17 (2×d, J=9.0 and 9.0 Hz, 1H), 4.15–4.05 (m, 1H), 2.96 and 2.95 (2×s, 3H), 2.80 (s, 3H), 2.72–2.60 (m, 4H), 2.50–2.45 (m, 1H), 2.45–2.35 (m, 1H), 1.27 (d, J=7.0 Hz, 0.1H), 1.75 (m, 2.8H), 0.86 (s, 9H); FAB MS m/z: 545 (MH$^+$), 563 (M+19); HRMS calcd for C$_{25}$H$_{36}$F$_3$N$_4$O$_6$ (MH$^+$) 545.2587, found 545.2602.

Example 33

N4,N4-dimethyl-N1-(3,3,3-trifluoro-1-methyl-2-oxopropyl)-(2S)-2-[(1S)-1-(isobutylcarboxamido)-2,2-dimethylpropyl]carboxamidobutanediamide (64, Table 4)

This compound was prepared in solution using standard coupling methods. Final purification was performed by preparative HPLC. HPLC (system A) 95%, (system B) 99%; IR (KBr) υ 1636 cm$^{-1}$; $^1$H-NMR (400 MHz, DMSO-d$_6$), 19:1 mixture hydrate/non-hydrate, 1:1 mixture of diastereomers at P$_1$, δ 8.21 and 8.11 (2×d, J=7.2 and 7.2 Hz, 1H), 7.73 and 7.72 (2×d, J=9.0 and 9.0 Hz, 1H), 7.44 and 7.40 (2×d, J=9.6 and 9.3 Hz, 1H), 7.1–6.7 (br, 1.7H hydrate), 4.60–4.52 (m, 1H), 4.21 and 4.19 (2×d, J=9.0 and 8.7 Hz, 1H), 4.15–4.04 (m, 1H), 2.96 and 2.95 (2×s, 3H), 2.80 (s, 3H), 2.74–2.58 (m, 2H), 2.14 and 2.12 (2×d, J=13.2 and 12.9 Hz, 1H), 2.08 (m, 1H), 1.96 (m, 1H), 1.07–1.04 (m, 3H) 0.90 (s, 9H), 0.87 (d, J=6.6 Hz, 3H), 0.86 (d, J=6.6 Hz, 3H); FAB MS m/z: 481 (MH$^+$), 499 (M+19); HRMS calcd for C$_{21}$H$_{36}$F$_3$N$_4$O$_5$ (MH$^+$) 481.2638, found 481.2627.

Example 34

N4,N4-dimethyl-N1-(3,3,3-trifluoro-1-methyl-2-oxopropyl)-(2S)-2-[(1S)-2,2-dimethyl-1-(neopentylcarboxamido)propyl] carboxamidobutanediamide (65, Table 4)

This compound was prepared on solid phase using the activated ketone resin (Example 1). Final purification was performed by preparative HPLC. HPLC (system A) 99%, (system B) 99%; IR (KBr) υ 1635 cm$^{-1}$; $^1$H-NMR (400 MHz, DMSO-d$_6$), 29:1 mixture of hydrate/non-hydrate, 1:1 mixture of diastereomers at P$_1$, δ 8.20 and 8.10 (2×d, J=7.3 and 7.0 Hz, 1H), 7.62 (d, J=8.9 Hz, 1H), 7.44 and 7.43 (2×d, J=9.2 and 9.2 Hz, 1H), 6.95–6.75 (m, 1.7H), 4.56 (quintet, J=6.7 Hz, 1H), 4.19 and 4.16 (2×d, J=8.9 and 8.9 Hz, 1H), 4.12–4.05 (m, 1H), 2.95 and 2.94 (2×s, 3H), 2.79 (s, 3H), 2.75–2.60 (m, 2H), 2.20–2.15 (m, 1H), 2.04 and 2.01 (2×d, J=12.7 and 12.4 Hz, 1H), 1.07–1.04 (m, 3H), 0.95 (s, 9H), 0.90 (s, 9H); FAB MS m/z: 495 (MH$^+$), 513 (M+19); HRMS calcd for C$_{22}$H$_{38}$F$_3$N$_4$O$_5$ (MH$^+$) 495.2794, found 495.2777.

Example 35

N4,N4-dimethyl-N1-(3,3,3-trifluoro-1-methyl-2-oxopropyl)-(2S)-2-((1S)-1-[(3,3-dimethyl-butyl) amino]-2,2-dimethylpropylcarboxamido) butanediamide (66, Table 4)

This compound was prepared by solid phase using the activated ketone resin (Example 1). The final reductive amination on the terminal t-butyl glycine amine (0.3 mmol) was performed on solid phase by addition of 3,3-dimethylbutyraldehyde (376 mL, 3.0 mmol) in DMF (15 mL with acetic acid (150 mL), and NaBH$_3$CN (63 mg, 1 mmol) for 20 h. After removal of the solvent, the resin was cleaved in the usual fashion. After purification by preparative HPLC the compound was obtained as a white solid (20.6 mg) after lyophilization. HPLC (system A) 99%, (system D) 97%; IR (KBr) υ 2960, 1667 cm$^{-1}$; $^1$H-NMR (400 MHz, DMSO-d$_6$), 1:1 mixture of diastereomers at P$_1$, δ 8.79–8.72 (m, 2H), 8.04 (br s, 1H), 7.78 (d, J=9.0 Hz, 0.5H), 7.67 (d, J=9.0 Hz, 0.5H), 6.97–6.96 (m, 1.3H), 6.91 (s, 0.6H), 4.82–4.75 (m, 1H), 4.15–4.11 (m, 1H), 3.61 (d, J=9.5 Hz, 1H), 2.94 (m, 3H), 2.87 (m, 1H), 2.79 (m, 3H), 2.70–2.65 (m, 3H), 1.66–1.57 (m, 1H), 1.51–1.44 (m, 1H), 1.29–1.24 (m, 1H), 1.08 (d, J=7.0 Hz, 3H), 1.02 (s, 5.4H), 0.99 (s, 3.6H), 0.89 (s, 3.6H), 0.89 (s, 5.4H); FAB MS m/z: 481 (MH$^+$), 499 (M+19); HRMS calcd for C$_{22}$H$_{40}$F$_3$N$_4$O$_4$ (MH$^+$) 481.3002, found: 481.2991.

Example 36

4N,4N-Dimethyl-1N-(3,3,3-trifluoro-1-methyl-2-oxopropyl-2-[1-(tert-butoxycarbonyl-amino)-2,2-dimethyl-(1S)-propylcarboxamido]-(2S)-butanediamide (67, Table 4)

This compound was prepared on solid phase using the activated ketone resin (Example 1). The final purification was performed by preparative HPLC. HPLC (system A) 99%, (system B) 98%; IR (KBr) υ 3500–2900, 1641, 1510 cm$^{-1}$; $^1$H-NMR (400 MHz, DMSO-d$_6$), 5:1 mixture of hydrate/non-hydrate, 1:1 mixture of diastereomers at P$_1$, δ 8.56 (br d, J=5.1 Hz, 0.15H), 8.10–8.00 (m, 1H), 7.50–7.46 (m, 1H), 6.93–6.82 (m, 1.7H), 6.50–6.49 (m, 1H), 4.62 (m, 1H), 4.12 (m, 1H), 3.84 (m, 1H), 2.95 (m, 3H), 2.80 (s, 3H), 2.65 (m, 2H), 1.38 (s, 9H), 1.26 (d, J=6.6 Hz, 0.45H), 1.06 (d, J=6.6 Hz, 2.55H), 0.88 (s, 9H); FAB MS m/z: 497 (MH$^+$); HRMS calcd for C$_{21}$H$_{36}$F$_3$N$_4$O$_6$ (MH$^+$) 497.2587, found: 497.2601.

Example 37

N4,N4-Dimethyl-N1-(3,3,3-trifluoro-1-methyl-2-oxopropyl-2-[1-(tert-butylaminocarbonyl-amino)-2,2-dimethyl-(1S)-propylcarboxamido]-(2S)-butanediamide (68, Table 4)

This compound was prepared in solution using standard coupling methods and oxidation of the trifluoromethyl alcohol with the Dess-Martin periodinane. Final purification was performed by preparative HPLC. HPLC (system A) 99%, (system D) 100%; IR (KBr) υ 1641 cm$^{-1}$; $^1$H-NMR (400 MHz, DMSO-d$_6$), 1:1 mixture of diastereomers at P$_1$, δ 8.15 and 8.09 (2×d, J=7.3 and 7.0 Hz, 1H), 7.51 and 7.43 (2×d, J=8.9 and 9.2 Hz, 1H), 6.00 (s, 1H), 5.97–5.93 (m, 1H), 4.58–4.53 (m, 1H), 4.11–4.03 (m, 1H), 3.94–3.91 (m, 1H), 2.95 (d, J=5 Hz, 3H), 2.79 (s, 3H), 2.67–2.60 (m, 2H), 1.20 (s, 9H), 1.07–1.05 (m, 3H), 0.86 (s, 9H); FAB MS m/z: 496 (MH$^+$), 514 (M+19); HRMS calcd for C$_{21}$H$_{37}$F$_3$N$_5$O$_5$ (MH$^+$) 496.2747, found: 496.2765.

Example 38

N4,N4-dimethyl-N1-(3,3,3-trifluoro-1-methyl-2-oxopropyl)-(2S)-2-[((1S)-1-[(dimethylamino)methyl]carboxamido-2,2-dimethylpropyl)carboxamido]butanediamide (69, Table 4)

This compound was prepared in solution using standard coupling methods and oxidation of the trifluoromethyl alcohol with the Dess-Martin periodinane. Final purification was performed by preparative HPLC. HPLC (system A) 100%, (system D) 98%; IR (KBr) υ 1654, 1540, 1186 cm$^{-1}$; $^1$H-NMR (400 MHz, DMSO-d$_6$), 9:1 mixture of hydrate/non-hydrate, 1:1 mixture of diastereomers at P$_1$, δ 9.61 (br s, 1H), 8.68 and 8.66 (2×d, J=9.0 and 8.5 Hz, 1 H), 8.37 and 8.30 (2×d, J=7.5 and 7.0 Hz, 1H), 7.48 and 7.45 (2×d, J=9.0 and 9.0 Hz, 1H), 6.95–6.87 (m, 2H), 4.63–4.54 (m, 1H), 4.35–4.32 (m, 1H), 4.12–3.94 (m, 3H), 2.95–2.94 (m, 3H), 2.95–2.94 (m, 3H), 2.80–2.78 (m, 9H), 2.72–2.56 (m, 2H), 1.26–1.24 (m, 0.3H), 1.07–1.06 (m, 2.7H), 0.92 (s, 9H); FAB MS m/z: 482 (MH$^+$), 500.1 (M+19); HRMS calcd for C$_{20}$H$_{35}$F$_3$N$_5$O$_5$ (MH$^+$) 482.2590, found: 482.2599.

Example 39

4-[(1S)-1-((1S)-2-(dimethylcarbamoyl)-1-[(3,3,3-trifluoro-1-methyl-2-oxopropyl)carbamoyl]ethylcarbamoyl)-2,2-dimethylpropyl]carbamoylbutanoic acid (70, Table 4)

This compound was prepared in solution using standard coupling methods. The final P$_4$ residue was introduced by the opening of glutaric anhydride in Et$_3$N. Final purification was performed by preparative HPLC. HPLC (system A) 100%, (system D) 100%; IR (KBr) υ 1638, 1537, 1176 cm$^{-1}$; $^1$H-NMR (400 MHz, DMSO-d$_6$) 1:1 mixture of diastereomers at P$_1$, δ 8.22 and 8.12 (2×d, J=7.5 and 7.0 Hz, 1H), 7.81–7.72 (m, 1H), 7.43 and 7.39 (2×d, J=9.0 and 9.0 Hz, 1H), 6.93 (br s, 0.8H), 6.81 (br s, 0.8H), 4.60–4.52 (m, 1H), 4.21–4.18 (m, 1H), 4.12–4.05 (m, 1H), 2.95–2.94 (m, 3H), 2.79 (s, 3H), 2.68–2.63 (m, 2H), 2.28–2.14 (m, 4H), 1.73–1.66 (m, 2H), 1.11–1.05 (m, 3H), 0.89 (s, 9H); FAB MS m/z: 511.2 (MH$^+$), 529 (M+19); HRMS calcd for C$_{21}$H$_{34}$F$_3$N$_4$O$_7$ (MH$^+$) 511.2379, found: 511.2363; Anal (C$_{21}$H$_{33}$F$_3$N$_4$O$_7$·2H$_2$O) C, H, N.

Example 40

N4,N4-dimethyl-N1-(3,3,3-trifluoro-1-methyl-2-oxopropyl)-(2S)-2-[(1S)-1-amino-2,2-dimethylpropyl] carboxamidobutanediamide This compound was prepared on solid phase using the activated ketone resin (Example 1). Final purification was performed by preparative HPLC. HPLC (system D) 99%, (system E) 99%; IR (KBr) υ 1670 cm$^{-1}$; $^1$H-NMR (400 MHz, DMSO-d$_6$), 2:1 hydrate/non-hydrate, 1:1 mixture of diastereomers at P$_1$, δ 8.87 and 8.80 (2×d, J=5.7 and 6.4 Hz, 0.4H), 8.56–8.49 (m, 1H), 8.02 (br s, 3H), 7.69 and 7.64 (2×d, J=9.0 and 9.2 Hz, 0.6H), 6.96, 6.95, 6.88 and 6.83 (4 ×s, 1.3H), 4.73–4.63 (m, 1.4H), 4.14–4.08 (m, 0.6H), 3.55–3.48 (m, 1H), 2.96 (s, 3H), 2.82 (s, 3H), 2.74–2.58 (m, 2H), 1.25 (d, J=6.7 Hz, 1H), 1.08 and 1.07 (2×d, J=6.7 and 6.7 Hz, 2H), 1.01–0.96 (m, 9H); FAB MS m/z: 397 (MH$^+$), 415 (M+19); HRMS calcd for C$_{16}$H$_{28}$F$_3$N$_4$O$_4$ (MH$^+$) 397.2063, found: 397.2077.

Example 41

N4,N4-dimethyl-N1-(3,3,3-trifluoro-1-methyl-2-oxopropyl)-(2S)-2-[(1S)-1-hydroxy-2,2-dimethylpropyl] carboxamidobutanediamide This compound was prepared in solution using standard coupling methods. The 2-hydroxy isobutyric acid moiety was introduced as the acetyl derivative. Oxidation of the trifluoromethyl alcohol with the Dess-Martin periodinane was followed by cleavage of the acetate group with aq. NaOH. Final purification was performed by preparative HPLC. HPLC (system A) 92%, (system D) 99%; IR (KBr) υ 1641 cm$^{-1}$; $^1$H-NMR (400 MHz, DMSO-d$_6$), 2:1 hydrate, non-hydrate, 1:1 mixture of diastereomers at P$_1$, δ 7.83 and 7.79 (2×d, J=7.9 and 7.6 Hz, 1H), 7.73–7.67 (m, 0.3H), 7.57 and 7.52 (2×d, J=9.2 and 9.2 Hz, 1H), 7.04–6.82 (m, 2H, hydrate), 5.69–5.47 (m, 1H), 4.65–4.55 (m, 1H), 4.19–4.05 (m, 1H), 2.95 and 2.94 (2×s, 3H) 2.80 and 2.79 (2×s, 3H), 2.79–2.53 (m, 3H), 1.39–1.02 (m, 3H), 0.87 (s, 9H); FAB MS m/z: 398 (MH$^+$), 416 (M+19); HRMS calcd. for C$_{16}$H$_{27}$F$_3$N$_3$O$_5$ (MH$^+$) 398.1903, found: 398.1892.

Example 42

N4,N4-dimethyl-N1-(3,3,3-trifluoro-1-methyl-2-oxopropyl)-(2S)-2-(neopentylcarboxamido)-butanediamide This compound was prepared in solution using standard coupling methods and final oxidation of the trifluoromethyl alcohol was accomplished with the Dess-Martin periodinane. Final purification was performed by preparative HPLC. HPLC (system D) 97%, (system E) 99%; IR (KBr) υ 1638 cm$^{-1}$; $^1$H-NMR (400 MHz, DMSO-d$_6$), 2:1 mixture of diastereomers at P$_1$, δ 7.80–7.77 (m, 1H), 7.27 and 7.22 (2×d, J=9.2 and 9.2 Hz, 1H), 4.49–4.42 (m, 1H), 3.98–3.92 (m, 1H), 2.80 (s, 3H), 2.64 (s, 3H), 2.55–2.40 (m, 2H), 1.84

(s, 2H), 1.10 and 0.92 (2×d, J=6.9 and 6.6 Hz, 3H), 0.79 (s, 9H); FAB MS m/z: 382 (MH$^+$), 400 (M+19); HRMS calcd for $C_{16}H_{27}F_3N_3O_4$ (MH$^+$) 382.1954, found: 382.1968.

Example 43

N4,N4-dimethyl-N1-(3,3,4,4,4-pentafluoro-1-methyl-2-oxobutyl)-(2S)-2-[(1S)-2,2-dimethyl-1-(neopentyl carboxamido)propyl] carboxamidobutanediamide (74, Table 5)

Compound 11 (0.92 g, 3.14 mmol) was treated with 4 N HCl/dioxane (1.5 h) before being concentrated in vacuo. The resulting hydrochloride salt (3.14 mmol) was combined with Boc-Asn(γ-NMe$_2$)—OH (0.93 g, 3.45 mmol), TBTU (1.21 g, 3.77 mmol), HOBt (0.51 g, 1.2 mmol), and i-Pr$_2$NEt (1.64 mL, 9.42 mmol) in CH$_2$Cl$_2$ (10 mL). After 3 h at rt, the mixture was extracted into EtOAc and washed with 1 N HCl, saturated aqueous NaHCO$_3$, and brine. The organic phase was dried (MgSO$_4$), filtered and concentrated in vacuo. The residue was purified by flash chromatography (4:1 EtOAc/hexane) to give the coupled product (0.594 g, 43%). HPLC (system A) 93%; $^1$H-NMR (CDCl$_3$), 1.3:1 mixture of diastereomers, δ 6.92 (bs, 0.6H), 6.66 (d, J=7.95 Hz, 0.4H), 5.80 (m, 1H), 4.71 (bs, 0.4H), 4.50 (m, 1.6H), 4.45–4.20 (m, 2H), 3.34 (dd, J=16.85 and 16.85 Hz, 0.4H), 3.06–2.97(m, 0.6H), 3.045 and 3.04 (2×s, 3H), 3.02 and 3.00 (2×s, 3H), 2.67 (dd, J=7.63 and 7.63 Hz, 0.6H), 2.58 (dd, J=16.85 and 16.85 Hz, 0.4H), 1.48 and 1.46 (2×s, 9H), 1.32 (t, J=7.95 Hz, 3H). The dipeptide (0.43 g, 0.99 mmol) was treated with 4 N HCl/dioxane (10 mL) for 2 h before being concentrated in vacuo. The resulting hydrochloride salt (0.99 mmol) was combined with Boc-Tbg-OH (0.254 g, 1.1 mmol), BOP (0.487 g, 1.1 mmol), and i-Pr$_2$NEt (0.52 mL, 3.0 mmol) in CH$_2$Cl$_2$ (10 mL). After 2.5 h at rt, the mixture was extracted into EtOAc and washed with 1 N HCl, saturated aqueous NaHCO$_3$, and brine. The organic phase was dried (MgSO$_4$), filtered and concentrated in vacuo. The residue was purified by flash chromatography (1:1 EtOAc/hexane) to give the coupled product as a white solid (0.33 g, 60%). HPLC (system A) 99%; $^1$H-NMR (CDCl$_3$), 1.3:1 mixture of diastereomers, δ 8.15 (m, 0.4H), 7.73 (m, 0.6H), 7.37 (m, 0.6H), 7.10 (m, 0.4H), 5.12 (m, 1H), 4.77 (m, 0.7H), 4.69 (m, 1.3H), 4.25 (m, 2H), 3.76 (m, 1H), 3.26 (dd, J=15.9 and 15.9 Hz, 0.4H), 3.16 (dd, J=12.4 and 12.4 Hz, 0.6H), 3.06 and 3.03 (2×s, 3H), 2.94 and 2.92 (2×s, 3H), 2.55 (dd, J=7.0 and 7.0 Hz, 0.6H), 2.39 (dd, J=11.4 and 11.4 Hz, 0.4H), 1.46 and 1.45 (2×s, 9H), 1.37–1.25 (m, 3H), 1.06 and 1.03 (2×s, 9H). This peptide (0.30 g, 0.67 mmol) was then treated with 4 N HCl/dioxane (10 mL) and concentrated in vacuo. The hydrochloride salt was combined with tert-butylacetic acid (0.094 μL, 0.74 mmol), BOP (0.33 g, 0.74 mmol), i-Pr$_2$NEt (0.23 mL, 1.34 mmol) in CH$_2$Cl$_2$ (10 mL) and stirred 3.5 h at rt. The mixture was diluted with EtOAc and washed with 1 N HCl, saturated aqueous NaHCO$_3$, and brine. The organic phase was dried (MgSO$_4$), filtered and concentrated in vacuo. The residue was purified by flash chromatography to give the desired peptide as a white solid (0.297 g, 88%). HPLC (system A) 99%); $^1$H-NMR (CDCl$_3$) δ 7.79 (d, J=7.6 Hz, 1H), 7.32 (d, 8.3 Hz, 1H), 6.18 (d, J=6.7 Hz, 1H), 5.21 (d, J=6.7 Hz, 1H), 4.82–4.78 (m, 1H), 4.39–4.31 (m, 1H), 4.23–4.10 (m, 2H), 3.11–3.06 (dd, J=16.2 and 15.7 Hz, 1H), 2.99 (s, 3H), 2.91 (s, 3H), 2.52 (dd, J=16.2 and 15.9 Hz, 1H), 2.18 (s, 2H), 1.27 (d, J=6.7 Hz, 3H), 1.06 (s, 9H), 1.05 (s, 9H). The alcohol (0.26 g, 0.48 mmol) so obtained was combined with Dess-Martin periodinane (0.51 g, 1.19 mmol) in CH$_2$Cl$_2$ (5 mL) and stirred for 4 h. The reaction mixture was diluted with EtOAc and treated with a 1:1 mixture of 10% Na$_2$S$_2$O$_3$: saturated NaHCO$_3$ (10 mL) for 15 min. After extraction with EtOAc the organic phase was dried (MgSO$_4$), filtered and concentrated in vacuo. The pentafluoroethyl ketone was obtained by trituration with 3:1 hexane/EtOAc to give 74 as a white solid (0.217 g, 84%). IR (KBr) υ 1685, 1618 cm$^{-1}$; $^1$H-NMR (DMSO-d$_6$) 3:1 mixture of diastereomers at P$_1$, δ 8.20 and 8.14 (2×d, J=7.5 and 7.5 Hz, 1H), 7.66 (d, J=9.0 Hz, 1H), 7.51 (d, J=8.8 Hz, 1H), 6.91 (m, 2H), 4.58 (m, 1H), 4.16 (m, 2H), 2.95 and 2.80 (2×s, 6H), 2.70 (m, 2H), 2.11 (m, 2H), 1.08 (d, J=6.6 Hz, 3H), 0.95 (s, 9H), 0.91 (s, 9H); HRMS calcd for $C_{23}H_{38}F_5N_4O_5$ (MH$^+$) 545.2762, found: 545.2775.

Example 44

N1-[3-(benzylcarbamoyl)-3,3-difluoro-1-methyl-2-oxopropyl]-N4,N4-dimethyl-(2S)-2-[(1S)-2,2-dimethyl-1-(neopentylcarboxamido)propyl] carboxamidobutane diamide (75, Table 5)

Compound 13 (0.263 g, 0.73 mmol) was treated with 4N HCl/dioxane (6 mL) for 30 min before being concentrated in vacuo. The resulting hydrochloride salt was combined with BOP (0.39 g, 0.88 mmol), Boc-Asn(γ-NMe$_2$)—OH (0.191 g, 0.73 mmol) and i-Pr$_2$NEt (0.32 mL, 1.83 mmol) in CH$_2$Cl$_2$ (5 mL). After 4 h, the reaction was poured into EtOAc and washed sequentially with 1N HCl, saturated aqueous NaHCO$_3$, and brine. The organic phase was dried (MgSO$_4$), filtered and concentrated in vacuo. The material was triturated with 3:7 hexane:EtOAc to give a white solid (0.30 g, 82%). $^1$H-NMR (CDCl$_3$) δ 7.41–7.28 (m, 6H), 6.98–6.94 (m br, 1H), 5.56–5.51 (m br, 1H), 4.59–4.42 (m, 4H), 4.11–4.03 (m, 2H), 3.11–3.05 (m, 1H), 2.99 (s, 3H), 2.88 (s, 3H), 2.61–2.54 (m, 1H), 1.45 (s, 9H), 1.32 (d, J=6.6 Hz, 3H). This material (0.27 g, 0.54 mmol) was treated with 4 N HCl/dioxane (6 mL) for 30 min before being concentrated in vacuo. The hydrochloride salt (0.54 mmol) was combined with Boc-Tbg-OH (0.125 g, 0.54 mmol), BOP (0.286 g, 0.65 mmol) and i-Pr$_2$NEt (0.23 mL, 1.35 mmol) in CH$_2$Cl$_2$ (3 mL) and stirred for 4 h. The mixture was diluted with EtOAc and washed sequentially with 1 N HCl, saturated aqueous NaHCO$_3$, and brine before being dried (MgSO$_4$), filtered and concentrated in vacuo. The product was purified by flash chromatography using TLC grade silica gel to afford a white solid (0.25 g, 76%). $^1$H-NMR (CDC$_{13}$) δ 8.06 (s br, 1H), 7.68 (s br, 1H), 7.33–7.26 (m, 6H), 5.11 (d, J=4.4 Hz, 1H), 4.67 (dd, J=14.6, 7.0 Hz, 1H), 4.50 (s br, 1H), 4.32–4.22 (m, 3H), 4.13–4.07 (m, 1H), 3.71 (d, J=5.7 Hz, 1H), 3.23–3.20 (m, 1H), 3.00 (s, 3H), 2.87 (s, 3H), 2.43–2.38 (dd, J=15.9, 5.7 Hz, 1H), 1.49 (s, 9H), 1.22 (d, J=6.7 Hz, 3H), 1.02 (s, 9H). This peptide (0.25 g, 0.41 mmol) was treated with 4 N HCl/dioxane (3 mL) and stirred 1 h before being concentrated in vacuo. The hydrochloride salt (0.41 mmol) was combined with tert-butylacetic acid (52 μL, 0.41 mmol), BOP (0.216 g, 0.49 mmol) and i-Pr$_2$NEt (0.18 mL, 1.02 mmol) in CH$_2$Cl$_2$ (3 mL) and stirred 4 h. The mixture was diluted with EtOAc and washed sequentially with 1 N HCl, saturated aqueous NaHCO$_3$, and brine before being dried (MgSO$_4$), filtered and concentrated in vacuo. The product was purified by flash chromatography using TLC grade silica gel (5% MeOH/EtOAc) to give the fully elaborated peptide as a white solid (0.191 g, 77%). $^1$H-NMR (CDCl$_3$) δ 7.65 (d, J=7.6 Hz, 1H), 7.37–7.27 (m, 7H), 5.97 (d, J=6.7 Hz, 1H), 4.65–4.59 (m, 2H), 4.46 (d, J=9.2 Hz, 1H), 4.35 (dd, J=15.0, 5.4 Hz, 1H), 4.28–4.24 (m, 1H), 4.15–4.06 (m, 1H), 4.02 (d, J=6.7 Hz, 1H), 3.16 (dd, J=15.9, 3.5 Hz, 1H), 2.99 (s, 3H), 2.87 (s, 3H), 2.45 (dd, J=15.6, 9.2 Hz, 1H), 2.19 (dd, J=18.1, 13.0 Hz, 2H), 1.24 (d, J=7.0 Hz, 3H), 1.05 (s, 9H), 1.03 (s, 9H). The peptide (0.15 g, 0.245 mmol) was dissolved in $CH_2Cl_2$ (15 mL) and treated with Dess-Martin periodinane (0.10 g, 0.245 mmol) and stirred at rt for 5 h. The mixture was diluted with EtOAc and treated with a 1:1 mixture of 10% $Na_2S_2O_3$: saturated $NaHCO_3$ (15 min). The organic phase was washed sequentially with saturated $NaHCO_3$, 10% citric acid, and brine before being dried ($MgSO_4$), filtered, and concentrated in vacuo. The final product was purified by preparative HPLC to give, after lyophilization, compound 75 as a white solid (0.115 g, 77%). IR (KBr) υ 3293, 1680, 1635 cm$^{-1}$, $^1$H-NMR (CDCl$_3$), 1:3 mixture of hydrate/non-hydrate, δ 9.65–9.55 (m, 0.25H), 8.99–8.47 (m, 0.75H), 8.20–8.15 (m, 1H), 7.65–7.55 (m, 1H), 7.40–7.20 (m, 6H), 6.55 (br s, 0.25H), 6.34 (br s, 0.75H), 4.80–4.72 (m, 0.25H), 4.59–4.53 (m, 1H), 4.42–4.26 (m, 2H), 4.26–4.16 (m, 1.5H), 4.11 (d, J=8.3 Hz, 0.25), 2.96 (s, 2.25H), 2.93 (s, 0.75H), 2.79 (s, 0.75H), 2.77 (s, 2.25H), 2.68 (m, 2H), 2.25–2.18 (m, 1H), 2.05–1.95 (m, 1H), 1.24 (d, J=7.0 Hz, 0.75H), 1.06 (d, J=6.6 Hz, 2.25H), 0.95 (s, 9H), 0.90 (s, 9H); $^{13}$C-NMR (100.6 MHz, DMSO-d$_6$) δ 197.32, 197.06, 196.79, 171.46, 171.08, 170.98, 170.49, 170.33, 169.86, 169.34, 161.15, 160.88, 160.62, 138.54, 138.04, 128.53, 128.40, 127.43, 127.27, 127.21, 126.98, 112.32, 109.68, 107.04, 60.45, 59.80, 50.04, 49.87, 49.58, 48.44, 48.26, 42.60, 42.36, 36.81, 35.03, 34.28, 33.89, 30.74, 29.84, 26.83, 15.54; HRMS calcd for $C_{30}H_{46}F_2N_5O_6$ (MH$^+$) 610.3416, found: 610.3395.

Example 45

N1-[2-(1,3-benzoxazol-2-yl)-1-methyl-2-oxoethyl]-N4,N4-dimethyl-(2S)-2-{[(1S)-2,2-dimethyl-1-(neopentylcarboxamido)propyl]carboxamido}butanediamide (77, Table 5)

A mixture of 16 (265 mg, 0.81 mmol) and 10% Pd on carbon (79 mg) in ethanol (20 mL) was stirred under an atmosphere of hydrogen for 1 h. The solution was then filtered through a glass microfiber and concentrated under reduced pressure. The residue was dissolved in $CH_2Cl_2$ (6 mL) and Boc-Asn(γ-NMe$_2$)-OH (222 mg, 0.85 mmol), HOBt (220 mg, 1.63 mmol), i-Pr$_2$NEt (0.56 mL, 3.25 mmol) and EDC (169 mg, 0.88 mmol) were added. Additional i-Pr$_2$NEt was introduced to bring the pH above 8 and stirring was continued overnight. The resulting mixture was diluted with EtOAc and washed sequentially with 10% citric acid, 10% $Na_2CO_3$ and water and dried by passing through a plug of glass wool. Flash chromatography (EtOAc) gave the desired compound (314 mg, 95%) $^1$H-NMR (DMSO-d$_6$) δ 7.82–7.66 (m, 3H), 7.42–7.33 (m, 3H), 6.78 and 6.73 (2×d, J=7.8 and 7.5 Hz, 1H), 6.23–6.18 and 6.16–6.11 (2×m, 1H), 4.84–4.82 and 4.66–4.50 (2×m, 1H), 4.33–4.17 (m, 2H), 2.88, 2.77, 2.74 (3 ×s, 6H), 2.58–2.20 (m, 2H), 1.34 (s, 9H), 1.18–1.15 (m, 3H). This product was stirred in a mixture of $CH_2Cl_2$ (8 mL) and TFA (2 mL) for 2 h. After removal of the solvent, residual TFA was removed by azeotropic distillation with benzene using a rotary evaporator. The residue was dissolved in $CH_2Cl_2$ (6 mL) and Boc-Tbg-OH (188 mg, 0.81 mmol), HOBt (209 mg, 1.55 mmol), i-Pr$_2$NEt (0.54 mL, 3.10 mmol) and EDC (161 mg, 0.84 mmol) were added. Additional i-Pr$_2$NEt was introduced to bring the pH above 8 and stirring was continued overnight. The resulting mixture was diluted with EtOAc and washed sequentially with 10% citric acid, 10% $Na_2CO_3$ and water and dried by passing through a plug of glass wool. Flash chromatography (EtOAc) gave the desired compound (264 mg, 62%). $^1$H-NMR (DMSO-d$_6$) δ 7.89–7.82 and 7.73–7.68 (m, 4H), 7.42–7.33 (m, 2H), 6.45 (d, J=6.9 Hz, 1H), 6.19 and 6.06 (2×d, J=6.0 and 5.4 Hz, 1H), 4.84 and 4.68 (2×t, J=5.1 and 6.3 Hz, 1H), 4.61–4.51 (m, 1H), 4.33–4.23 (m, 1H), 3.84–3.77 (m, 1H), 2.89, 2.78, 2.72 (3 ×s, 6H), 2.58–2.27 (m, 2H), 1.38 (s, 9H), 1.12 (m, 3H), 0.86 and 0.84 (2×s, 9H). This product was stirred in a mixture of $CH_2Cl_2$ (8 mL) and TFA (2 mL) for 2 h. After removal of the solvent, residual TFA was removed by azeotropic distillation with benzene using a rotary evaporator.

The residue was dissolved in $CH_2Cl_2$ (6 mL) and tert-butylacetic acid (64 mg, 0.50 mmol), HOBt (129 mg, 0.96 mmol), i-Pr$_2$NEt (0.33 mL, 1.91 mmol) and EDC (99 mg, 0.52 mmol) were added. Additional i-Pr$_2$NEt was introduced to bring the pH above 8 and stirring was continued overnight. The resulting mixture was diluted with EtOAc and washed sequentially with 10% citric acid, 10% $Na_2CO_3$, water and dried by passing through a plug of glass wool. Flash chromatography (EtOAc) gave the desired compound (162 mg, 62%) which was immediately dissolved in $CH_2Cl_2$ (8 mL). Dess-Martin 30 periodinane (252 mg, 0.59 mmol) was added and the resulting mixture stirred for 1 h. A 1:1 mixture of 10% $Na_2S_2O_3$: saturated $NaHCO_3$ was introduced and stirring was continued until both layers were clear (10 min). The residue was extracted with $CH_2Cl_2$, washed with aqueous $NaHCO_3$, dried ($MgSO_4$), filtered and concentrated in vacuo. Flash chromatography using TLC grade silica gel (3% ethanol in EtOAc) afforded the compound as a colorless oil. This material was dissolved in a minimum amount of $CH_3CN$, diluted with water and lyophilized to afford the desired compound 77 as a white solid (99.3 mg, 61%). IR (KBr) υ 3311, 1713, 1657 cm$^{-1}$; $^1$H-NMR (DMSO-d$_6$), 2.7:1 mixture of diastereomers, δ 8.28 (d, J=5.7 Hz, 1H), 8.16 and 8.08 (2×d, J=7.5 and 7.5 Hz, 1H), 8.00 (d, J=8.1 Hz, 1H), 8.28 (d, J=8.1 Hz, 1H), 7.75–7.53 (m, 2H), 7.45–7.34 (m, 1H), 6.99 and 6.75 (2×S, 1H, hydrate), 5.30–5.22 and 4.41–4.35 (2×m, 1H), 4.62 and 4.52 (2×q, J=6.0 and 7.2 Hz, 1H), 4.18 and 4.13 (2×d, J=9.0 and 8.4 Hz, 1H), 2.91 and 2.82 (2×S, 3H), 2.77 and 2.71 (2×S, 3H), 2.73–2.59 (m, 2H), 2.20 and 2.16 (2×d, J$_{AB}$=12.6 and 12.9 Hz, JH), 2.03 and 2.02 (2×d, J$_{AB}$=12.6 and 12.9 Hz, 1H), 1.42 and 1.06 (d, J=7.2 and 6.9 Hz, 3H), 0.95–0.87 (m, 18H); HRMS calcd for $C_{28}H_{42}N_5O_6$ (MH$^+$) 544.3135, found: 544.3154; Anal ($C_{28}H_{41}N_5O_6$) C, H, N.

Example 46

Diphenyl N4,N4-dimethyl-N1-(1-aminoethylphosphinate)-(2S)-2-{[(1S)-2,2-dirmethyl-1-(neopentylcarboxamido)propyl]carboxamido}butanediamide (79, Table 5)

To a warm solution of 1-(N-Benzyloxycarbonyl)-aminoethylphosphonate (Oleksyszyn, J.; Subotkowska, L.; Mastalerz, P. Diphenyl 1-aminoalkanephosphonates. *Synthesis*, 1979, 985–986) (8.50 g, 21.0 mmol) in ethanol (75 mL) was added a solution of 4 N HCl/dioxane (5.25 mL, 21.0 mmol) and 10% Pd/C (850 mg, 10% w/w). The mixture was stirred vigorously, flushed three times with hydrogen and stirred 16 h under a hydrogen atmosphere (balloon). The catalyst was filtered through Celite and the filtrate concentrated in vacuo. The residual oil was triturated in Et$_2$O (150 mL) until a white solid was obtained. This was filtered and dried to give 6.10 g (93%) of the corresponding hydrochloride salt. $^1$H-NMR (DMSO-d$_6$) δ 9.18 (s, 3H), 7.40–7.44 (m, 4H), 7.24–7.27 (m, 6H), 4.18 (dt, J=7.2, 20.3 Hz, 1H), 1.61 (dd, J, =7.2 Hz, J$_2$ 18.0 Hz, 3H). A stirred solution containing Boc-Asn(γ-NMe$_2$)-OH (500 mg, 1.92 mmol), the hydrochloride salt from above (663 mg, 2.11 mmol), i-Pr$_2$NEt (836 μL, 4.80 mmol) and TBTU (677 mg, 2.11 mmol) in DMF (8 mL) was stirred initially at 0° C. for 15 min, and then at rt for 3 h under an atmosphere of nitrogen. The solution was poured into brine and the product extracted with EtOAc (2×25 mL). The combined organic extracts were washed sequentially with 5% aqueous $NaHCO_3$, 1 M citric acid, and brine. The organic phase was dried ($MgSO_4$), filtered and concentrated in vacuo to give 0.975 g of an amorphous solid. The product was purified by flash chromatography (gradient 15–30% i-PrOH/hexane) to yield the coupled phosphonate derivative as an amorphous solid (0.81 g, 81%). HPLC (system A) 99.5%; $^1$H-NMR ($CDCl_3$) 1:1 mixture of diastereomers at $P_1$, δ 7.65–7.35 (m, 1H), 7.30–7.05 (m, 10H), 6.20–5.95 (m, 1H), 4.86–4.64 (m, 1H), 4.54–4.42 (m, 1H), 3.16–3.05 (m, 1H), 2.97–2.74 (m, 6H), 2.56–2.41 (m, 1H), 1.55–1.45 (m, 3H), 1.38 (s, 9H); FAB MS m/z: 520 ($MH^+$), 420 ($MH^+$–100). This material (0.75 g, 1.44 mmol) was treated with 4 N HCl/dioxane (30 min) before being concentrated in vacuo. The hydrochloride salt (1.44 mmol) was combined with Boc-Tbg-OH (0.40 g, 1.73 mmol), TBTU (0.555 g, 1.73 mmol) and i-$Pr_2$NEt (1.05 mL, 6.05 mmol) in DMF (8 mL) initially at 0° C. (15 min) and then at rt 16 h. The reaction mixture was diluted with EtOAc and washed sequentially with 5% aqueous $NaHCO_3$, 1 M citric acid, and brine. The organic phase was dried ($MgSO_4$), filtered and concentrated in vacuo. Purification by flash chromatography using TLC grade silica gel (20% i-PrOH/hexane) gave the desired dipeptide fragment as a white solid (0.773 g, 85%). $^1$H-NMR ($CDCl_3$) δ 8.06–7.80 (m, 1H), 7.50–7.40 (m, 1H), 7.38–7.10 (m, 10H), 5.24–5.12 (m, 1H), 4.86–4.68 (m, 2H), 3.84–3.76 (m, 1H), 3.21–3.07 (m, 1H), 2.95–2.78 (m, 6H), 2.58–2.35 (m, 1H), 1.61–1.49 (m, 3H), 1.43 (s, 9H), 0.96 (s, 9H); FAB MS m/z: 633 ($MH^+$), 533 ($MH^+$–100). This compound (0.70 g, 1.0 mmol) was treated with 4 N HCl/dioxane (30 min) before being concentrated in vacuo. The hydrochloride salt (1.0 mmol) was combined with tert-butylacetic acid (191 μL, 1.50 mmol), TBTU (0.385 g, 1.20 mmol) and i-$Pr_2$NEt (0.52 mL, 3.0 mmol) in DMF (10 mL) for 16 h. The reaction mixture was diluted with EtOAc and washed sequentially with 5% aqueous $NaHCO_3$, 1 M citric acid, and brine. The organic phase was dried ($MgSO_4$), filtered and concentrated in vacuo. Purification was performed by preparative HPLC to give compound 79 (155 mg, 25%). IR (KBr) υ 3289, 1642 $cm^{-1}$; $^1$H-NMR (DMSO-$d_6$), 2:1 mixture of diastereomers at $P_1$, δ 8.35 (d, J=8.9 Hz, 0.34H), 8.24 (d, J=7.3 Hz, 0.66H), 8.20 (d, J=9.2 Hz, 0.66H), 8.15 (d, J=7.6 Hz, 0.34H), 7.63 (d, J=8.6 Hz, 0.66H), 7.58 (d, J=8.6 Hz, 0.34H), 7.33–7.40 (m, 4H), 7.14–7.23 (m, 6H), 4.57–4.72 (m, 2H), 4.18 (d, J=8.6 Hz, 0.66H), 4.17 (d, J=8.6 Hz, 0.34H), 3.62 (s, broad, 1H), 2.94 (s, 1H), 2.88 (s, 2H), 2.79 (s, 1H), 2.77 (s, 2H), 2.59–2.74 (m, 1H), 2.20 (d, J=12.7 Hz, 0.66H), 2.17 (d, J=12.7 Hz, 0.34H), 2.02 (d, J=12.7 Hz, 0.66H), 1.98 (d, J=12.7 Hz, 0.34H), 1.44 (d, J=7.3 Hz, 1.5H), 1.39 (d, J=7.3 Hz, 1.5H), 0.95 (s, 5.9H), 0.92 (s, 5.9H), 0.91(s, 3.1H), 0.88 (s, 3.1H); HRMS calcd for $C_{32}H_{48}N_4O_7P$ ($MH^+$) 631.3260, found: 631.3279; Anal ($C_{32}H_{47}N_4O_7P$) C, H, N.

Example 47

N1-[2-(1,3-benzothiazol-2-yl)-1-methyl-2-oxoethyl]-
N4,N4-dimethyl-(2S)-2-{[(1S)-2,2-di-methyl-1-
(neopentylcarboxamido)propyl]
carboxamido}butanediamide (80, Table 5)

This compound was prepared from 14 using standard coupling methods and oxidation of the heterocyclic alcohol with the Moffatt-Pfitzner method. Final purification was performed by preparative HPLC. HPLC (system A) 99%, (system D) 100%; IR (KBr) υ 1642 $cm^{-1}$; $^1$H-NMR (400 MHz, DMSO-$d_6$), 1.5:1 mixture of diastereomers, δ 8.30–8.13 (m, 4H), 7.73–7.58 (m, 3H), 5.47–5.38 (m, 1H), 4.68–4.60 (m, 1H), 4.18–4.10 (m, 1H), 2.92 (s, 3H), 2.79 (s, 3H), 2.76–2.63 (m, 2H), 2.20 (d, J=12.5 Hz, 1H), 2.03 (d, J=12.5 Hz, 1H), 1.43 and 1.37–1.28 (d, J=7.3 Hz; m, 3H), 0.95 (s, 9H), 0.90 (s, 9H); FAB MS m/z: 560 ($MH^+$); HRMS calcd for $C_{28}H_{42}N_5O_5S$ ($MH^+$) 560.2906, found: 560.2896.

Example 48

N4,N4-dimethyl-N1-(1-methyl-2-[1,3]oxazolo[4,5-
b]pyridin-2-yl-2-oxoethyl)-(2S)-2-{[(1S)-2,2-
dimethyl-1-(neopentylcarboxamido)propyl]
carboxamido} butanediamide (81, Table 5)

This compound was prepared from 17 using standard coupling methods and oxidation of the heterocyclic alcohol with the Dess-Martin periodinane. Final purification was performed by preparative HPLC. 1:1 mixture of isomers; HPLC (system A) 97%, (system D) 98%; IR (KBr) υ 1703, 1682, 1643 $cm^{-1}$; $^1$H-NMR (400 MHz, DMSO-$d_6$) δ 11.39 and 11.30 (2×s, 1H), 8.19 (d, J=7.7 Hz, 1H), 7.96–7.83 (m, 1H), 7.63–7.56 (m, 2H), 7.39–7.32 (m, 2H), 7.06–6.95 (m, 1H), 4.65–4.46 (m, 2H), 4.25 and 4.22 (2×d, J=9.1 and 8.3 Hz, 1H), 2.95 and 2.91 (2×s, 3H), 2.77 and 2.66 (2×s, 3H), 2.72–2.45 (m, 2H), 2.18–2.00 (m, 2H), 1.17 and 1.10 (2×d, J=6.8 and 6.8 Hz, 3H), 0.98–0.85 (m, 18H); FAB MS m/z: 563 (M+19), 585 (M+18+23); HRMS calcd for $C_{27}H_{43}N_6O_7$ (M+19) 563.3193, found: 563.3207.

Example 49

N4,N4-dimethyl-N1-[1-methyl-2-(6-methyl-1,3-
benzoxazol-2-yl)-2-oxoethyl]-(2S)-2-{[(1S)-2,2-
dimethyl-1-(neopentylcarboxamido)propyl]
carboxamido}butanediamide (82, Table 5)

This compound was prepared from 20 using standard coupling methods and oxidation of the heterocyclic alcohol with the Dess-Martin periodinane. Final purification was performed by radial chromatography. HPLC (system A) 97%, (system C) 100%, (system D) 96%; IR (KBr) υ 1713, 1650, 1642 $cm^{-1}$; $^1$H-NMR (400 MHz, DMSO-$d_6$), 5:1 mixture of diastereomers, δ 8.36 and 8.15 (2×d, J=8.4 and 7.2 Hz, 1H), 8.31 and 8.25 (2×d, J=5.1 and 5.7 Hz, 1H), 7.89–7.86 (m, 1H), 7.73–7.69 (m, 1H), 7.63–7.51 (m, 1H), 7.41–7.36 (m, 1H), 5.29–5.21 and 4.74–7.68 (2×m, 1H), 4.67–4.50 (m, 1H), 4.14 and 3.91 (2×d, J=8.7 and 6.0 Hz, 1H), 2.93–2.58 (m, 8H), 2.49 (s, 3H), 2.23–2.18 (m, 1H), 2.05–2.01 (m, 1H), 1.45 and 1.41 (2×d, J=7.2 and 7.2 Hz, 3H), 0.97–0.87 (m, 18H); FAB MS m/z: 558 ($MH^+$); HRMS calcd for $C_{29}H_{44}N_5O_6$ ($MH^+$) 558.3292, found: 558.3307; Anal ($C_{28}H_{43}N_5O_6 \cdot \frac{1}{2}H_2O$) C, H, N.

Example 50

N4,N4-dimethyl-N1-[1-methyl-2-(5-methyl-1,3-
benzoxazol-2-yl)-2-oxoethyl]-(2S)-2-{[(1S)-2,2-
dimethyl-1-(neopentylcarboxamido)propyl]
carboxamido}butanediamide (83, Table 5)

This compound was prepared from 19 using standard coupling methods and oxidation of the heterocyclic alcohol with the Dess-Martin periodinane. Final purification was performed by flash chromatography. HPLC (system A) 96%, (system C) 99%, (system D) 94%; IR (KBr) υ 1713, 1642 $cm^{-1}$; $^1$H-NMR (400 MHz, DMSO-$d_6$), 1.7:1 mixture of diastereomers, B 8.38–8.06 (m, 2H), 7.81–7.67 (m, 2H), 7.63–7.37 (m, 2H), 5.28–5.20 and 4.73–4.67 (2×m, 1H), 4.62 and 4.55–4.48 (q, J=7.2 Hz; m, 1H), 4.13 and 3.91 (2×d, J=8.4 and 6.3 Hz, 1H), 2.93–2.46 (m, 8H), 2.49 (s, 3H), 2.21 and 2.20 (2×d, $J_{AB}$=12.3 and 12.4 Hz, 1H), 2.03 (2×d, $J_{AB}$=12.3 Hz, 1H), 1.45 and 1.41 (2×d, J=7.2 and 7.2 Hz, 3H), 0.97–0.87 (m, 18H); FAB MS m/z: 558 (MH$^+$); HRMS calcd for $C_{29}H_{44}N_5O_6$ (MH$^+$) 558.3292, found: 558.3307; Anal ($C_{29}H_{43}N_5O_6 \cdot \frac{1}{2}H_2O$) C, H, N.

Example 51

N4,N4-dimethyl-N1-[1-methyl-2-(4-methyl-1,3-benzoxazol-2-yl)-2-oxoethyl]-(2S)-2-{[(1S)-2,2-dimethyl-1-(neopentylcarboxamido)propyl]carboxamido}butanediamide (84, Table 5)

This compound was prepared from 18 using standard coupling methods and oxidation of the heterocyclic alcohol with the Dess-Martin periodinane. Final purification was performed by flash chromatography. HPLC (system A) 97%, (system C) 99%, (system D) 94%; IR (KBr) υ 1713, 1658, 1642 cm$^{-1}$; $^1$H-NMR (400 MHz, DMSO-d$_6$), 4:1 mixture of diastereomers, δ 8.38–8.08 (m, 2H), 7.71–7.15 (m, 4H), 5.32–5.24 and 4.74–4.68 (2×m, 1H), 4.63 and 4.55 (2×q, J=6.3 and 6.6 Hz, 1H), 4.14 and 3.91 (2×d, J=8.4 and 6.6 Hz, 1H), 2.93–2.48 (m, 11H), 2.20 (d, $J_{AB}$=12.6 Hz, 1H), 2.03 (d, $J_{AB}$=12.6 Hz, 1H), 1.45 and 1.42 (2×d, J=7.2 and 7.2 Hz, 3H), 0.97–0.87 (m, 18H); FAB MS m/z: 558 (MH$^+$); HRMS calcd for $C_{29}H_{44}N_5O_6$ (MH$^+$) 558.3292, found: 558.3307; Anal ($C_{29}H_{43}N_5O_6 \cdot \frac{1}{2}H_2O$) C, H, N.

Example 52

N4,N4-dimethyl-N1-[1-methyl-2-(7-methyl-1,3-benzoxazol-2-yl)-2-oxoethyl]-(2S)-2-{[(1S)-2,2-dimethyl-1-(neopentylcarboxamido)propyl]carboxamido}butanediamide (85, Table 5)

This compound was prepared from 21 using standard coupling methods and oxidation of the heterocyclic alcohol with the Dess-Martin periodinane. Final purification was performed by flash chromatography. HPLC (system A) 97%, (system C) 97%, (system D) 92%; IR (KBr) υ 1715, 1642 cm$^{-1}$; $^1$H-NMR (400 MHz, DMSO-d$_6$), 4:1 mixture of diastereomers, δ 8.37 and 8.15 (2×d, J=8.1 and 7.5 Hz, 1H), 8.34 and 8.28 (2×d, J=5.9 and 5.7 Hz, 1H), 7.83–7.20 (m, 4H), 5.26 and 4.73–4.68 (quint, J=6.3 Hz; m, JH), 4.62 and 4.57 (2×q, J=6.0 and 6.4 Hz, 1H), 4.14 and 3.90 (2×d, J=8.4 and 6.3 Hz, 1H), 2.93–2.58 (m, 8H), 2.54 (s, 3H), 2.21 and 2.20 (2×d, $J_{AB}$=12.3 and 12.6 Hz, 1H), 2.03 (d, $J_{AB}$=12.6 Hz, 1H), 1.45 and 1.42 (2×d, J=7.5 and 7.2 Hz, 3H), 0.97–0.87 (m, 18H); FAB MS m/z: 558 (MH$^+$); HRMS calcd for $C_{29}H_{44}N_5O_6$ (MH$^+$) 558.3292, found: 558.3307; Anal ($C_{29}H_{43}N_5O_6 \cdot \frac{1}{2}H_2O$) C, H, N.

Example 53

N4,N4-dimethyl-N1-[1-methyl-2-(methylcarbamoyl)-2-oxoethyl]-(2S)-2-{[(1S)-2,2-dimethyl-1-(neopentylcarboxamido)propyl]carboxamido}butanediamide (86, Table 6)

This compound was prepared according to the alternative procedure for the preparation of α-ketoamides (Example 2). Final purification was performed by preparative HPLC. HPLC (system C) 100%, (system D) 98%; IR (KBr) υ 3320, 1645 cm$^{-1}$; $^1$H-NMR (400 MHz, DMSO-d$_6$) δ 8.61 and 8.56 (2×m, 1H), 8.18–8.05 (m, 1H), 7.97 and 7.93 (2×d, J=6.4 and 6.3 Hz, 1H), 7.60 (br d, J=7.3 Hz, 1H), 5.03–4.90 (m, 1H), 4.65–4.50 (m, 1H), 4.13 and 4.12 (2×d, J=8.6 and 8.6 Hz, 1H), 2.94 (br s, 3H), 2.80 and 2.79 (2×s, 3H), 2.71–2.55 (m, 5H), 2.20 (d, J=12.4 Hz, 1H), 2.04 and 2.01 (2×d, J=12.7 and 12.7 Hz, 1H), 1.23 and 1.22 (2×d, J=7.3 and 7.0 Hz, 3H), 0.95 (s, 9H), 0.91 (br s, 9H); FAB MS m/z: 484.3 (MH$^+$), 506.3 (M+23); HRMS calcd for $C_{23}H_{42}N_5O_6$ (MH$^+$) 484.3135, found: 484.3148.

Example 54

N1-[2-(dimethylcarbamoyl)-1-methyl-2-oxoethyl]-N4,N4-dimethyl-(2S)-2-{[(1S)-2,2-dimethyl-1-(neopentylcarboxamido)propyl]carboxamido}butanediamide This compound was prepared according to the procedure for α-ketoamides (Example 2). Final purification was performed by preparative HPLC. HPLC (system C) 99%, (system D) 99%; IR (KBr) 3302, 1719, 1644 cm$^{-1}$; $^1$H-NMR (400 MHz, DMSO-d$_6$) δ 8.27 and 8.16 (2×d, J=6.4 and 6.7 Hz, 1H), 8.11 and 8.06 (2×d, J=7.6 and 7.9 Hz, 1H), 7.59 and 7.58 (2×d, J=8.6 and 8.0 Hz, 1H), 4.62–4.50 (m, 2H), 4.13 and 4.12 (2×d, J=8.0 and 8.6 Hz, 1H), 2.94 (br s, 3H), 2.86 and 2.85 (2×s, 6H), 2.80 (s, 3H), 2.72–2.56 (m, 2H), 2.23–2.16 (2×d, J=12.7 and 12.7 Hz, 1H), 2.10–1.90 (m, 1H), 1.30 and 1.29 (2×d, J=7.3 and 7.3 Hz, 3H), 0.95 (s, 9H), 0.90 (s, 9H); FAB MS m/z: 498.3 (MH$^+$), 520.3 (M+23); HRMS calcd for $C_{24}H_{44}N_5O_6$ (MH$^+$) 498.3292, found: 498.3309.

Example 55

N1-(2-[2-(benzyloxy)ethyl]carbamoyl-1-methyl-2-oxoethyl)-N4,N4-dimethyl-(2S)-2-{[(1S)-2,2-dimethyl-1-(neopentylcarboxamido)propyl]carboxamido}butanediamide (88, Table 6)

This compound was prepared according to the procedure for α-ketoamides (Example 2). Final purification was performed by preparative HPLC. HPLC (system C) 97%, (system D) 95%; IR (KBr) υ 3299, 1645, 1527 cm$^{-1}$; $^1$H-NMR (400 MHz, DMSO-d$_6$) δ 8.67 and 8.62 (2×t, J=5.7 Hz, 1H), 8.15 and 8.10 (2×d, J=7.5 and 6.3 Hz, 1H), 7.98 and 7.93 (2×d, J=6.3 and 6.3 Hz, 1H), 7.61 (d, J=8.4 Hz, 1H), 7.40–7.20 (m, 5H), 5.0–4.90 (m, 1H), 4.65–4.55 (m, 1H), 4.47 (s, 2H), 4.13 and 4.12 (2×d, J=8.7 and 8.4 Hz, 1H), 3.51 (t, J=6 Hz, 2H), 3.37–3.30 (m, 2H), 2.94 and 2.93 (2×s, 3H), 2.80 and 2.79 (2×s, 3H), 2.75–2.60 (m, 2H), 2.20 (d, J=12.6 Hz, 1H), 2.04 and 2.02 (2×d, J=12.6 and 12.6 Hz, 1H), 1.23 and 1.22 (2×d, J=7.2 and 7.2 Hz, 3H), 0.95 (s, 9H), 0.91 (s, 9H); FAB MS m/z: 604 (MH$^+$), 626 (M+23); HRMS calcd for $C_{31}H_{50}N_5O_7$ (MH$^+$) 604.3710, found: 604.3690.

Example 56

N1-2-[(1,3-benzodioxol-5-ylmethyl)carbamoyl]-1-methyl-2-oxoethyl-N4,N4-dimethyl-(2S)-2-{[(1S)-2,2-dimethyl-1-(neopentylcarboxamido)propyl]carboxamido}butanediamide (89, Table 6)

This compound was prepared according to the procedure for the preparation of α-ketoamides (Example 2). Final purification was performed by preparative HPLC. HPLC (system C) 99%, (system D) 100%; IR (KBr) υ 3302, 1644 cm$^{-1}$; $^1$H-NMR (400 MHz, DMSO-d$_6$) δ 9.14 and 9.09 (2×t, J=6.4 and 6.1 Hz, 1H), 8.13 and 8.08 (2×d, J=7.5 and 7.5 Hz, 1H), 8.01 and 7.96 (2×d, J=6.6 and 6.0 Hz, 1H), 7.60 (d, J=8.1 Hz, 1H), 6.85–6.80 (m, 2H), 6.73 (d, J=7.8 Hz, 1H), 5.97 (s, 2H), 5.02–4.86 (m, 1H), 4.65–4.51 (m, 1H), 4.31–4.08 (m, 3H), 2.92 (br s, 3H), 2.80 and 2.79 (2×s, 3H), 2.74–2.58 (m, 2H), 2.19 (br d, J=12.6 Hz, 1H), 2.03 and 2.02 (2×d, J=12.9 and 12.6 Hz, 1H), 1.23 (m, 3H), 0.94 and 0.90 (2×s, 18H); FAB MS m/z: 604 (MH⁺), 626 (M+23); HRMS calcd for $C_{30}H_{46}N_5O_8$ (MH⁺) 604.3347, found: 604.3333.

Example 57

N1-2-[(1H-benzo[d]imidazol-2-ylmethyl) carbamoyl]-1-methyl-2-oxoethyl-N4,N4-dimethyl-(2S)-2-{[(1S)-2,2-dimethyl-1-(neopentylcarboxamido)propyl]carboxamido} butanediamide (90, Table 6)

This compound was prepared according to the procedure for α-ketoamides (Example 2). Final purification was performed by preparative HPLC. HPLC (system C) 93%, (system D) 87%, IR (KBr) υ 3294, 1663, 1522 cm⁻¹; ¹H-NMR (400 MHz, DMSO-d₆) δ 9.41 and 9.35 (2×t, J=10.8 and 10.5 Hz, 1H), 8.64 (m, 0.5H), 8.18 and 8.09 (2×t, J=14.3 and 15.2 Hz, 2H), 7.99 (d, J=6.4 Hz, 0.5H), 7.78–7.52 (m, 3H), 7.48–7.34 (m, 2H), 6.48–6.20 (br d, 1H), 5.08–4.93 (m, 1H), 4.78–4.51 (m, 3H), 4.20–4.05 (m, 1H), 2.96, 2.93, 2.92 and 2.90 (4 ×s, 3H), 2.80, 2.79, 2.76, and 2.72 (4 ×s, 3H), 2.71–2.55 (m, 2H), 2.20 and 2.17 (2×d, J=12.4 and 9.8 Hz, 1H), 2.03 and 2.02 (2×d, J=12.7 and 12.7 Hz, 1H), 1.28 and 1.275 (2×d, J=7.3 and 7.3 Hz, 2H), 0.95 (s, 9H), 0.94–0.84 (m, 9H); FAB MS m/z: 600.6 (MH⁺), 618.6 (M+19); HRMS calcd for $C_{30}H_{46}N_7O_6$ (MH⁺) 600.3509, found: 600.3488.

Example 58

N4,N4-dimethyl-N1-(1-methyl-2-oxo-2-[(1S)-1-phenylethyl]carbamoylethyl)-(2S)-2-{[(1S)-2,2-dimethyl-1-(neopentylcarboxamido)propyl] carboxamido} butanediamide (91, Table 6)

This compound was prepared according to the procedure for α-ketoamides (Example 2). Final purification was performed by preparative HPLC. HPLC (system C) 99%, (system D) 98%; IR (KBr) υ 3300, 1647 cm⁻¹; ¹H-NMR (400 MHz, DMSO-d₆) δ 9.11 and 9.07 (2×d, J=8.6 and 8.6 Hz, 1H), 8.12 and 8.09 (2×d, J=7.9 and 7.3 Hz, 1H), 8.01 and 7.93 (2×d, J=6.4 and 6.3 Hz, 1H), 7.60 (m, 1H), 7.37–7.17 (m, 5H), 5.01–4.86 (m, 2H), 4.67–4.51 (m, 1H), 4.14 and 4.13 (2×d, J=8.6 and 8.6 Hz, 1H), 2.93 and 2.92 (2×s, 3H), 2.79 (br s, 3H), 2.73–2.54 (m, 2H), 2.19 (d, J=12.7 Hz, 1H), 2.06 and 2.01 (2×d, J=8.3 and 8.3 Hz, 1H), 1.44–1.37 (m, 3H), 1.24 and 1.17 (2×d, J=7.6 and 7.3 Hz, 3H), 0.94 (s, 9H), 0.91 and 0.90 (2×s, 9H); FAB MS m/z: 574.4 (MH⁺), 596.3 (M+23); HRMS calcd for $C_{30}H_{48}N_5O_6$ (MH⁺) 574.3605, found: 574.3586.

Example 59

N4,N4-dimethyl-N1-(1-methyl-2-oxo-2-[(1R)-1-phenylethyl]carbamoylethyl)-(2S)-2-{[(1S)-2,2-dimethyl-1-(neopentylcarboxamido)propyl] carboxamido} butanediamide (92, Table 6)

This compound was prepared according to the procedure for (α-ketoamides (Example 2). Final purification was performed by preparative HPLC. HPLC (system C) 99%, (system D) 97%; IR (KBr) υ 3288, 1645, 1525 cm⁻¹; ¹H-NMR (400 MHz, DMSO-d₆) δ 9.11 and 9.05 (2×d, J=8.3 and 8.6 Hz, 1H), 8.13 and 8.07 (2×d, J=7.3 and 7.6 Hz, 1H), 8.00 and 7.95 (2×d, J=6.4 and 6.4 Hz, 1H), 7.59 (d, J=8.6 Hz, 1H), 7.37–7.18 (m, 5H), 5.02–4.84 (m, 2H), 4.63–4.51 (m, 1H), 4.14 and 4.12 (2×d, J=8.6 and 8.6 Hz, 1H), 2.91 and 2.87 (2×s, 3H), 2.80 and 2.77 (2×s, 3H), 2.73 and 2.53 (m, 2H), 2.19 and 2.18 (2×d, J=12.7 and 12.4 Hz, 1H), 2.09–1.98 (m, 1H), 1.42 (d, J=7.0 Hz, 3H), 1.23 and 1.19 (2×d, J=7.3 and 7.0 Hz, 3H), 0.95 (br s, 9H), 0.91 and 0.90 (2×s, 9H); FAB MS m/z: 574.4 (MH⁺), 596.3 (M+23); HRMS calcd for $C_{30}H_{48}N_5O_6$ (MH⁺) 574.3605, found: 574.3591.

Example 60

N4,N4-dimethyl-N1-(1-methyl-2-oxo-2-[(1R)-1-phenylpropyl]carbamoyl-ethyl)-(2S)-2-{[(1S)-2,2-dimethyl-1-(neopentylcarboxamido)propyl] carboxamido} butanediamide (93, Table 6)

This compound was prepared according to the procedure for (α-ketoamides (Example 2). Final purification was performed by preparative HPLC. HPLC (system C) 100%, (system D) 96%; IR (KBr) υ 3297, 1647 cm⁻¹; ¹H-NMR (400 MHz, DMSO-d₆) δ 9.07 and 9.02 (2×d, J=8.6 and 8.9 Hz, 1H), 8.13 and 8.06 (2×d, J=7.7 and 7.2 Hz, 1H), 7.99 and 7.94 (2×d, J=5.9 and 5.9 Hz, 1H), 7.59 (d, J=8.3 Hz, 1H), 7.40–7.18 (m, 5H), 4.98–4.84 (m, 1H), 4.75–4.65 (m, 1H), 4.63–4.55 (m, 1H), 4.13 (2×d, J=8.4 and 8.4 Hz, 1H), 2.92 and 2.88 (2×S, 3H), 2.80 and 2.77 (2×S, 3H), 2.75–2.58 (m, 2H), 2.19 and 2.18 (2×d, J=12.6 and 12.6 Hz, 1H), 2.03 and 2.02 (2×d, J=12.6 and 12.3 Hz, 1H), 1.87–1.69 (m, 2H), 1.23 and 1.17 (2×d, J=7.2 and 7.2 Hz, 3H), 0.95 and 0.94 (2×S, 9H), 0.91 and 0.90 (2×S, 9H), 0.87–0.78 (m, 3H); FAB MS m/z: 588.7 (MH⁺), 610.7 (M+23); HRMS calcd for $C_{31}H_{50}N_5O_6$ (MH⁺) 588.3761, found: 588.3744; Anal ($C_{31}H_{49}N_5O_6 \cdot H_2O$) C, H, N.

Example 61

Compounds 94 to 98 from Table 7 and 305, 309 and 310 from Table 8 were synthesized according to route (b), Scheme 5. Compounds 301 to 303 and 306 to 308 from Table 8 were synthesized according to the procedure of example 43. Compound 304 was synthesized according to the procedure of example 45.

Compound 312 was synthesized in the following manner:

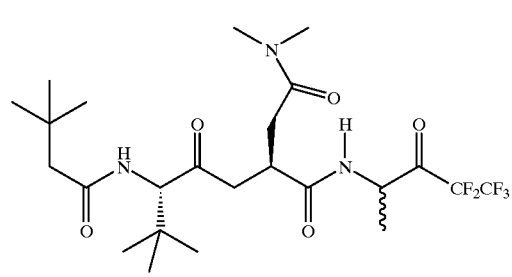

312

N⁴,N⁴-Dimethyl-N¹-[1-(R/S)-methyl-2-oxo-3,3,4,4,4-pentafluorobutyl]-(2S)-2-{3-[(3,3-dimethyl-1-oxobutyl)-amino]-4,4-dimethyl-2-oxopentyl}-butanediamide A solution of ketomethylene intermediate (2.42 g, 5.24 mmol, benzyl 6,6-dimethyl-(2S)-2-(2-dimethylamino-2-oxoethyl)-(5S)-5-[(tert-butoxycarbonyl)amino]-4-oxoheptanoate prepared according to Moss et al., (J. Med. Chem., 1996, 39, 4173–4180) in 4N HCl/dioxane (30 mL) was stirred at ambient temperature for 1.5 h. After removal of the solvent, the residue was co-evaporated twice with $CH_3CN$ then dissolved in $CH_3CN$ (50 mL) followed by the addition of i-PrNEt (2.74 mL, 15.72 mmol), tert-butyl acetic acid (0.67 ml, 5.24 mmol) and TBTU (1.70 g, 5.29 mmol). After stirring overnight at room temperature, the solvent was evaporated to dryness. The residue was dissolved in EtOAc and the solution washed sequentially with 10% aq. HCl, sat. NaHCO$_3$ solution and brine, and dried (MgSO$_4$). Evaporation of the solvent to dryness gave the desired amide derivative as a brown gummy residue [2.41 g, FAB MS, m/z: 461(MH$^+$), 483(M+Na)$^+$]. The crude amide was dissolved in EtOH and the solution stirred at room temperature in the presence of 10% Pd/C (250 mg) under an atmosphere of H$_2$ for 18 h. After filtration of the catalyst and evaporation of the solvent to dryness, the oily residue [(1.90 g, FAB MS, m/z: 399 (MH$^+$) corresponding to the ethyl ester derivative] was dissolved in a 1:1 mixture of MeOH-water (75 mL) and solid NaOH (758 mg) was added. The solution was stirred for 3 h at room temperature and the solvent was evaporated to dryness. The residue was dissolved in water, the solution acidified to pH 2 with 10% aq. HCl, extracted with EtOAc and the combined organic layers were washed with brine. Evaporation of the solvent to dryness gave the desired acid as a white foam [1.36g, FAB MS, m/z: 371(MH)$^+$ for. $C_{19}H_{34}N_2O_5$].

To a solution of the crude acid (370 mg) in CH$_3$CN (50 mL) was added (3R/S, 4R/S)-4-amino-1,1,1,2,2-pentafluoro-3-pentanol. HCl salt (229 mg, 1 mmol), TBTU (337 mg, 1.05 mmol), i-Pr$_2$NEt (0.70 ml, 4 mmol) and the mixture was stirred at room temperature for 3 h. After evaporation of the solvent to dryness, the residue was dissolved in EtOAc and the solution washed sequentially with 10% aq. HCl, aq. NaHCO$_3$ and brine. The solvent was evaporated to dryness to give the desired product (455 mg, 82% yield). FAB MS, m/z: 546(MH)$^+$ for $C_{24}H_{40}N_3O_5F_5$.

A cold solution of the crude hydroxytriamide product (454 mg, 0.81 mmol) in EtOAc was oxidized using the Dess-Martin periodinane (0.69 g, 1.63 mmol). After the usual isolation procedure, the crude product (398 mg) was purified by flash chromatography using a 4:1 EtOAc-hexane mixture to give the title compound (128 mg). FAB MS, m/z: 544.4 (MH$^+$), 562.4 (M+H$_2$O)$^+$ for $C_{24}H_{38}N_3O_5F_5$.

Example 62

Solid Phase Synthesis of Activated Ketones:

As shown in the following table, the peptidyl trifluoromethyl ketones and α-ketoamides of a wide chemical diversity were obtained in 12%–37% overall yield from the corresponding starting resin 103 described in Example 1. The crude material, which typically showed an homogeneity of 60–80% by reversed phase HPLC could easily be purified by semi-preparative HPLC. Since the trifluoromethyl ketone and α-ketoamide fragments 109 were racemic, the desired inhibitors were usually isolated as a 1:1 mixture of diastereomers. In some cases each isomer could be separated during the purification but in most cases, the inhibitors were subjected to biological testing as a mixture of isomers at the activated ketone center.

Specifically, compound 218 was synthesized in the following manner:

This compound was prepared on solid phase using the semicarbazone-derived resin (103 X'=C(O)NH-Bn). The solid-phase synthesis as well as the cleavage condition is identical to the one reported in example 1. Yield: 33%; HPLC (phosphate): 81%; $^1$H-NMR (400 MHz, DMSO-d$_6$), δ 9.18 (t, J=6.4 Hz, 1 H), 9.14 (s, 1 H), 8.39–8.26 (m, 1 H), 8.08–7.89 (m, 3 H), 7.75 (t, J=9.5 Hz, 1 H), 7.60 (broad s, 3 H), 7.34–7.22 (m, 6 H), 6.99 (d, J=8.3 Hz, 2 H), 6.61 (d, J=8.6 Hz, 2 H), 6.33–6.22 (m, 0.7 H), 4.98–4.94 (m, 2 H), 4.49–4.43 (m, 1 H), 4.33–4.00 (m, 6 H), 3.48 (t, J=5.8 Hz, 2 H), 2.96–2.91 (m, 1 H), 2.74–2.66 (m, 2 H), 2.05–1.90 (m, 1 H), 1.83 (s, 3 H), 1.65–1.45 (m, 4 H), 1.35–1.24 (m, 1 H), 1.26 (t, J=6.4 Hz, 2 H), 0.98–0.93 (m, 1 H), 0.86–0.82 (m, 6 H); FAB-MS (ES$^+$) calc for $C_{36}H_{52}N_7O_9$: 726; found: 726.

The IC$_{50}$ of compound 218 was found to be 9.4 μM.

| Cpd # | Sequence | Overall yield (%) |
|---|---|---|
| 201 | Val-Phe-Ser(O-t-Bu)-Asp-Ala(d,l)-CF$_3$ | 22 |
| 202 | Val-Phe-Ser(O-t-Bu)-Asp(O-t-Bu)Ala(d,I)-CF$_3$ | 14 |
| 203 | Ac-Asn-Asp(O-Bn)-Leu-Ala(d,l)-CF$_3$ | 40 |
| 204 | Ph-C(O)Glu-Tyr-Gly-Leu-Ala(d,l)-CF$_3$ | 68 |
| 205 | Ac-Phe-Leu-His-Thr-Ala(d,l)-CF$_3$ | 19 |
| 206 | Ac-Phe-Leu-His-Thr-(O-tBu)Ala(d,l)-CF$_3$ | 6 |
| 207 | Ac-Gly-Val-Val-Asn-Ala(d,l)-CF$_3$ | 30 |
| 208 | Ac-Asp-Glu-Met-Glu-Glu-Abu(d,l)-CF$_3$ | 36 |
| 209 | Boc-Gly-Phe-Leu-Abu(d,l)-CF$_3$ | 23 |
| 210 | Boc-Val-Ser(O-Bn)-Gly-Asp(O-Bn)-Abu(d,l)-CF$_3$ | 29 |
| 211 | Asp(O-Bn)-Ala-Pro-Abu(d,l)-CF$_3$ | 40 |
| 212 | Boc-Ala-Ala-Pro-Val(d,l)-CF$_3$ | 33 |
| 213 | Ph-CH$_2$-C(O)-Tyr-Ala-Lys-Val(d,l)-CF$_3$ | 21 |
| 214 | Ac-Leu-Gly-Asp(O-Bn)-Ala-Val(d,l)-CF$_3$ | 18 |
| 215 | Ac-Gly-Ser(O-Bn)-Leu-Asp(O-Bn)-Val(d,l)-CF$_3$ | 18 |
| 216 | Ac-Phe-Val-Pro-Val(d or l)-CF$_3$ | 8 |
| 217 | Ac-Phe-Val-Pro-Val(d or l)-CF$_3$ | 11 |
| 218 | Ac-Ser-Tyr-Val-Lys-Ala(d,l)-C(O)-NH-CH$_2$-Ph | 33 |
| [SEQ ID NOS: 71&72] | | |
| 219 | Ac-Asn-Asp(OBn)-Leu-Ala(d,l)-C(O)-NH-CH$_2$-Ph | 40 |

Example 63

ENZYMATIC ASSAYS

Material & Methods

Fluorescence measurements were recorded on a Perkin-Elmer LS-50B spectrofluorimeter equiped with a plate reader accessory. UV measurements were recorded on a Thermomax microplate reader from Moleculer Devices. All specificity enzymes and their respective substrates were commercially available from the following suppliers: Boehringer Mannheim (Bovine pancreas α-chymotrypsin #103314 lot 13724423–58, porcine pancreas elastase #1027891 lot 83260521–23), Calbiochem (Human neutrophil elastase #324681 lot B12778, Human liver cathepsin B #219364 lot B14649, Succ-AAA-pNA #573459 Lot 510008), Sigma Chemical Co. (Succ-AAPF-pNA #S7388 lot 31H5805, Bachem (Z-FR-pNA #L-1242 lot 502774, Succ-AAV-pNA #L-1405, lot 116699).

HCMV N$_o$ protease assay: HCMV N$_o$ protease was assayed with an internally quenched fluorogenic substrate based on the maturation cleavage site (Abz-VVNASSRLY (3-NO$_2$)R-OH, $k_{cat}/K_M$=260 M$^{-1}$s$^{-1}$) . The fluorescence increase upon cleavage of the Ala-Ser amide bond was monitored using excitation λ=312 nm (slit 2.5 nm) and emission λ=415 nm (slit 5 nm). A protocol adaptable to a 96-well plate format was designed for the determination of IC$_{50}$ values of inhibitors. Briefly, 125 nM HCMV N$_o$ protease was pre-incubated for 5 hr at 30° C. with a range of sequentially diluted inhibitor concentrations (300 to 0.06 μM depending on the potency of each compound). After this period, enzymatic hydrolysis was initiated by addition of the fluorogenic substrate and the reaction was performed for 2 hr at 30° C. (≈30% conversion). No quenching was required before fluorescence measurement since the total scanning time by the plate reader accessory was brief relative to the duration of the reaction. The incubation buffer (essentially similar to the pre-incubation buffer) contained 50 mM Tris/HCl pH 8, 0.5M Na$_2$SO$_4$, 50 mM NaCl, 0.1 mM EDTA, 1 mM TCEP, 3% v/v DMSO and 0.05% w/v Casein. The final concentrations of HCMV N, protease (expressed in terms of total monomer concentration) and substrate were 100 nM and 5 μM respectively. IC$_{50}$ values were obtained through fitting of the inhibition curve to a competitive inhibition model using SAS NLIN procedure. The mode of inhibition was determined by measurements of the initial rates (in cuvettes) at various substrate (Abz-Tbg-Tbg-Asn(Me)$_2$-Ala-SSRLY(3-NO$_2$)R-OH) and inhibitor concentrations using the same conditions as above. Data was plotted according to the Cornish-Bowden method ([S]/v versus [I]) and Dixon method (1/v versus [I]) to visually assess the type of inhibition (Cornish-Bowden, A. A simple graphical method for determining the inhibition constants of mixed, uncompetitive and non-competitive inhibitors. *Biochem. J.*. 1974, 137, 143–144).

Specificity Assays

The specificity of the compounds was determined against a variety of serine proteases (Human leukocyte and porcine pancreatic elastases (HLE & PPE), bovine pancreas α-chymotrypsin) and one cysteine protease (Human liver cathepsin B). In all cases a 96-well plate format protocol using a calorimetric p-nitroanilide (pNA) substrate specific for each enzyme was used. Each assay included a 1 hr pre-incubation enzyme-inhibitor at 30° C. followed by addition of substrate and hydrolysis to ≈30% conversion as measured by scanning on a UV Thermomax microplate reader. Substrate concentrations were kept as low as possible compared to KM to reduce substrate competition. Compound concentrations varied from 300 to 0.06 μM depending on their potency. The final conditions for each assay were as followed: 50 mM Tris/HCl pH 8, 0.5 M Na$_2$SO$_4$, 50 mM NaCl, 0.1 mM EDTA, 3% DMSO, 0.01% Tween-20 with [100 μM Succ-AAPF-pNA and 250 pM α-chymotrypsin], [133 μM Succ-AAA-pNA and 8 nM porcine elastase], or [133 μM Succ-AAV-pNA and 8 nM leukocyte elastase]. 100 mM NaH$_2$PO$_4$ pH 6, 0.1 mM EDTA, 3% DMSO, 1 mM TCEP, 0.01% Tween-20, 30 μM Z-FR-pNA and 5 nM cathepsin B (the stock enzyme was activated in buffer containing 20 mM TCEP before use).

Example 64

Biological Data

TABLE 1

| Compound | Structure | IC$_{50}$ (μM) |
|---|---|---|
| 37 [SEQ ID NOS: 1 & 2] | 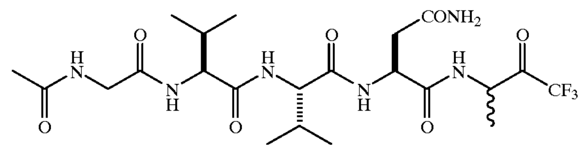 | 1.8 ± 0.3 |
| 38 [SEQ ID NOS: 3 & 4] | 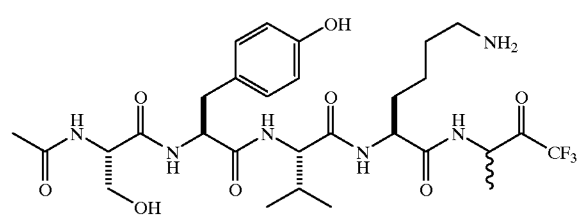 | 2.6 ± 0.4 |
| 39 [SEQ ID NOS: 5 & 6] | 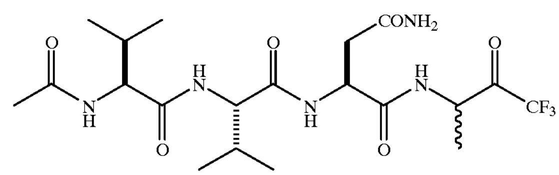 | 3.0 ± 0.3 |
| 40 | 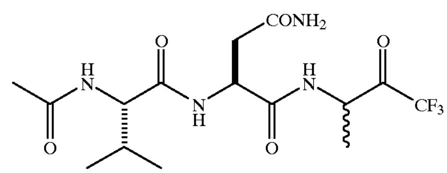 | 80 ± 15 |
| 41 | 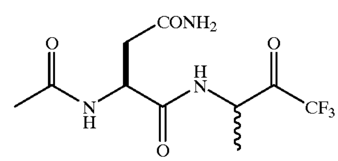 | >300 |

TABLE 1-continued
| Compound | Structure | IC$_{50}$ ($\mu$M) |
|---|---|---|
| 42 | 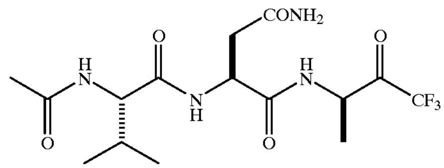 | >300 |
| 43 | 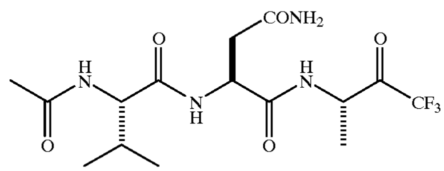 | 37 ± 4 |
| 44 [SEQ ID NOS: 7 & 8] | 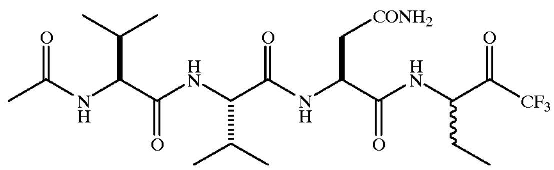 | 9 ± 2 |
| 45 [SEQ ID NOS: 9 & 10] | 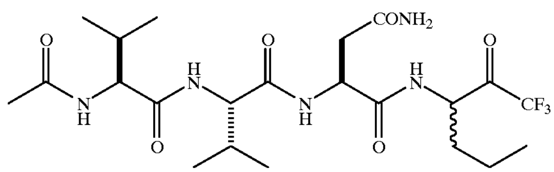 | >300 |
TABLE 2
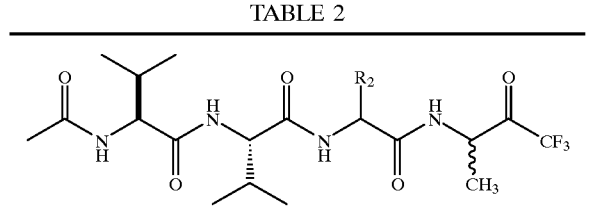
| Compound | R$_2$ | IC$_{50}$ ($\mu$M) |
|---|---|---|
| 39 [SEQ ID NOS: 5 & 6] | (O=C-NH$_2$) | 3.0 ± 0.3 |
| 46 [SEQ ID NOS: 11 & 12] | (O=C-NH$_2$, longer chain) | 9 ± 3 |
| 47 [SEQ ID NOS: 13 & 14] | (CH$_2$-COOH) | 24 ± 5 |
TABLE 2-continued
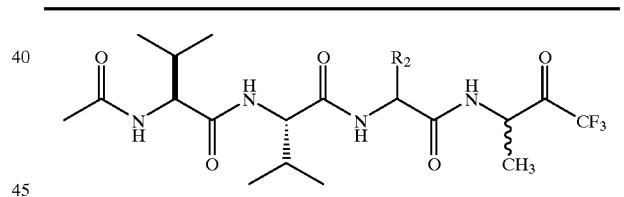
| Compound | R$_2$ | IC$_{50}$ ($\mu$M) |
|---|---|---|
| 48 [SEQ ID NOS 15 & 16] | (CH$_2$-OH) | 52 ± 6 |
| 49 [SEQ ID NOS: 17 & 18] | (H$_2$N-(CH$_2$)$_4$-) | 19 ± 3 |
| 50 [SEQ ID NOS: 19 & 20] | (CH$_2$-thiazole) | 6 ± 1 |

TABLE 2-continued

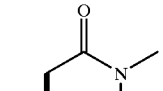

| Compound | R₂ | IC₅₀ (μM) |
|---|---|---|
| 51 [SEQ ID NOS: 21 & 22] | -CH₂C(O)N(CH₃)₂ | 2.0 ± 0.3 |
| 52 [SEQ ID NOS: 23 & 24] | isobutyl | 11 ± 2 |
| 53 [SEQ ID NOS: 25 & 26] | benzyl | 5 ± 1 |
| 54 [SEQ ID NOS: 27 & 28] | isopropyl | 61 ± 8 |
| 55 [SEQ ID NOS: 29 & 30] | CH₃ | 83 ± 15 |
| 56 [SEQ ID NOS: 31 & 32] | CH₃ | >300 |

TABLE 3

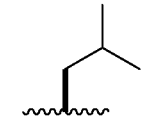

| Compound | R₃ | IC₅₀ (μM) |
|---|---|---|
| 51 [SEQ ID NOS: 21 & 22] | isopropyl | 2.0 ± 0.3 |
| 57 [SEQ ID NOS: 33 & 34] | sec-butyl | 4.4 ± 0.5 |
| 58 [SEQ ID NOS: 35 & 36] | tert-butyl | 1.1 ± 0.2 |
| 59 [SEQ ID NOS: 37 & 38] | neopentyl | 3.6 ± 0.5 |
| 60 [SEQ ID NOS: 39 & 40] | adamantyl | 6 ± 1 |
| 61 [SEQ ID NOS: 41 & 42] | -C(CH₃)₂CO₂H | 15 ± 4 |

TABLE 4

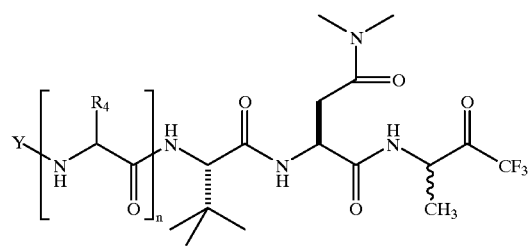

| Compound | Y | n | R₄ | IC₅₀ (μM) |
|---|---|---|---|---|
| 58 [SEQ ID NOS: 35 & 36] | acetyl | 1 | isopropyl | 1.1 ± 2 |

TABLE 4-continued
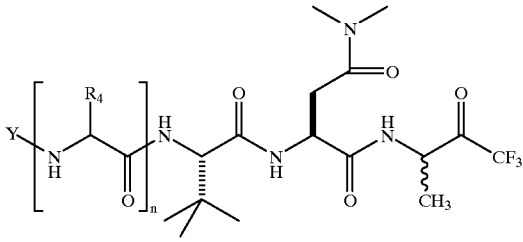
| Compound | Y | n | R₄ | IC₅₀ (μM) |
|---|---|---|---|---|
| 62 | 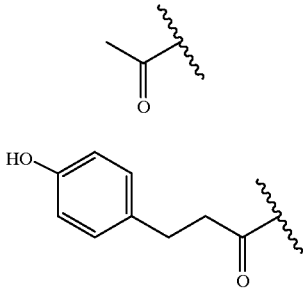 | 0 | — | 2.8 ± 0.4 |
| 63 | 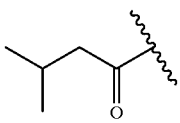 | 0 | — | 1.0 ± 0.3 |
| 64 | 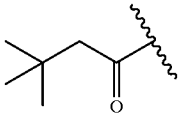 | 0 | — | 1.4 ± 0.1 |
| 65 | 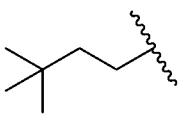 | 0 | — | 1.1 ± 0.1 |
| 66 | 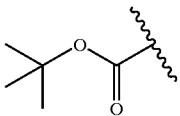 | 0 | — | 3.2 ± 0.2 |
| 67 | 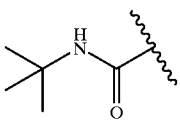 | 0 | — | 6 ± 1 |
| 68 | 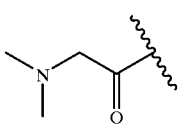 | 0 | — | 2.4 ± 0.2 |
| 69 [SEQ ID NOS: 43 & 44] | 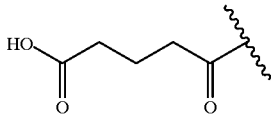 | 0 | — | 3.4 ± 0.5 |
| 70 |  | 0 | — | 1.6 ± 0.4 |

TABLE 5

| Compound | z | X | IC$_{50}$ ($\mu$M) |
|---|---|---|---|
| 65 | C | CF$_3$ | 1.1 ± 0.1 |
| 74 | C | CF$_2$CF$_3$ | 0.11 ± 0.01 |
| 75 | C | -CF$_2$-C(O)-NH-CH$_2$-C$_6$H$_5$ | 0.46 ± 0.06 |
| 76 | C | -C(O)-NH-CH$_2$-C$_6$H$_5$ | 0.20 ± 0.05 |
| 77 | C | 2-methylbenzoxazole | 0.6 ± 0.1 |
| 79 | P | (OPh)$_2$ | 0.66 ± 0.06 |
| 80 | C | 2-methylbenzothiazole | 1.1 ± 0.3 |
| 81 | C | 2-methylthiazolo[4,5-b]pyridine | 11 ± 2 |
| 82 | C | 2,6-dimethylbenzoxazole | 0.6 ± 0.1 |
| 83 | C | 2,5-dimethylbenzoxazole | 0.6 ± 0.1 |
| 84 | C | 2,4-dimethylbenzoxazole | 0.9 ± 0.2 |
| 85 | C | 2,7-dimethylbenzoxazole | 2.8 ± 0.3 |

TABLE 6

| Compound | X | IC$_{50}$ ($\mu$M) |
|---|---|---|
| 76 | -C(O)-NH-CH$_2$-C$_6$H$_5$ | 0.20 ± 0.05 |
| 86 | -C(O)-NHMe | 1.1 ± 0.3 |
| 88 | -C(O)-NH-CH$_2$-CH$_2$-O-CH$_2$-C$_6$H$_5$ | 0.14 ± 0.03 |

TABLE 6-continued
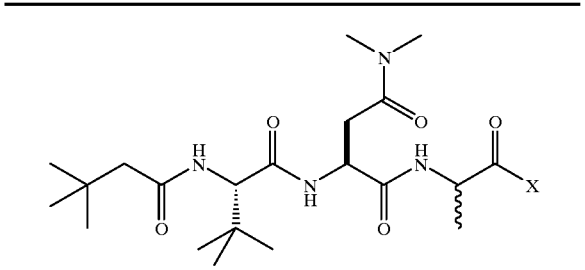
| Compound | X | IC$_{50}$ ($\mu$M) |
|---|---|---|
| 89 | 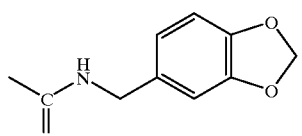 | 0.10 ± 0.01 |
| 90 | 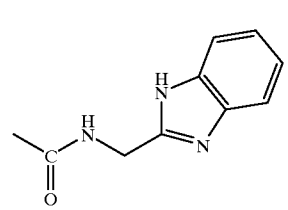 | 0.21 ± 0.05 |
| 91 | 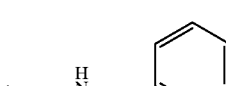 | 3.7 ± 0.8 |
TABLE 6-continued
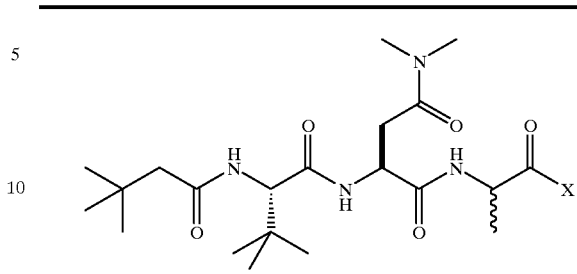
| Compound | X | IC$_{50}$ ($\mu$M) |
|---|---|---|
| 92 | | 0.28 ± 0.04 |
| 93 | | 0.11 ± 0.03 |
TABLE 7
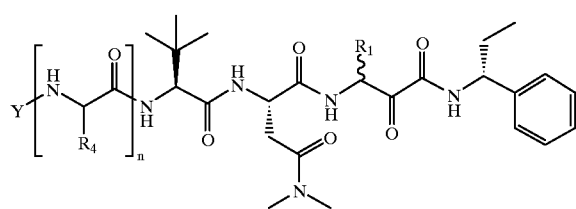
| Cpd | Y | n | R$_4$ | R$_1$ | IC$_{50}$ ($\mu$M) |
|---|---|---|---|---|---|
| 93 | | 0 | — | Me | 0.11 |
| 94 [SEQ ID NOS:45 & 46] | H | 1 | | H | 0.55 |

TABLE 7-continued

[structural formula of peptide with Y-NH-CHR₄-CO-NH-C(tBu)-CO-NH-CH(CH₂C(O)N(Me)₂)-CO-NH-CHR₁-CO-NH-CH(Et)-Ph]

| Cpd | Y | n | R₄ | R₁ | IC₅₀ (µM) |
|---|---|---|---|---|---|
| 95 [SEQ ID NOS:47 & 48] | tBuO-C(O)-CH₂- | 1 | tBu | H | 0.062 |
| 96 [SEQ ID NOS:49 & 50] | tBuO-C(O)-NH-(CH₂)₅-C(O)- | 1 | tBu | Me | 0.057 |
| 97 [SEQ ID NOS:51 & 52] | H₂N-(CH₂)₅-C(O)- | 1 | tBu | Me | 0.073 |

Example 65

An interesting compound related to 76 (Table 7), is the compound 98 (prepared according to the procedure of example 2) having the following structure:

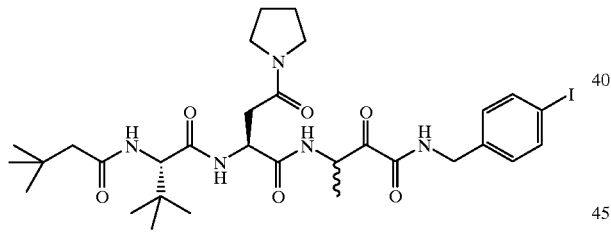

98

In the HCMV No protease assay, compound 98 had IC₅₀=0.34 µM. The compound with its incorporated iodine atom has the added benefit of being a useful compound for X-ray crystallographic studies.

Example 66

Table 8 illustrates further compounds synthesized according to the present invention:

TABLE 8

| Compound | Structure | IC₅₀ (µM) |
|---|---|---|
| 301 | Bob-Tbg-NH-CH(CH₂C(O)(OMe)NHPh)-C(O)-NH-CH(Me)-C(O)-C₂F₅ | 3.7 |

TABLE 8-continued

| Compound | Structure | IC$_{50}$ ($\mu$M) |
|---|---|---|
| 302 | 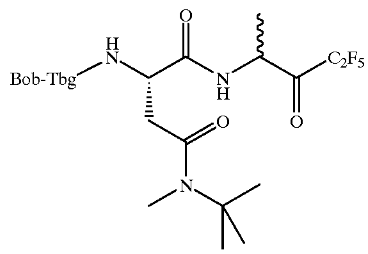 | 3.0 |
| 303 | 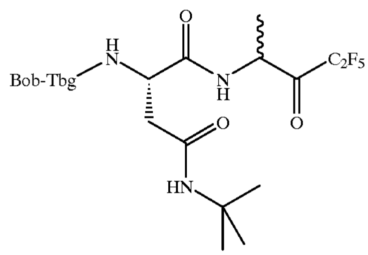 | 5.6 |
| 304 | 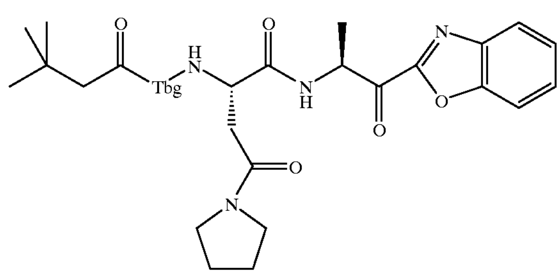 | 0.5 |
| 305 | 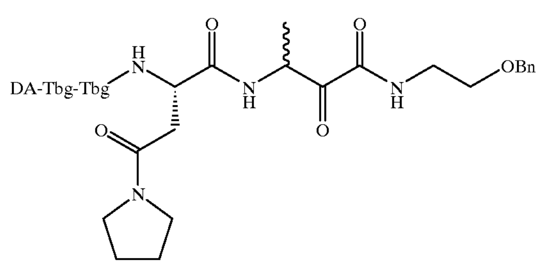 | 0.3 |
| 306 | 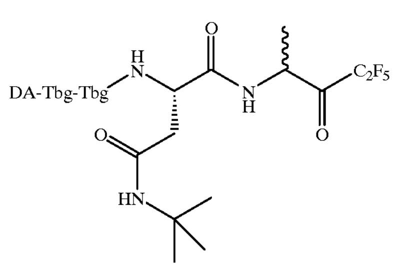 | 0.5 |

TABLE 8-continued

| Compound | Structure | IC$_{50}$ ($\mu$M) |
| --- | --- | --- |
| 307 | DA-Tbg-Tbg-NH-CH(CH$_2$CH$_2$C(O)N(CH$_3$)$_2$)-C(O)-NH-CH(C(O)C$_2$F$_5$)- | 2 |
| 308 | DA-Tbg-Tbg-NH-CH(CH$_2$C(O)-morpholine)-C(O)-NH-CH(C(O)C$_2$F$_5$)- | 0.3 |
| 309 | DA-Tbg-Tbg-NH-CH(CH$_2$C(O)N(CH$_3$)CH$_2$CH$_2$-2-pyridyl)-C(O)-NH-CH(C(O)C(O)NH-CH(CH$_2$CH$_3$)Ph)- | 0.12 |
| 310 | DA-Tbg-Tbg-NH-CH(CH$_2$SO$_2$NH$_2$)-C(O)-NH-CH(C(O)C(O)NH-CH(CH$_2$CH$_3$)Ph)- | 0.97 |
| 311 | (CH$_3$)$_3$CCH$_2$C(O)NH-CH(C(CH$_3$)$_3$)-C(O)-CH$_2$-CH(C(O)C(CH$_3$)$_3$)-C(O)NH-CH(CH$_3$)C(O)CF$_3$ | 6.8 |

TABLE 8-continued

| Compound | Structure | IC$_{50}$ ($\mu$M) |
|---|---|---|
| 312 | 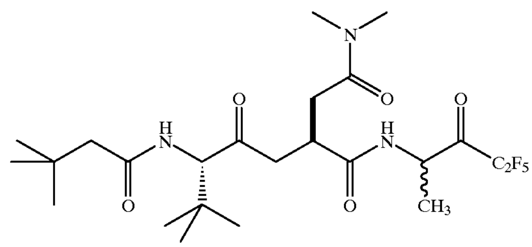 | 5.8 |

Results and Discussion

After optimizing with the peptide portion of the inhibitors, we considered the effect of changes to the activated carbonyl group. This functionality is of particular importance for the inhibition of serine proteases because of the formation of a reversible covalent bond with the active site serine. A number of effective activated carbonyl groups have been described in the literature suitable for use with peptidomimetic inhibitors (Mehdi, S. Synthetic and naturally occurring protease inhibitors containing an electrophilic carbonyl group. *Bioorganic Chem.* 1993, 21, 249–259). We investigated several major classes of these (Table 6). Compared with trifluoromethyl ketones, the use of pentafluoroethyl ketones, $\alpha,\alpha$-difluoro-$\beta$-ketoamides, $\alpha$-ketobenzoxazoles, $\alpha$-ketoamides and diphenyl phosphonates gave significant increases in activity.

Inhibitors 74 and 76 showed increases in potency by factors of ten and five respectively.

Several compounds were investigated further in order to better characterize their interactions with HCMV protease in terms of mode of inhibition. FIG. 1 shows a Dixon plot obtained for compound 76 which clearly demonstrates that this compound was a competitive inhibitor of HCMV protease.

Figure 2:
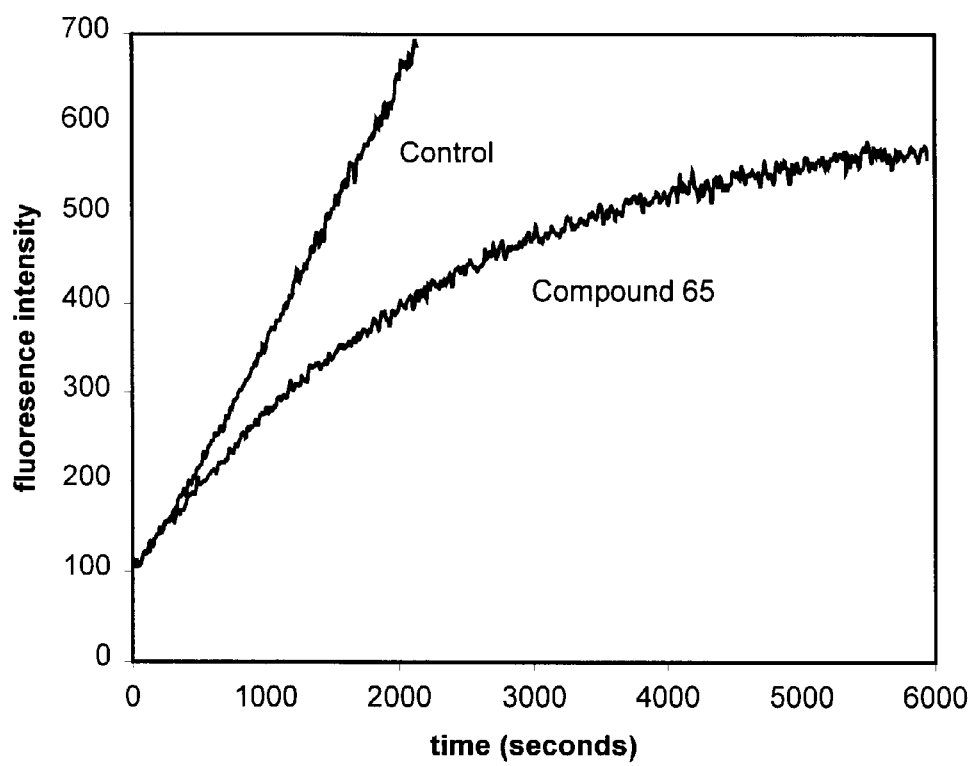
FIG. 2 is a Progress curve for the inhibition of HCMV protease by compound 65.

Compounds 63, 74 and 77 gave similar results indicating that these were all inhibiting in a competitive fashion (data not shown). It is well known that the interaction of trifluoromethyl ketone-based inhibitors with serine proteases is characterized by a slow onset of inhibition. This phenomenon has been explained by the observation that trifluoromethyl ketones exist in solution almost exclusively in the hydrated form (Edwards, P. D.; Bernstein, P. R. Synthetic inhibitors of elastase. *Medicinal Research Reviews*, 1994, 14, 128–194 and references cited therein). This produces a very low concentration of the inhibitory ketone form and results in time-dependent inhibition. As shown in FIG. 2, trifluoromethyl ketone 65 exhibits slow onset of inhibition with an apparent rate constant of $5.4 \times 10^{-3}$ s$^{-1}$.

Figure 3:
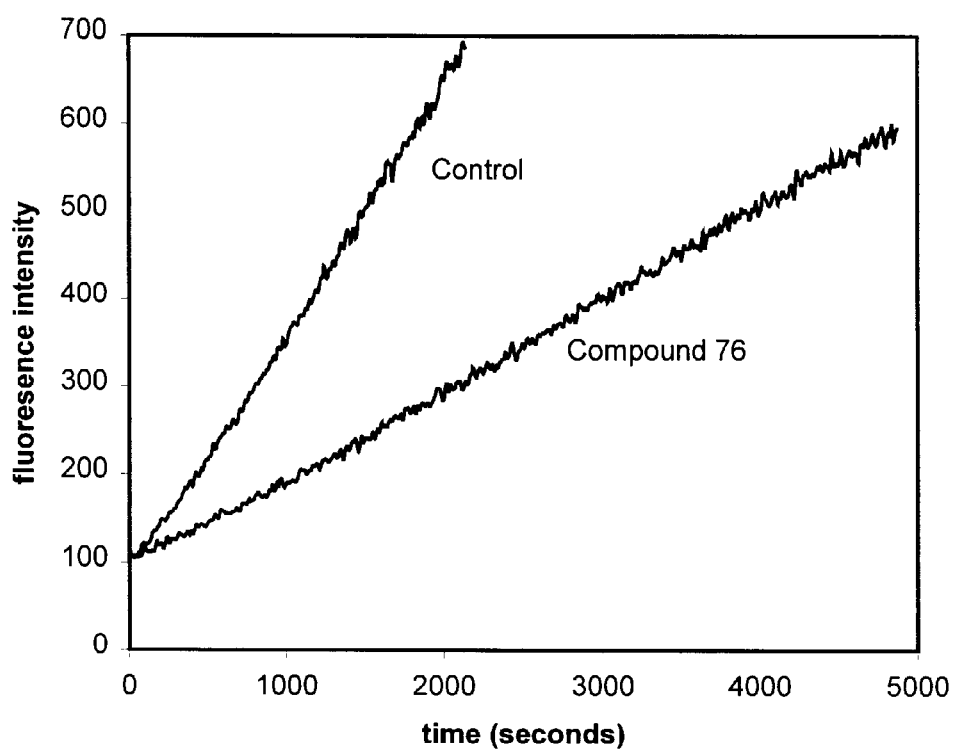
FIG. 3 is a Progress curve for the inhibition of HCMV protease by compound 76.

Other carbonyl activating groups were found to be less susceptible to this slow binding behavior. Shown in FIG. 3 is the progress curve obtained for compound 76, in which equilibrium is reached more rapidly.

Compound 74 showed slow binding behavior intermediate between that of 76 and 65, while 77 gave a progress curve comparable to 76. The very slow turnover rate shown by HMCV protease, coupled with slow binding kinetics for the present series of inhibitors has implications for the reliability of the enzymatic data. In order to ensure that the IC$_{50}$ values obtained were a true reflection of inhibitory power, we utilized assay conditions in which the inhibitors were pre-incubated with the enzyme before introduction of the substrate.

Specificity: To assess specificity, we investigated the inhibitory activity of our compounds towards a variety of serine proteases. Compounds 65, 74–85 were tested for inhibitory activity against porcine pancreatic elastase (PPE), human leukocyte elastase (HLE), bovine pancreatic $\alpha$-chymotrypsin (BPC), and the cysteine protease human liver cathepsin B (cat-B) (data not shown). Compounds 65, 74–79 all showed good specificity profiles against HLE, BPC and cat-B. Some of these compounds were weak inhibitors of PPE (which like HCMV protease shows a preference for alanine at P$_1$) but with specificity windows of 20 to 300 fold. One important exception to this last trend is $\alpha$-ketobenzoxazole 77 which was actually seven fold more potent against PPE than against HCMV protease. We carried out a limited SAR of benzoxazole substitutions to try to improve the specificity profile of these compounds. Benzothiazole 80 proved to be a potent inhibitor of HCMV (IC$_{50}$ 1.1 $\mu$M) and also interacted strongly with PPE (IC$_{50}$ 9 $\mu$M) Compound 81 was not an inhibitor of PPE but this specificity improvement was accompanied by an 18 fold loss in activity towards HCMV protease. The various methylated benzoxazoles 82–85 were all more potent inhibitors of PPE than of HCMV protease.

Compound 76 represented one of the most potent inhibitors of HCMV protease described so far. This structure also suggested the possibility of further increasing potency by extending the C-terminal amide moiety of this inhibitor into the S$_1$' binding pocket of the enzyme. The observation that the P$_1$' amino acids are fairly conserved (alanine or serine) prompted us to extend the C-terminus of the $\alpha$-ketoamide class of inhibitors in order to try to take advantage of interactions in the S' pocket.

To improve the potency of compound 93 further, extension onto the P4 residue was undertaken in the glycine and alanine P1 series (Table 7). Since the alanine and glycine series are equipotent, the following observations can be made. Incorporating a terminal amine on the P4 residue results in a 5 fold loss in potency whereas addition of a Boc group on this amine gives a 9 fold improvement in potency. Further extensions onto the P4 residue in the form of a Boc protected 6-aminocaproyl capping group gave compound 96 which had an IC$_{50}$ value of 75 nM. Removal of the Boc group from this inhibitor improved the potency by a factor of 2 to give compound 97 which is less than 40 nM in potency and represents the most potent compound of this series.

Table 8: compounds 301 to 312 summarize different substitutions of the P2 side-chain that gave potent inhibitors. These include various asparagine amide substitutions and a novel sulfonamide residue.

Table 9: compounds 401 to summarize different substitutions at P1'.

TABLE 9
| Cpd # | Structure | IC$_{50}$ ($\mu$M) |
|---|---|---|
| 401 | 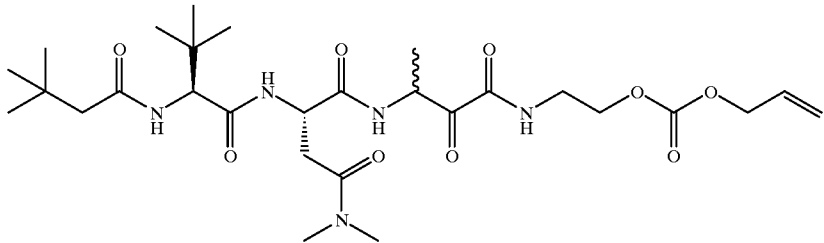 | 0.59 |
| 402 [SEQ ID NOS: 53 & 54] | 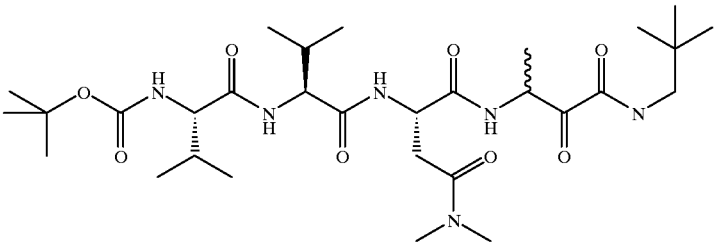 | 4.3 |
| 403 [SEQ ID NOS: 55 & 56] | 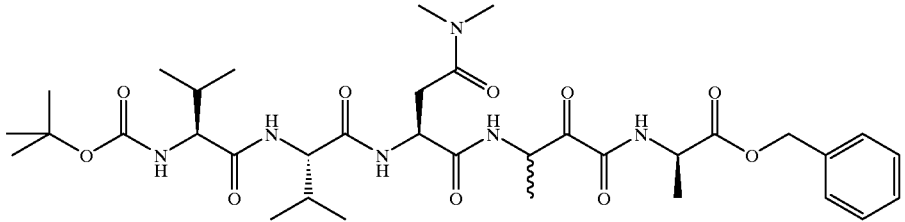 | 1.6 |
| 404 [SEQ ID NOS: 57 & 58] | 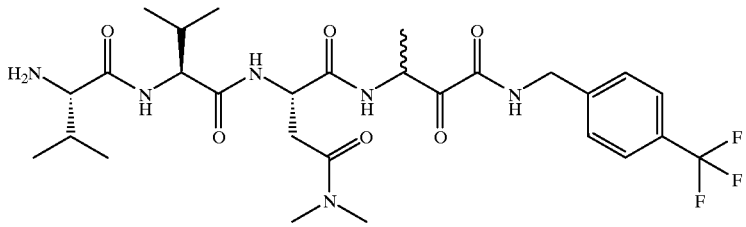 | 1.7 |
| 405 | 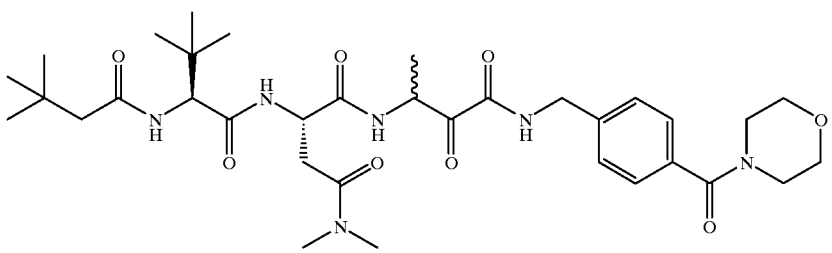 | 0.5 |
| 406 | 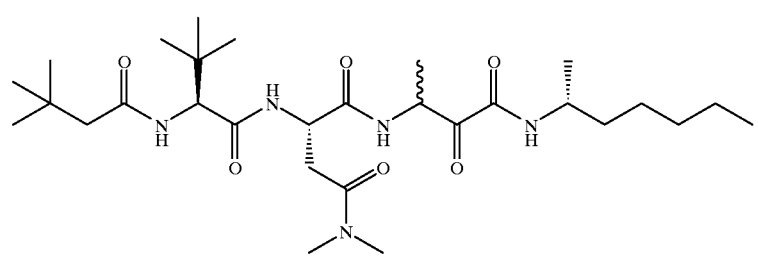 | 0.8 |

TABLE 9-continued

| Cpd # | Structure | IC$_{50}$ ($\mu$M) |
|---|---|---|
| 407 | 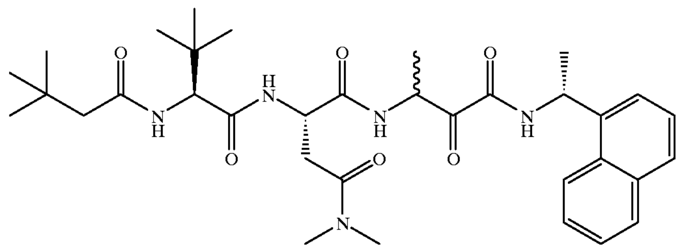 | 0.2 |
| 408 | 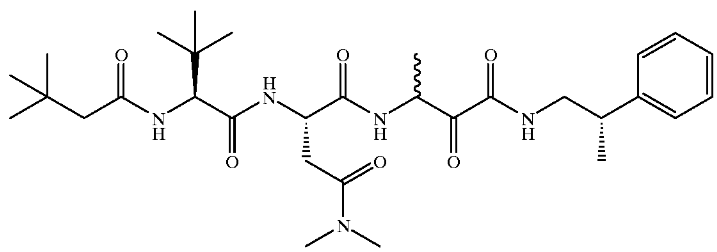 | 0.2 |
| 409 [SEQ ID NOS: 59 & 60] | 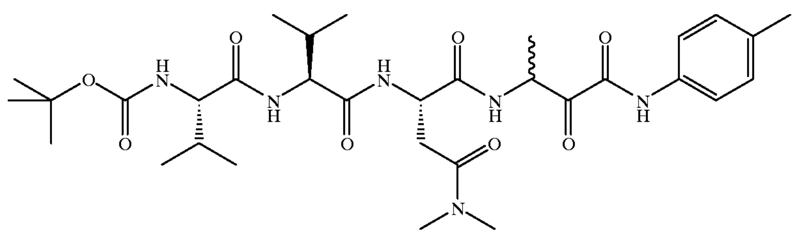 | 1.4 |
| 410 [SEQ ID NOS: 61 & 62] | 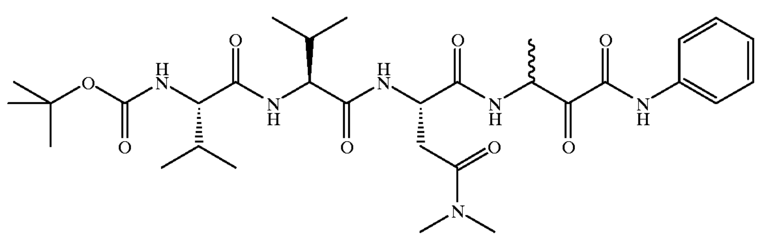 | 1.5 |
| 411 [SEQ ID NOS: 63 & 64] | 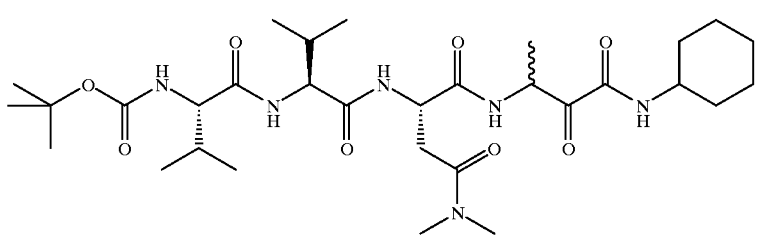 | 1.8 |
| 412 [SEQ ID NOS: 65 & 66] | 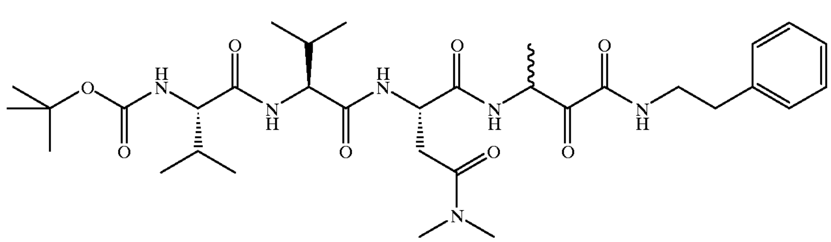 | 0.85 |

TABLE 9-continued

| Cpd # | Structure | IC$_{50}$ ($\mu$M) |
|---|---|---|
| 413 [SEQ ID NOS: 67 & 68] | 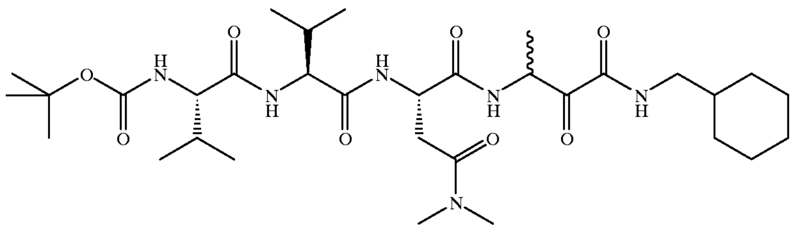 | 4.4 |
| 414 [SEQ ID NOS: 69 & 70] | 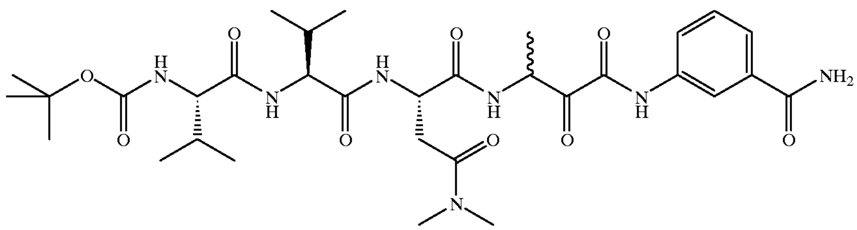 | 1.6 |

What is claimed is:

1. A compound of formula I:

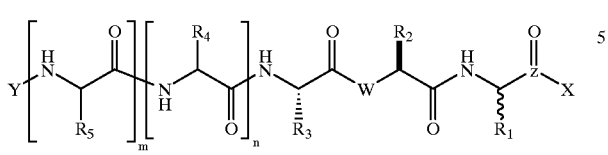

(I)

wherein z is C or P;
when z is C, then X is CF₃; C₂F₅; benzothiazole; oxazolo[4,5b]pyridine; or benzoxazole-R₇ wherein R₇ is H or methyl;
or X is CF₂CONH-R₆ or C(O)NH-R₆,
wherein R₆ is selected from:
C$_{0-10}$ alkyl optionally substituted with phenyl or cyclohexyl, said phenyl or cyclohexyl ring being optionally substituted with Me, halogen, —CF₃,—CH(Me)—C(O)—OBn; —C(O)NH₂; or —C(O)-morpholino, said phenyl or cyclohexyl ring optionally fused with a phenyl ring;
(CH₂)$_{1-3}$—O—(CH₂)$_{1-3}$-phenyl, said phenyl optionally substituted with halogen;
(CH₂)$_{1-3}$-2-benzimidazole;
(CH₂)$_{1-3}$-(3,4-methylenedioxybenzene); or
(CH₂)$_{1-3}$—O—C(O)—OCH₂CH=CH₂;
or, when z is P, then X is —(OPh)₂;
R₁ is H, Me, or Et;
R₂ is CH₂—SO₂NH₂; —(C$_{1-6}$ alkyl)thiazolo; —CH₂C(O)—(C$_{1-6}$ alkyl); —CH₂C(O)-pyrrolidino; —CH₂C(O)-morpholino; —(C$_{1-6}$ alkyl)amino; —(C$_{1-6}$ alkyl) amido optionally mono- or di-substituted with C$_{1-6}$ alkyl, said alkyl optionally substituted with pyridino;
W is NH, CH₂ or CH(CH₃);
R₃ is —C$_{1-12}$ alkyl; —(C$_{1-6}$ alkyl)C(O)OH; or adamantyl;
n is 0 or 1,
R₄, when n is 1, is —C$_{1-6}$ alkyl or —(C$_{1-6}$ alkyl)-aryl wherein said aryl is optionally substituted with OH;
m is 0 or 1,
R₅, when m is 1, is H or —CH₂OH;
and
Y is H; (CH₂)₂-t-Bu; or an acyl of formula:
—C(O)—(CH₂)$_{1-6}$—C(O)OH;
—C(O)—(CH₂)$_{1-6}$-Ph wherein Ph is optionally substituted with OH;
—C(O)—CH₂N(CH₃)₂;
—C(O)—R₉; —C(O)O—R₉; or —C(O)NH—R₉ wherein R₉ is C$_{1-6}$ alkyl; or
—C(O)—(CH₂)$_{1-6}$—NH₂ wherein the NH₂ group is optionally protected with an amino protecting group.

2. A compound of formula I:

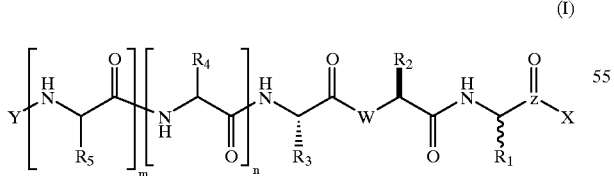

(I)

wherein z is C or P;
wherein when z is C, then X is CF₃; C₂F₅; 2-benzothiazole; 2-oxazolo[4,5b]pyridine; 2-benzoxazole-R₇, wherein R₇ is H, 4-Me, 5-Me, 6-Me, or 7-Me; or X is CF₂CONHR₆ or C(O)NHR₆, wherein R₆ is selected from:
C$_{1-7}$ alkyl, optionally substituted with cyclohexyl, naphthyl, or phenyl, said cyclohexyl, naphthyl or phenyl optionally substituted with Me, iodo, CF₃, —CH(Me)—C(O)—OBn; —C(O)NH₂, or —C(O)-morpholino;
(CH₂)₂—O—CH₂-phenyl;
CH₂-2-benzimidazole; or
CH₂—(3,4-methylenedioxybenzene);
or
when z is P, then X is (OPh)₂;
R₁ is H, methyl or ethyl;
R₂ is —CH₂-(4-thiazolo);
—(CH₂)$_{1-4}$—NH₂;
—CH₂—C(O)-tert-butyl;
—CH₂—C(O)—(N-pyrrolidino);
—CH₂—C(O)—(N-morpholino);
—CH₂SO₂NH₂;
—CH₂)$_{1-2}$-amido, the nitrogen of said amido optionally mono- or di-substituted with a substituent selected independently from: CH₃; t-Bu; phenyl; and —CH₂CH₂-(2-pyridino);
W is NH or CH₂;
R₃ is ethyl; isopropyl; t-Bu; CH₂-t-Bu; or adamantyl;
n is 0 or 1,
R₄, when n is 1, is isopropyl; t-Bu; or 4-hydroxybenzyl;
m is 0 or 1,
R₅, when m is 1, is H;
and
Y is H; —CH₂—CH₂-t-Bu; or an acyl of formula:
—C(O)CH₃;
—C(O)CH₂—CH(CH₃)₂;
—C(O)CH₂-t-Bu (DA-Tbg);
—C(O)(CH₂)₂-4-hydroxyphenyl;
—C(O)—(CH₂)₃—COOH;
—C(O)O-t-Bu (Boc);
—C(O)NH-t-Bu;
—C(O)CH₂—N(CH₃)₂; or
—C(O)(CH₂)$_{1-6}$NH₂, said amino group optionally protected with an amino protecting group.

3. A compound according to claim 2, wherein
when z is C, then X is CF₃; C₂F₅; benzothiazole; benzoxazole-R₇, wherein R₇ is H, 4-Me, 5-Me, 6-Me, or 7-Me; —CF₂CONH—CH₂-phenyl; or —C(O)NHR₆ wherein
R₆ is —CH(Me)(CH₂)₄CH₃; cyclohexyl; naphthyl; —CH₂-phenyl; —CH(CH₃)-phenyl; or —CH(CH₂CH₃)-phenyl; —CH₂4-iodophenyl; -phenyl-CH₃; -phenyl-CF₃; -phenyl-C(O)NH₂; -phenyl-C(O)-morpholino; -phenyl-CH(Me)—C(O)—OBn; —(CH₂)₂—O—CH₂-phenyl; —CH₂-2-benzimidazole; —CH₂-(3,4-methylenedioxybenzene); or —(CH₂)₂—O—C(O)—OCH₂CH=CH₂;
or
when z is P, then X is (OPh)₂;
R₁ is H or methyl;
R₂ is
—CH₂—C(O)—(N-pyrrolidino);
—CH₂—C(O)—(N-morpholino);
—CH₂SO₂NH₂;
—CH₂)C(O)NH₂;
—(CH₂)₂C(O)N(CH₃)₂;
—CH₂—C(O)—NH-t-Bu; or —$(CH_2)_2$—C(O)—$N(CH_3)CH_2CH_2$(2-pyridino);

W is NH;

$R_3$ is ethyl; isopropyl; or t-Bu;

$R_4$, when n is 1, is isopropyl; or t-Bu;

$R_5$, when m is 1, is H;

and

Y is H; or an acyl of formula:
- —C(O)$CH_3$;
- —C(O)$CH_2$—CH($CH_3$)$_2$;
- —C(O)$CH_2$-t-Bu (DA-Tbg);
- —C(O)($CH_2$)$_2$-4-hydroxyphenyl;
- —C(O)—($CH_2$)$_3$—COOH;
- —C(O)O-t-Bu (Boc);
- —C(O)($CH_2$)$_5$$NH_2$; or
- —C(O)($CH_2$)$_5$NH-Boc.

4. A compound according to claim 3, wherein z is C;

X is $C_2F_5$; or —C(O)$NHR_6$ wherein
$R_6$ is —$CH_2$-phenyl; —$CH_2$-4-iodophenyl; —CH($CH_3$)-phenyl; —CH($CH_2CH_3$)-phenyl; —CH(Me)-naphthyl; —$CH_2$Co(Me)-phenyl; —($CH_2$)$_2$—O—$CH_2$-phenyl; —$CH_2$-2-benzimidazole; or —$CH_2$-(3, 4-methylenedioxybenzene);

$R_1$ is H or methyl;

$R_2$ is
- —$C_{12}$—C(O)—(N-pyrrolidino);
- —$CH_2$—C(O)—(N-morpholino);
- —($CH_2$)$_2$C(O)N($CH_3$)$_2$; or
- —($CH_2$)$_2$—C(O)—N($CH_3$)$CH_2CH_2$(2-pyridino);

W is ;NH $R_3$ is isopropyl or t-Bu;

$R_4$, when n mis 1, is t-Bu;

m is 0, and

Y is an acyl of formula:
- —C(O)$CH_2$-t-Bu (DA-Tbg);
- —C(O)O-t-Bu (Boc);
- —C(O)($CH_2$)$_5$$NH_2$; or
- —C(O)($CH_2$)$_5$NH-Boc.

5. A compound of formula

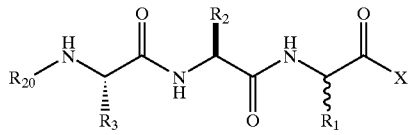

wherein

X is $CF_3$, $C_2F_5$, 2-benzothiazole, $CF_2CONHR_6$, $CONHRR_6$, wherein $R_6$ is $CH_2C_6H_5$, $CH_2$(4-iodophenyl), $CH_3$, $(CH_2)_2OCH_2C_6H_5$, $CH_2$-2-benzimidazole, $CH_2$-(3,4-methylenedioxybenzene), $CH(CH_3)C_6H_5$ or $CH(CH_2CH_3)C_6H_5$;

or X is 2-benzoxazole-$R_7$ wherein $R_7$ is H, 4-$CH_3$, 5-$CH_3$,6-$CH_3$ or 7-$CH_3$;

$R_1$ is H, $CH_3$ or $CH_2CH_3$;

$R_2$ is $CH_2CONH_2$, $CH_2CH_2CONH_2$, $CH_2$-thiazole, $CH_2CON(CH_3)_2$, or $CH_2CO$-pyrrolidino;

$R_3$ is Et, $CH(CH_3)_2$, $C(CH_3)_3$, adamantyl, $CH_2C(CH_3)_3$ or $C(CH_3)_2CO_2H$;

and $R_{20}$ is $COCH_2C(CH_3)_3$, $COCH_2CH_2C_6H_4OH$, $COCH_2CH(CH_3)_2$, $CO_2C(CH_3)_3$, $CONHC(CH_3)_3$, $COCH_2N(CH_3)_2$, $CO(CH_2)_3CO_2H$, CO—(S)—CH$(NH_2)C(CH_3)_3$, CO—(S)—CH{NHC(O)O—C($CH_3$)$_3$}C($CH_3$)$_3$, CO—(S)—CH{NHCO($CH_2$)$_5$NHC(O)OC($CH_3$)$_3$}C($CH_3$)$_3$ or CO—(S)—CH{NHCO($CH_2$)$_5$$NH_2$}C($CH_3$)$_3$.

6. A compound selected from the group consisting of:

N1-(3,3,3-trifluoro-1-methyl-2-oxopropyl)-(2S)-2-((1S)-2-methyl-1-[((1S)-2-methyl-1-[(methylcarboxamido)methyl] carboxamidopropyl) carboxamido] propyicarboxamido) butanediamide (37);

N1-(3,3,3-trifluoro-1-methyl-2-oxopropyl)-(2S)-6-amino-2-((1s)-1-[((1S)-1-[(1S)-2-hydroxy-1-(methylcarboxamido) ethyl]carboxamido-2-(4-hydroxyphenyl)ethyl) carboxamido]-2-methylpropylcarboxamido)hexanamide (38);

N1-(3,3,3-trifluoro-1-methyl-2-oxopropyl)-(2S)-2-[((1S)-2-methyl-1-[(1s)-2-methyl-1-(methylcarboxamido)propyl]carboxamidopropyl) carboxamido]butanediamide (39);

N1-(3,3,3-trifluoro-1-methyl-2-oxopropyl)-(2S)-2-{(1S)-2-methyl-1-[(methylcarboxamido)-propyl] carboxamido}butanediamide (40);

N1-(3,3,3-trifluoro-(1S)-methyl-2-oxopropyl)-(2S)-2-{(1S)-2-methyl-1-[(methylcarboxamido)propyl] carboxamido}butanediamide (43);

N1-(1-ethyl-3,3,3-trifluoro-2-oxopropyl)-(2S)-2-[((1S)-2-methyl-1-[(1S)-2-methyl-1-(methylcarboxamido) propyl]carboxamidopropyl) carboxamido] butanediamide (44);

N1-(1-(3,3,3,-trifluoro-1-propyl-2-oxopropyl)-(2S)-2-(((1S)-2-methyl-1-[((1S)-2-methyl-1-(methylcarboxamido) propyl]carboxamidopropyl) carboxamido]butanediamide (45);

N1-(3,3,3-trifluoro-1-methyl-2-oxopropyl)-(2S)-2-[((1S)-2-methyl-1-[(1S)- 2-methyl-1-(methylcarboxamido)propyl]carboxamidopropyl) carboxamido]pentanediamide (46);

(3S)-3-[((1S)-2-methyl-1-[(1S)-2-methyl-1-(methylcarboxamido)propyl]carboxamido-propyl) carboxamido]-3-[(3,3,3-trifluoro-1-methyl-2-oxopropyl)carbamoyl]propanoic acid (47);

N1-[(1S)-1-((1S)-2-hydroxy-1-[(3,3,3-trifluoro-1-methyl-2-oxopropyl)carbamoyl]ethyl-carbamoyl]-2-methylpropyl]-(2S)-3-methyl-2-(methylcarboxamido) butanamide (48);

N1-(3,3,3-trifluoro-1-methyl-2-oxopropyl)-(2S)-6-amino-2-[((1S)-2-methyl-1-[(1S)-2-methyl-1-(methylcarboxamido)propyl]carboxamidopropyl) carboxamido]hexanamide (49);

N1-[(1S)-2-methyl-1-((1S)-2-(1,3-thiazol-4-yl)-1-[(3,3,3-trifluoro-1-methyl-2-oxopropyl)-carbamoyl] ethylcarbamoyl) propyl]-(2S)-3-methyl-2-(methylcarboxamido)butanamide (50);

N4,N4-dimethyl-N1-(3,3,3-trifluoro-1-methyl-2-oxopropyl)-(2S)-2-[((1S)-2-methyl-1-[(1S)-2-methyl-1-(methylcarboxamido)propyl]carboxamidopropyl) carboxamido]butanediamide (51);

N1-[(1S)-2-methyl-1-((1S)-2-phenyl-1-[(3,3,3-trifluoro-1-methyl-2-oxopropyl)carbamoyl]-ethylcarbamoyl) propyl]-(2S)-3-methyl-2-(methylcarboxamido) butanamide (53);

N4,N4-dimethyl-N1-(3,3,3-trifluoro-1-methyl-2-oxopropyl)-(2S)-2-[((1S)-1-[( 1S)-2-methyl-1-(methylcarboxamido)propyl]carboxamidopropyl) carboxamido]butanediamide (57);

N4,N4-dimethyl-N1-(3,3,3-trifluoro-1-methyl-2-oxopropyl)-(2S)-2-[((1S)-2,2-dimethyl-1-[(1S)-2-methyl-1-(methylcarboxamido)propyl]carboxamido-propyl)carboxamido]butanediamide (58);

N4,N4-dimethyl-N1-(3,3,3-trifluoro-1-methyl-2-oxopropyl)-(2S)-2-[((1S)-3,3-dimethy-1-[(1S)-2-methyl-1-(methylcarboxamido)propyl]carboxamido butyl)carboxamido]butanediamide (59);

N4,N4-dimethyl-N1-(3,3,3-trifluoro-1-methyl-2-oxopropyl)-(2S)-2-[((S)-1-(1-adamantyl)-1-[(1S)-2-methyl-1-(methylcarboxamido)propyl]carboxamido methyl)carboxamido]butanediamide (60);

(3S)-3-((1S)-2-(dimethylcarbamoyl)-1-[(3,3,3-trifluoro-1-methyl-2-oxopropyl)carbamoyl]-ethylcarbamoyl)-2,2-dimethyl-3-[(1S)-2-methyl-1-(methylcarboxamido)propyl]carboxamidopropanoic acid (61);

N4,N4-dimethyl-N1-(3,3,3-trifluoro-1-methyl-2-oxopropyl)-(2S)-2-[(1S)-2,2-dimethyl-1-(methylcarboxamido)propyl]carboxamidobutanediamide (62);

N4,N4-dimethyl-N1-(3,3,3-trifluoro-1-methyl-2-oxopropyl)-(2S)-2-((1S)-1-[(4-hydroxyphen-ethyl)carboxamido]-2,2-dimethylpropylcarboxamido)butanediamide (63);

N4,N4-dimethyl-N1-(3,3,3-trifluoro-1-methyl-2-oxopropyl)-(2S)-2-[(1S)-1-(isobutylcarboxamido)-2,2-dimethylpropyl]carboxamidobutanediamide (64);

N4,N4-dimethyl-N1-(3,3,3-trifluoro-1-methyl-2-oxopropyl)-(2S)-2-[(1S)-2,2-dimethyl-1-(neopentylcarboxamido)propylcarboxamido]butanediamide (65);

N4,N4-dimethyl-N1-(3,3,3-trifluoro-1-methyl-2-oxopropyl)-(2S)-2-((1S)-1-[(3,3-dimethyl-butyl)amino]-2,2-dimethylpropylcarboxamido]butanediamide (66);

4N,4N-Dimethyl-1N-(3,3,3-trifluoro-1-methyl-2-oxopropyl)-2-[1-(tert-butoxycarbonyl-amino)-2,2-dimethyl-(1S)-propylcarboxamido]-(2S)-butanediamide (67);

N4,N4-Dimethyl-N1-(3,3,3-trifluoro-1-methyl-2-oxopropyl-2-[1-(tert-butylaminocarbonyl-amino)-2,2-dimethyl-(1S)-propylcarboxamido]-(2S)-butanediamide (68);

N4,N4-dimethyl-N1-(3,3,3-trifluoro-1-methyl-2-oxopropyl)-(2S)-2-[((1S)-1-[(dimethyl-amino)methyl]carboxamido-2,2-dimethylpropyl) carboxamido]butanediamide (69);

4-[(1S)-1-((1S)-2-(dimethylcarbamoyl)-1-[(3,3,3-trifluoro-1-methyl-2-oxopropyl)carbamoyl]ethylcarbamoyl)- 2,2-dimethylpropyl]carbamoylbutanoic acid (70);

N4,N4-dimethyl-N1-(3,3,4,4,4-pentafluoro-1-methyl-2-oxobutyl)-(2S)-2-[(1S)-2,2-dimethyl-1-(neopentyl carboxamido)propyl]carboxamidobutanediamide (74);

N1-[3-(benzylcarbamoyl)-3,3-difluoro-1-methyl-2-oxopropyl -N4,N4-dimethyl-(2S)-2-[(1S)-2,2-dimethyl-1-(neopentylcarboxamido)propyl]carboxamidobutanediamide (75);

3-{2-[2-(3,3-Dimethyl-butyrylamino)-3,3-dimethyl-butyrylamino]-3-dimethylcarbamoyl-propionylamino}-2-oxo-butyric acid benzyl amide (76);

N1-[2-(1,3-benzoxazol-2-yl)-1-methyl-2-oxoethyl]-N4,N4-dimethyl-(2S)-2-{[(1S)-2,2-dimethyl-1-(neopentylcarboxamido)propyl]carboxamido}butanediamide (77);

Diphenyl N4,N4-dimethyl-N1-(1-aminoethylphosphinate)-(2S)-2-{[(1S)-2,2-dimethyl-1-(neopentylcarboxamido)propyl]carboxamido}butane diamide (79);.

N1-[2-(1,3-benzothiazol-2-yl)-1-methyl-2-oxoethyl]-N4,N4-dimethyl-(2S)-2-{[(1S)-2,2-di-methyl-1-(neopentylcarboxamido)propyl]carboxamido}butane diamide (80);

N4,N4-dimethyl-N1-(1-methyl-2-[1,3]oxazolo[4,5-b]pyridin-2-yl-2-oxoethyl)-(2S)-2-{[(1S)-2,2-dimethyl-1-(neopentylcarboxamido)propyl]carboxamido} butanediamide (81);

N4,N4-dimethyl-N1-[1-methyl-2-(6-methyl-1,3-benzoxazol-2-yl)-2-oxoethyl]-(2S)-2-{[(1S)-2,2-dimethyl-1-(neopentylcarboxamido)propyl]carboxamido}butanediamide (82);

N4,N4-dimethyl-N1-[1-methyl-2-(5-methyl-1,3-benzoxazol-2-yl)-2-oxoethyl]-(2S)-2-{[(1S)-2,2-dimethyl-1-(neopentylcarboxamido)propyl]carboxamido}butanediamide (83);

N4,N4-dimethyl-N1-[1-methyl-2-(4-methyl-1,3-benzoxazol-2-yl)-2-oxoethyl]-(2S)-2-{[(1S)-2,2-dimethyl-1-(neopentylcarboxamido)propyl]carboxamido}butanediamide (84);

N4,N4-dimethyl-1M -[1-methyl-2-(7-methyl-1,3-benzoxazol-2-yl)-2-oxoethyl]-(2S)-2-{[(1S)-2,2-dimethyl-1-(neopentylcarboxamido)propyl]carboxamido}butanediamide (85);

N4,N4-dimethyl-N1-[1-methyl-2-(methylcarbamoyl)-2-oxoethyl]-(2S)-2-{[(1S)-2,2-dimethyl-1-(neopentylcarboxamido)propyl]carboxamido}butanediamide (86);

N1-(2-[2-(benzyloxy)ethylcarbamoyl-1-methyl-2-oxoethyl)-N4,N4-dimethyl-(2S)-2-{[(1S)-2,2-dimethyl-1-(neopentylcarboxamido)propyl]carboxamido}butanediamide (88);

N1-2-[(1,3-benzodioxol-5-ylmethyl)carbamoyl]-1-methyl-2-oxoethyl-N4,N4-dimethyl-(2S)-2-{[(1S)-2,2-dimethyl-1-(neopentylcarboxamido)propyl]carboxamido}butanediamide (89);

N1-2-[(1H-benzo[d]imidazol-2-ylmethyl)carbamoyl]-1-methyl-2-oxoethyl-N4,N4-dimethyl-(2S)-2-{[(1S)-2,2-dimethyl-1-(neopentylcarboxamido)propyl]carboxamido}butanediamide (90);

N4,N4-dimethyl-N1-(1-methyl-2-oxo-2-[(1S)-1-phenylethyl]carbamoylethyl)-(2S)-2-{[(1S)-2,2-dimethyl-1-(neopentylcarboxamido)propyl]carboxamido}butanediamide (91);

N4,N4-dimethyl-N1-(1-methyl-2-oxo-2-[(1R)-1-phenylethyl]carbamoylethyl)-(2S)-2-{[(1S)-2,2-dimethyl-1-(neopentylcarboxamido)propyl]carboxamido}butanediamide (92);

N4,N4-dimethyl-N1-(1-methyl-2-oxo-2-[(1R)-1-phenylpropyl]carbamoylethyl)-(2S)-2-{[(1S)-2,2-dimethyl-1-(neopentylcarboxamido)propyl]carboxamido}butanediamide (93);

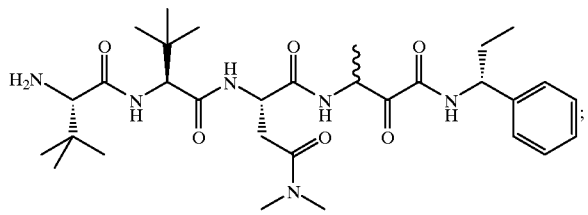
94
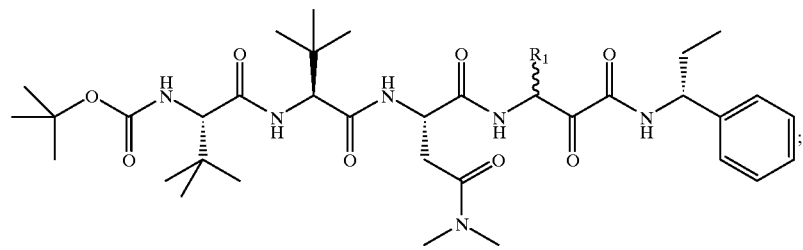
95
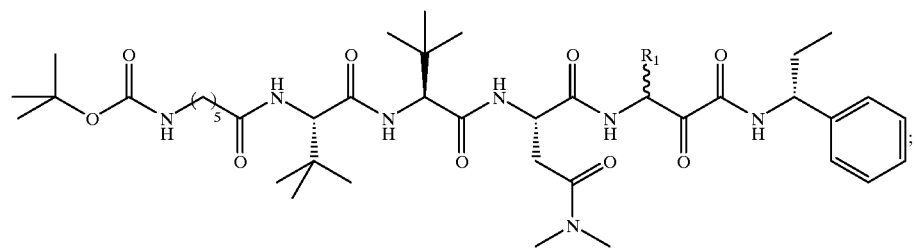
96
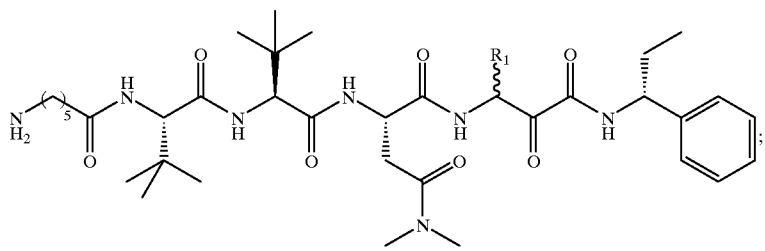
97
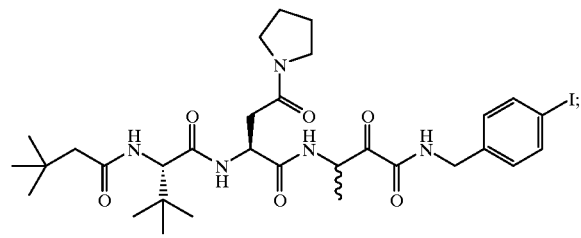
98
Ac-Ser-Tyr-Val-Lys-Ala (d,l)—C(O)—NH—CH₂—Ph 218;

105 106
301 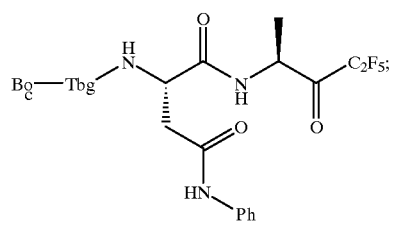
302 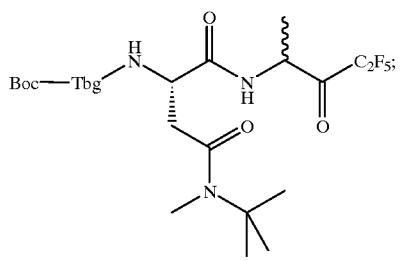
303 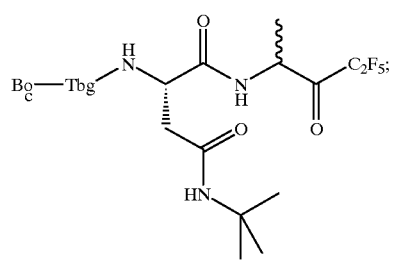
304 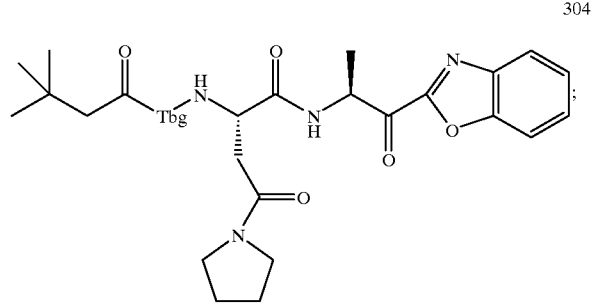
305 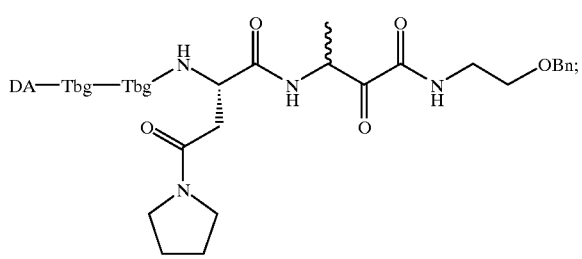
306 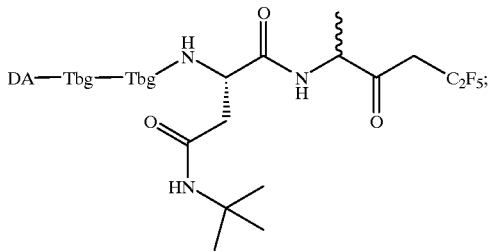
307 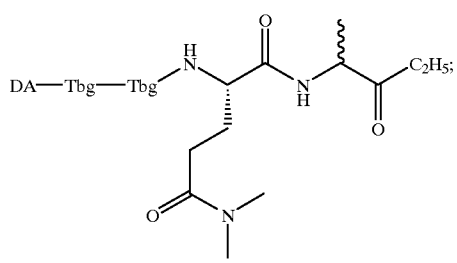
308 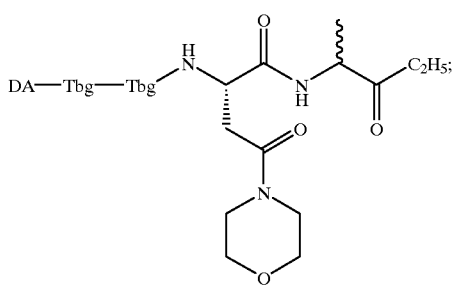
309 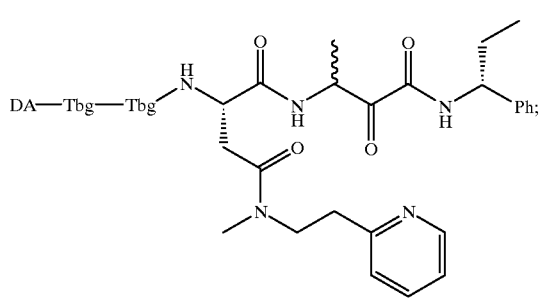
310 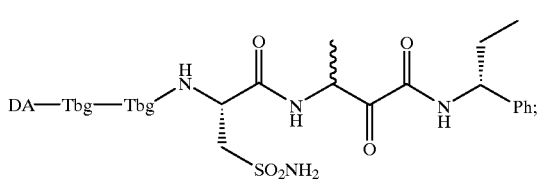

-continued
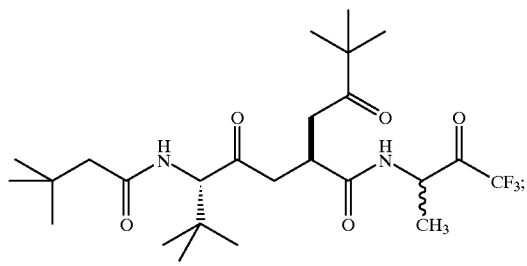
311
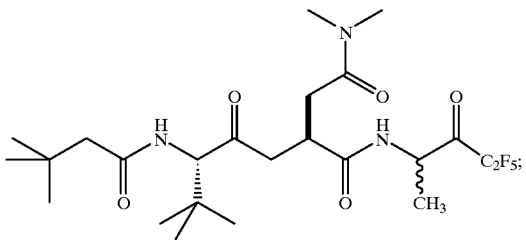
312
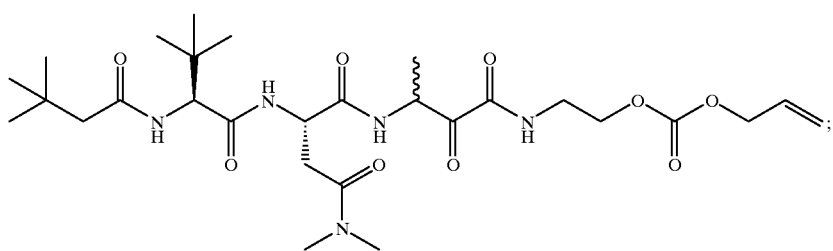
401
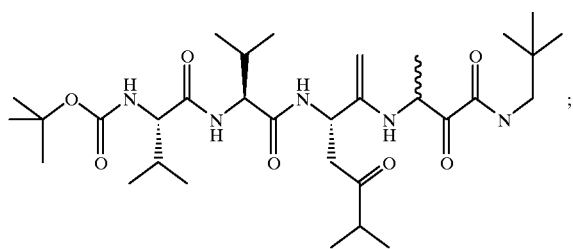
402
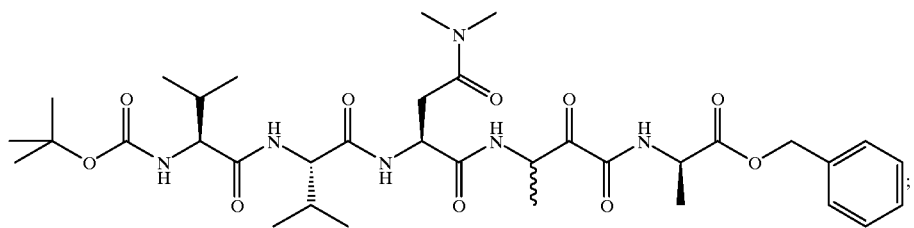
403
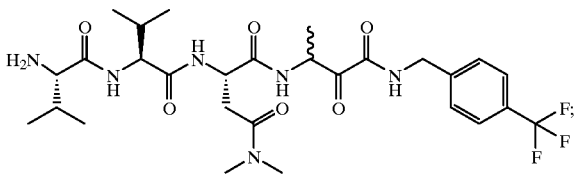
404
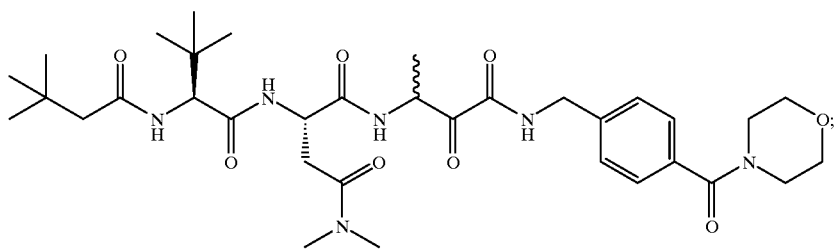
405

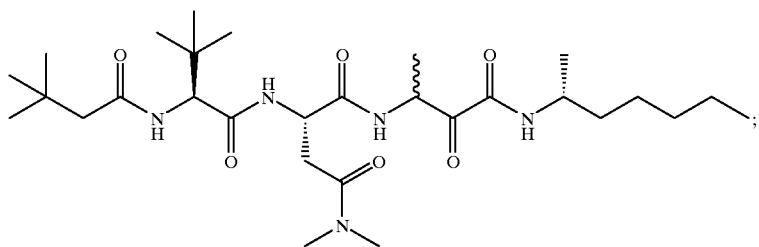
406
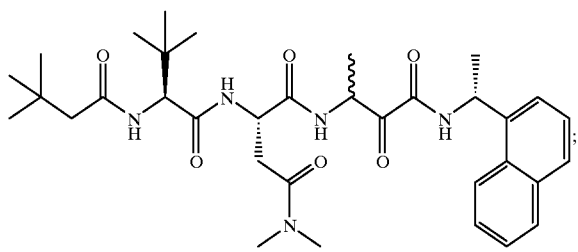
407
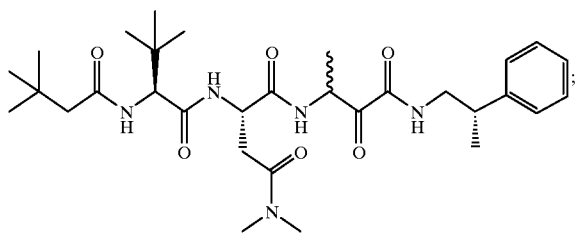
408
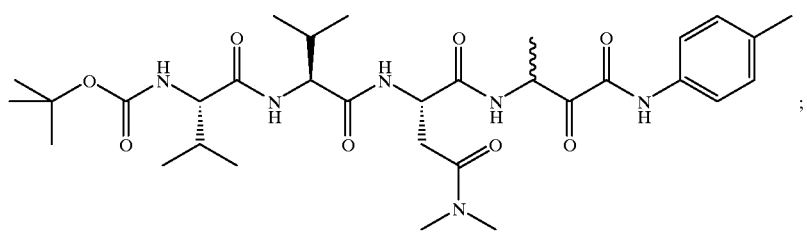
409
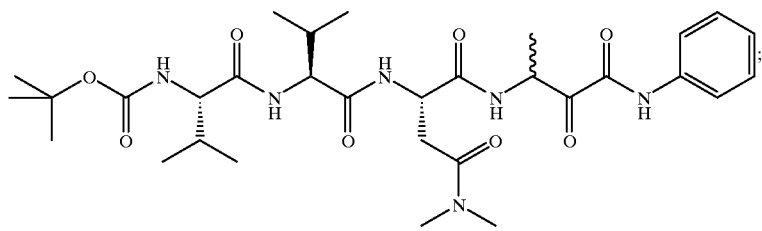
410
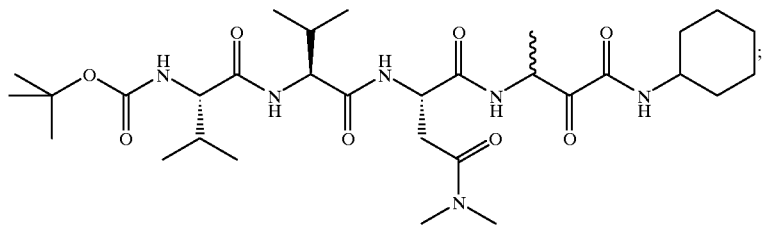
411

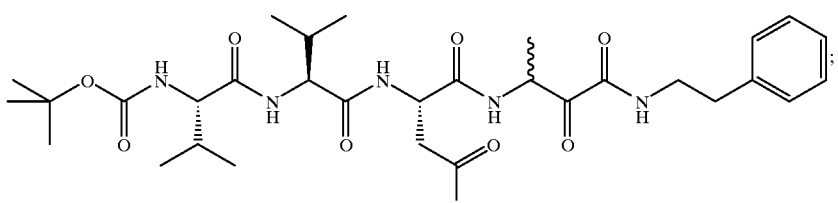

412

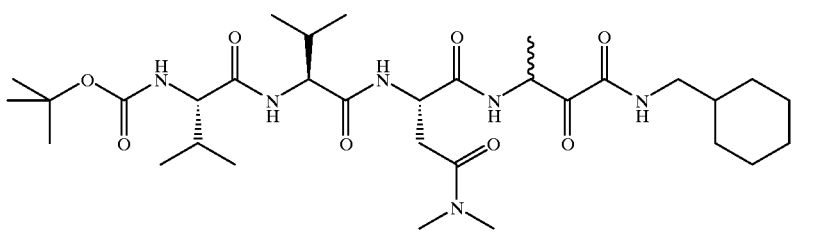

413 and

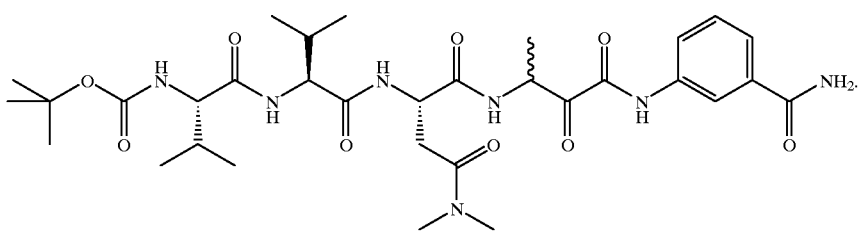

414

7. The compound according to claim 6, selected from the group consisting of: compound number 37, 38, 39, 44, 46, 50, 51, 53, 57, 58, 59, 60, 62, 63, 64, 65, 66, 67, 68, 69, 70, 74, 75, 76, 77, 79, 80, 82, 83, 84, 85, 86, 88, 89, 90, 91, 92, 93, 94, 95, 96, 97, 98, 218, 301, 302, 303, 304, 305, 306, 307, 308, 309, 310, 311, 312, and 401 to 414.

8. The compound according to claim 7, selected from the group consisting of: compound number 37, 51, 58, 63, 64, 65, 70, 74, 75, 76, 77, 79, 80, 82, 83, 84, 85, 86 88, 89, 90, 92, 93, 94, 95, 96, 97, 98, 304, 305, 306, 307, 308, 309, 310, 311, 312, 401, 403, 404, 405, 406, 407, 408, 409, 410, 411, 412, and 414.

9. The compound according to claim 8, selected from the group consisting of: compound number 74, 76, 88, 89, 90, 92, 93, 95, 96, 97, 98, 305, 308, 309, 407, and 408.

10. A process for the solid phase synthesis of peptidyl activated ketones of formula I below, wherein said process is represented by the following reaction scheme:

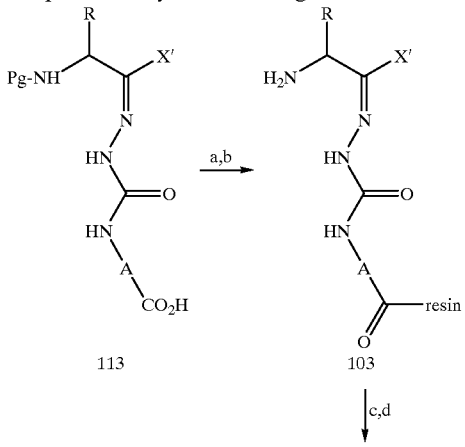

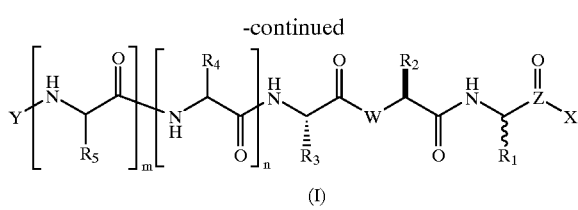

(I)

wherein R is H, Me or Et;
and X' is $CF_3$, $CF_2CONH-R_{30}$, or $C(O)NH-R_{30}$, wherein $R_{30}$ is selected from: cyclohexyl, being optionally substituted with halogen, $C_{0-10}$ alkyl optionally substituted with phenyl, said phenyl ring being optionally substituted with Me or halogen, said phenyl ring optionally fused with a second phenyl ring;
$(CH_2)_3$—O—$(CH_2)_{1-3}$-phenyl, said phenyl optionally substituted with halogen;
$(CH_2)_{1-3}$-2-benzimidazole; or
$(CH_2)_{1-3}$-(3,4-methylenedioxybenzene);
A is a divalent spacer group which comprises a non-reactive divalent hydrocarbyl group having from 2 to 15 carbon atoms;
and
Pg is an amino protecting group;
and wherein said process comprises the steps of:
  a) coupling a semicarbazone acid of formula 113 to a resin by in situ activation;
  b) deprotecting said amino protecting group to give the resin of formula 103;
  c) coupling said resin with amino acids in a sequential manner by standard chemistry to obtain a peptide coupled to said resin;
and
  d) cleaving said peptide from said resin to obtain a peptidyl activated ketone of formula I, wherein z is C, X has the same definition as X' above, R, has the same definition as R above, and $R_2$, $R_3$, R4, $R_5$, W, m, n and Y are as defined in claim 24.

11. The process of claim 10, wherein said cleavage step is carried out in THF, aqueous HCl, and AcOH at a temperature of about 60° C. for about 4 hours; and said resin is filtered at least once.

12. The process of claim 10, wherein said resin is selected from the group consisting of: polystyrene or pegyiated polystyrene functionalized with benzydrylamine (BHA); 4-methyl benzydrylamine (MBHA); and aminomethyl (AM).

13. The process of claim 10, wherein said in situ activation is carried out with the addition of a coupling agent selected from the group consisting of: 2-(1H-benzotriazol-1-yl)-1,1,3,3-tetramethyluronium tetrafluoroborate (TBTU); 2-(1H-benzotriazol-1 -yl)-1,1,3,3-tetramethyluronium hexafluorophosphate (HBTU); diisopropyl carbodiimide (DIC); and dicyclohexyl carbodiimide (DCC).

14. The process of claim 10, wherein said amino protecting group is selected from the group consisting of: t-butyloxycarbonyl (Boc); 9-fluorenylmethyloxy carbonyl (Fmoc); and allyloxy carbonyl (Alloc).

15. The process of claim 10, wherein X' is $C(O)NHCH_2$-phenyl.

16. The process of claim 10, wherein R is selected from the group consisting of: $CH_3$ and $CH_2CH_3$.

17. The process of claim 10, wherein A is cyclohexyl, phenyl or benzyl.

18. A process for the solid phase synthesis of peptidyl activated ketones of formula I below, comprising the steps of:

(1) coupling a resin 103 set forth below with amino acids in a sequential manner by standard chemistry to obtain a peptide coupled to said resin:

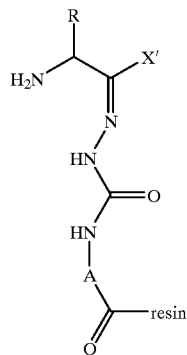

103 wherein R is H, Me or Et;

X' is $CF_3$, $CF_2CONH-R_{30}$, or $C(O)NH-R_{30}$, wherein $R_{30}$ is selected from:

cyclohexyl, being optionally substituted with halogen, $C_{0-10}$ alkyl optionally substituted with phenyl, said phenyl ring being optionally substituted with Me or halogen, said phenyl ring optionally fused with a second phenyl ring;

$(CH_2)_{1-3}$—O—$(CH_2)_{1-3}$-phenyl, said phenyl optionally substituted with halogen;

$(CH_2)_{1-3}$-2-benzimidazole; or $(CH_2)_{1-3}$-(3,4-methylenedioxybenzene);

and

A is a divalent spacer group which comprises a non-reactive divalent hydrocarbyl group having from 2 to 15 carbon atoms; and (2) cleaving said peptide from said resin to obtain a peptidyl activated ketone of formula I below:

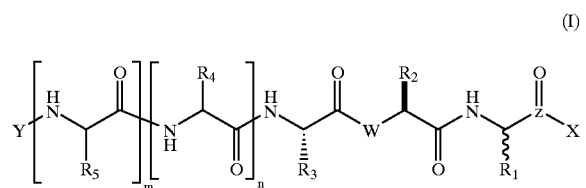

(I)

wherein z is C, X has the same definition as X' above, $R_1$ has the same definition as R above, and $R_2$, $R_3$, $R_4$, $R_5$, W, m, n and Y are as defined in claim 24.

19. A process according to claim 18, wherein said resin is selected from the group consisting of: polystyrene or pegylated polystyrene functionalized with benzydrylamine (BHA); 4-methyl benzydrylamine (MBHA); and aminomethyl (AM).

20. A process according to claim 18, wherein A is cyclohexyl, phenyl or benzyl.

* * * * *